(12) United States Patent
Cunningham et al.

(10) Patent No.: US 7,854,505 B2
(45) Date of Patent: Dec. 21, 2010

(54) PASSIVE AND ACTIVE PHOTONIC CRYSTAL STRUCTURES AND DEVICES

(75) Inventors: Brian T. Cunningham, Champaign, IL (US); Dennis W. Dobbs, Boulder, CO (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 903 days.

(21) Appl. No.: 11/686,452

(22) Filed: Mar. 15, 2007

(65) Prior Publication Data
US 2009/0323014 A1 Dec. 31, 2009

Related U.S. Application Data

(60) Provisional application No. 60/782,565, filed on Mar. 15, 2006.

(51) Int. Cl.
G02C 7/10 (2006.01)
G02F 1/00 (2006.01)

(52) U.S. Cl. .................. 351/44; 359/238; 359/321; 385/12

(58) Field of Classification Search ............ 351/41, 351/163, 165, 166; 359/237, 238, 298, 321, 359/618, 627, 634; 356/478, 481; 385/12; 398/45, 48, 51; 428/824, 824.5
See application file for complete search history.

(56) References Cited

U.S. PATENT DOCUMENTS

| 5,399,897 | A | 3/1995 | Cunningham et al. |
| 5,440,421 | A | 8/1995 | Fan et al. |
| 5,600,483 | A | 2/1997 | Fan et al. |
| 5,688,318 | A | 11/1997 | Milstein et al. |
| 5,688,699 | A | 11/1997 | Cunningham et al. |
| 5,900,630 | A | 5/1999 | Tang et al. |
| 5,903,383 | A | 5/1999 | Bernstein et al. |
| 6,262,830 | B1 | 7/2001 | Scalora |
| 6,411,451 | B1 | 6/2002 | Fliss et al. |
| 6,589,452 | B2 | 7/2003 | Asher et al. |
| 6,688,158 | B2 | 2/2004 | Cunningham et al. |
| 6,857,741 | B2 | 2/2004 | Blum et al. |

(Continued)

FOREIGN PATENT DOCUMENTS

WO    WO 99/42892    8/1999

(Continued)

OTHER PUBLICATIONS

Aoshima et al. (2000) "The Optical Properties of Azobenzene-Containing Urethane-Urea Copolymer Films for Data Storage," *Polym. Adv. Technol.* 11:575-578.

(Continued)

*Primary Examiner*—Huy K Mai
(74) *Attorney, Agent, or Firm*—Greenlee Sullivan P.C.

(57) ABSTRACT

The present invention provides photonic crystal devices, device components and methods for preventing transmission of electromagnetic radiation from one or more laser sources or laser modes so as to provide an optical shield for protecting a users eyes or an optical sensor. The present invention also provides dynamic photonic crystals and devices incorporating dynamic photonic crystals for optically modulating the intensity of one or more beams of electromagnetic radiation and other optical switching applications.

100 Claims, 20 Drawing Sheets

U.S. PATENT DOCUMENTS

| | | | |
|---|---|---|---|
| 6,716,475 B1 | 4/2004 | Fink et al. |
| 6,828,575 B2 | 12/2004 | Luo et al. |
| 6,833,938 B2 | 12/2004 | Nishioka |
| 6,837,097 B2 | 1/2005 | Cunningham et al. |
| 6,851,297 B2 | 2/2005 | Cunningham et al. |
| 6,937,781 B2 | 8/2005 | Shirane et al. |
| 6,947,649 B2 | 9/2005 | Li et al. |
| 6,951,715 B2 | 10/2005 | Cunningham et al. |
| 6,990,259 B2 | 1/2006 | Cunningham |
| 6,999,156 B2 | 2/2006 | Chou et al. |
| 7,000,453 B2 | 2/2006 | Cunningham et al. |
| 7,023,544 B2 | 4/2006 | Cunningham et al. |
| 7,031,566 B2 * | 4/2006 | Kochergin et al. ............ 385/27 |
| 7,070,987 B2 | 7/2006 | Cunningham et al. |
| 7,074,311 B1 | 7/2006 | Cunningham et al. |
| 7,094,595 B2 | 8/2006 | Cunningham et al. |
| 7,109,633 B2 | 9/2006 | Weinberg et al. |
| 7,118,710 B2 | 10/2006 | Cunningham et al. |
| 7,142,296 B2 | 11/2006 | Cunningham et al. |
| 7,148,964 B2 | 12/2006 | Cunningham et al. |
| 7,153,702 B2 | 12/2006 | Lin et al. |
| 7,158,230 B2 | 1/2007 | Cunningham et al. |
| 7,170,599 B2 | 1/2007 | Cunningham |
| 7,175,980 B2 | 2/2007 | Qiu et al. |
| 7,197,198 B2 | 3/2007 | Schulz et al. |
| 7,202,076 B2 | 4/2007 | Cunningham et al. |
| 7,217,574 B2 | 5/2007 | Pien et al. |
| 7,264,973 B2 | 9/2007 | Lin et al. |
| 7,266,990 B2 | 9/2007 | Cunningham et al. |
| 7,292,336 B2 | 11/2007 | Cunningham et al. |
| 7,298,477 B1 | 11/2007 | Cunningham et al. |
| 7,300,803 B2 | 11/2007 | Lin et al. |
| 7,300,814 B2 | 11/2007 | Cunningham et al. |
| 7,301,628 B2 | 11/2007 | Cunningham et al. |
| 7,309,614 B1 | 12/2007 | Baird et al. |
| 7,312,090 B2 | 12/2007 | Lin et al. |
| 7,327,454 B2 | 2/2008 | Cunningham et al. |
| 7,371,562 B2 | 5/2008 | Cunningham et al. |
| 7,422,891 B2 | 9/2008 | Cunningham |
| 7,468,138 B2 | 12/2008 | Weinberg et al. |
| 7,479,404 B2 * | 1/2009 | Cunningham et al. ......... 438/69 |
| 7,497,992 B2 | 3/2009 | Cunningham et al. |
| 7,521,769 B2 | 4/2009 | Cunningham |
| 7,531,786 B2 | 5/2009 | Cunningham et al. |
| 7,534,578 B1 | 5/2009 | Baird et al. |
| 7,575,939 B2 | 8/2009 | Cunningham et al. |
| 7,611,836 B2 | 11/2009 | Qiu et al. |
| 7,615,339 B2 | 11/2009 | Cunningham et al. |
| 7,622,027 B1 | 11/2009 | Cunningham |
| 7,718,440 B2 | 5/2010 | Pien et al. |
| 7,737,392 B2 | 6/2010 | Cunningham et al. |
| 7,742,662 B2 | 6/2010 | Cunningham |
| 2002/0041445 A1 | 4/2002 | Nishioka et al. |
| 2002/0187464 A1 | 12/2002 | Klempner et al. |
| 2003/0003575 A1 | 1/2003 | Vacanti et al. |
| 2003/0017580 A1* | 1/2003 | Cunningham et al. .... 435/287.2 |
| 2003/0022361 A1 | 1/2003 | Houston et al. |
| 2003/0026891 A1 | 2/2003 | Qiu et al. |
| 2003/0027327 A1 | 2/2003 | Cunningham et al. |
| 2003/0186464 A1 | 10/2003 | Arkin et al. |
| 2003/0235862 A1 | 12/2003 | Arkin et al. |
| 2004/0080805 A1* | 4/2004 | Levy .......................... 359/280 |
| 2004/0131797 A1 | 7/2004 | Yokoyama et al. |
| 2004/0132172 A1 | 7/2004 | Cunningham et al. |
| 2004/0151626 A1 | 8/2004 | Cunningham et al. |
| 2005/0090812 A1 | 4/2005 | Shadduck |
| 2005/0140924 A1 | 6/2005 | Blum et al. |
| 2005/0159623 A1 | 7/2005 | McGinniss et al. |
| 2006/0030033 A1 | 2/2006 | Cunningham et al. |
| 2007/0009380 A1 | 1/2007 | Cunningham |
| 2007/0148139 A1 | 6/2007 | Vacanti et al. |
| 2007/0200499 A1 | 8/2007 | Eden et al. |
| 2008/0014632 A1 | 1/2008 | Cunningham et al. |
| 2008/0103056 A1 | 5/2008 | Lin et al. |
| 2008/0219892 A1 | 9/2008 | Cunningham et al. |
| 2008/0240543 A1 | 10/2008 | Budach et al. |
| 2008/0246961 A1 | 10/2008 | Zhang et al. |
| 2008/0278722 A1 | 11/2008 | Cunningham et al. |
| 2009/0130703 A1 | 5/2009 | Wagner et al. |
| 2009/0148955 A1 | 6/2009 | Cunningham et al. |
| 2009/0179637 A1 | 7/2009 | Cunningham et al. |
| 2009/0226950 A1 | 9/2009 | Cunningham et al. |
| 2009/0264314 A1 | 10/2009 | Cunningham et al. |
| 2009/0269244 A1 | 10/2009 | Cunningham et al. |
| 2010/0003743 A1 | 1/2010 | Schulz et al. |
| 2010/0085566 A1 | 4/2010 | Cunningham |
| 2010/0143959 A1 | 6/2010 | Cunningham et al. |

FOREIGN PATENT DOCUMENTS

| | | |
|---|---|---|
| WO | WO 01/63345 | 8/2001 |
| WO | WO 2004/106982 | 12/2004 |
| WO | WO 2005/076721 | 8/2005 |
| WO | WO 2005/096783 | 10/2005 |

OTHER PUBLICATIONS

Crisostomo et al. (1995) "Analysis of the Selective Behavior of Multilayer Structures with a dielectric Grating," *IEEE Trans. Antennas Propagation.* 43:529-533.

Cunningham et al. (Sep. 2004) "Label-Free Assays on the BIND System," *J. Biomol. Screen.* 9:481-490.

Cunningham et al. (2002) "Enhancing the Surface Sensitivity of Colorimetric Resonant Optical Biosensors," *Sensors and Actuators B* 87:365-370.

Cunningham et al. (2002) "Colorimetric Resonant Reflection as a Direct Biochemical Assay Technique," *Sensors Actuators B* 81:316-328.

DeSandre et al. (1991) "Extinction-Theorem Analysis of Diffraction Anomalies in Overcoated Gratings," *J. Opt. Soc. Am.* 8:763-777.

Hessel et al. (1965) "A New Theory of Wood's Anomalies on Optical Gratings," *Appl. Optics* 4:1275-1297.

Hore et al. (1998) "Irradiance and Temperature Dependence of Photoinduced Orientation in Two Azobenzene-Based Polymers," *Can. J. Chem.* 76:1648-1653.

Ivanov (2005) "Temperature-Dependent Light Intensity Controlled Optical Switching in Azobenzene Polymers," *Appl Phys. Lett.* 86:181902.

Liu et al. (2002) "Concept of Multiorder Multimode Resonant Optical Filters," *IEEE Photonics Technol. Lett.* 14:1091-1093.

Magnusson et al. (1995) "Transmission Bandpass Guided Mode Resonance Filters," *Applied Optics* 34:8106-8109.

Magnusson et al. (1992) "New Principle for Optical Filters," *Applied Physics Lett.* 61:1022-1024.

Mahnkopf et al. (2004) "Tunable Photonic Crystal Coupled-Cavity Laser," *IEEE J. Quantum Electron.* 40:1306-1314.

Moharam et al. (1981) "Rigorous Coupled-Wave Analysis of Planar-Grafting Diffraction," *J. Opt. Soc. Am.* 71:811-818.

Munk, B.A. (2000) "Band-Stop and Dichroic Filter Designs," In; *Frequency Selective Surfaces,* John Wiley & Sons, pp. 279-312.

Nedelcehev et al. (2003) "Photoinduced Anisotropy in a Family of Amorphous Azobenzene Polyesters for Optical Storage," *Applied Optics* 42:5918-5927.

Neviere et al. (1973) "About the Theory of Optical Grafting Coupler-Waveguide Systems," *Opt. Commun.* 8:113-117.

Pacradouni et al. (2000) "Photonic Band Structure of Dielectric Membranes Periosically Textured in Two Dimensions," *Phys. Rev. B.* 62:4202-4207.

Pederson et al. (2000) "Characterization of Azobenzene Chromophores for Reversible Optical Data Storage: Molecular Quantum Calculations," *J. Optics A.* 2:272-278.

Puscasa et al. (2001) "Modeling Parameters for the Spectral Behavior of Infrared Frequent-Selective Surfaces," *Appl. Optics* 40:118-124.

Quang et al. (1997) "Coherent Control of Spontaneous Emission," *Phys. Rev. Lett.* 79:5238-5241.

Rodriguez et al. (2004) "Optical Anisotropy and Nonlinear Optical Properties of Azobenzene Methacrylic Polymers," *Polymer* 45:2341-2348.

Russell, P. (2003) "Photonic Crystal Fibers," *Science* 299:358-362.

Sekkat et al. (2002) "Photo-Orientation by Photoisomerization," In; *Photoreactive Organic Thin Films*, Sekkat et al. eds., Academic Press, Amsterdam, pp. 63-104.

Tibuleac et al. (1997) "Diffractive Narrow-Band Transmission Filters Based on Guided-Mode Resonance Effects in Thin-Film Multilayers," *IEEE Photonics Technol. Lett.* 9:464-466.

Tokushima et al. (2002) "Light Propagation in a Photonic-Crystal-Slab Line-Defect Waveguide," *IEEE J. Quantum Electron.* 38:753-759.

Wang et al. (2003) "Ultrafast Photoinduced Anisotropy and Optical Switching in Azobenzene Sidechain Polymers," *Appl. Phys. Lett.* 82:3394-3396.

Wang et al. (2002) "Optical Properties of Disperse-Red-1-Doped Nematic Liquid Crystal," *J. Mater. Sci. Mater. Electron.* 13:173-1798.

Wang et al. (1994) Design of Waveguide-Grating filters with Symmetrical Line Shapes and Low Sidebands, *Optics Lett.* 19:919-921.

Wu et al. (2001) "Nonvolatile Grating in an Azobenzene Polymer with Optimized Molecular Reorientation," *Appl. Phys. Lett.* 78:1189-1191.

Wu et al. (2003) "All-Optical Switching Effects in Poly(methyl methacrylate) Composites," *Reac. Funct. Polym.* 56:83-88.

Yablonovitch, E. (1987) "Inhibited Spontaneous Emission in Solid-State Physics and Electronics," *Phys. Rev. Lett.* 58:2059-2062.

Yi et al. (2003) "Photoinduced Anisotropy of Second-Harmonic Generation from Azobenzene-Modified Alkysiloxane Monolayers," *J. Vac. Sci. Technol.* 21:1770-1775.

Yokouchi et al. (2003) "Two-Dimensional Photonic Crystal Confined Vertical-Cavity Surface-Emitting Lasers," *IEEE J Select. Top. Quantum Electron.* 9:1439-1445.

Birner et al. "Silicon-Based Photonic Crystals," *Adv. Mater.* 13(6):377-388, (2001).

Boye et al. (1999) "Resonant Wave-guide-Grating Switching Device with Nonlinear Optical Material," *Appl. Optics.* 38:5181-5185.

Cunningham et al. (2002) "A Plastic Colorimetric Resonant Optical Biosensor for Multiparallel Detection of Label-Free Biochemical Interactions," *Sensors and Actuators B*. 85:219-226.

Divliansky et al. (Mar. 17, 2003) "Fabrication of Three-Dimensional Polymer Photonic Crystal Structures Using Single Diffraction Element Interference Lithography," *Appl. Phys. Lett.* 82(11):1667-1669.

Gaughan, R. (Jan. 2000) "Researchers Create Tunable Photonic Bandgap Crystal," *Photonics Technology News* http://www.physics.utoronto.ca/~john/techCrystal.html.

Heuss, C. (Mar. 6, 2002) "Photonic Crystals may Become the 'Transistor of the 21$^{st}$ Century'," Scholar Predicts," *Stanford Report*.

Jacob et al. (2002) "Flat-top narrow-band spectral response obtained from cascaded resonant grating reflection filters," *Appl. Optics*, 41(7): 1241-1245.

Luo et al. (2005) "Improvement of All-Optical Switching Based on Azobenzene-Containing Polymer Films," *Appl. Phys. B*. 80:77-80.

Magarinos et al. (1987) "Holographic optical configurations for eye protection against lasers," *Appl. Optics*, 26(13): 2575-2581.

Natansohn et al.(2002) "Photoinduced Motions in Azobenzene-Based Polymers," In; *Photoreactive Organic Thin Films*, Sekkat et al. eds., Academic Press, Amsterdam, Ch 13, pp. 399-427.

Park et al. (Nov. 22, 2004) "Mechanically Tunable Photonic Crystal Structure," *Appl. Phys. Lett.* 85(21):4845-4847.

Parker et al. (Aug. 2000) "Photonic Crystals," *Physics World—Physics Web* http://Physicsweb.org/articles/world/13/8/9/1 , Downloaded Feb. 9, 2006.

Peng et al. "Resonant Scattering from Two-Dimensional Gratings," *J. Optical Soc. Am. A* 13:993-1005, (1996).

Suh et al. (2003) "Mechanically Switchable Photonic Crystal Filter with Either All-Pass Transmission of Flat-Top Reflection Characteristics," *Optics Lett.* 28:1763-1765.

Wang et al. (1993) "Theory and Applications of Guided-Mode Resonance Filters," *Appl. Optics* 32:2606-2613.

Wu et al. (2003) "Optical Power Limiting with Photoinduced Anisotropy of Azobenzene Films," *Appl. Optics* 42:4560-4565.

Wu et al. (2004) "All-Optical Sitching Effect in PVK-Based Optoelectronic Composites," *Mater. Chem. Phys.* 83:29-33.

\* cited by examiner

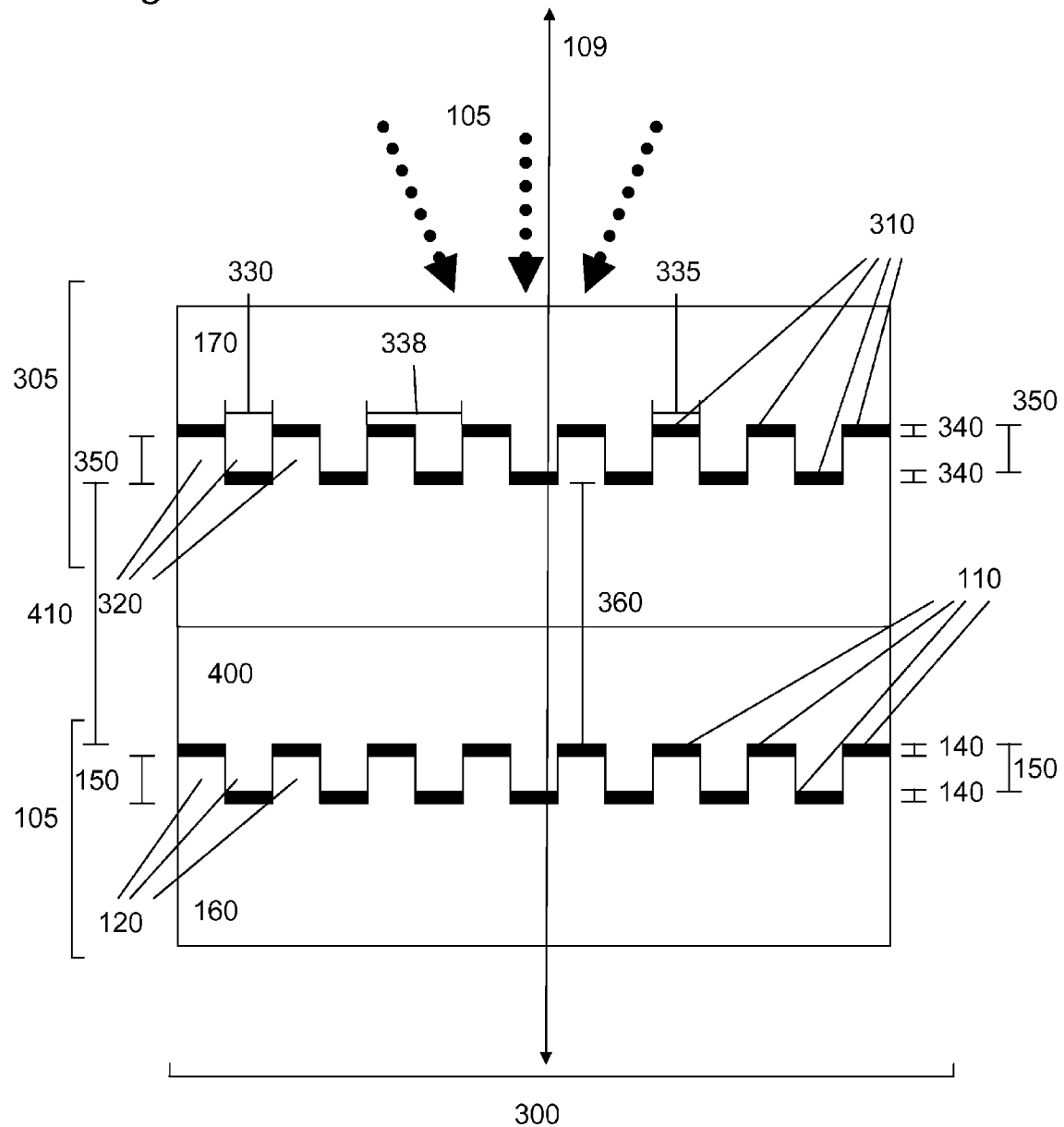

a)

b)

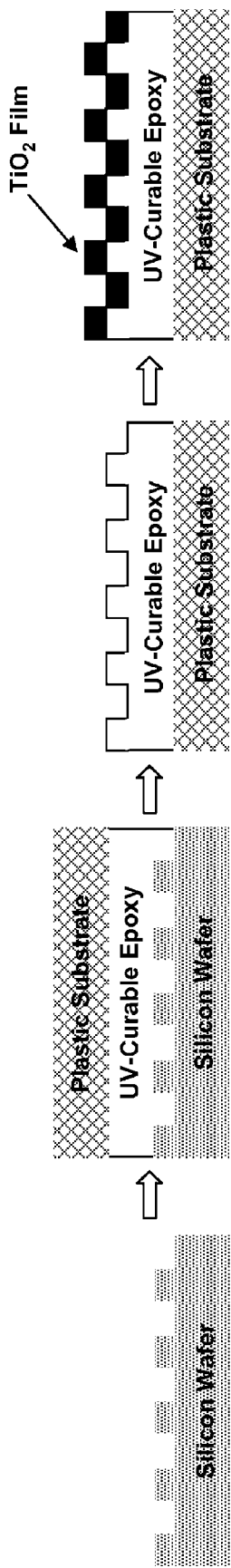

Fig. 18
a)
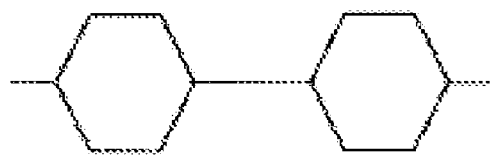
b)
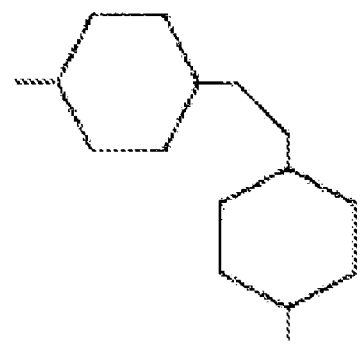

Fig. 23
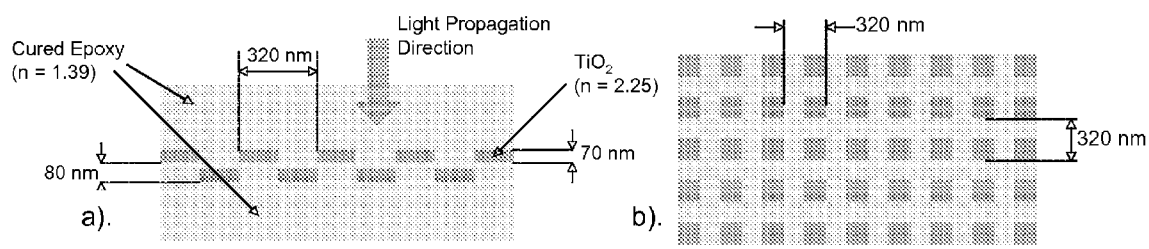
a). b).
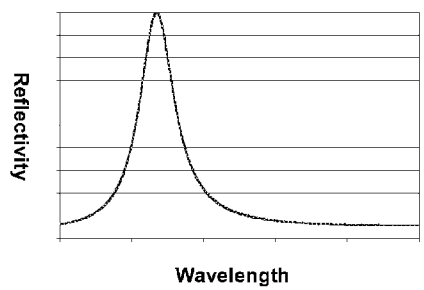
Wavelength
Fig. 24
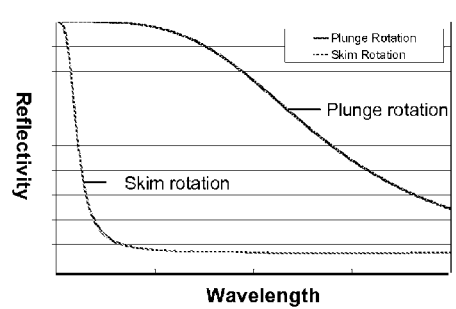
Wavelength
Fig. 25

Fig. 26
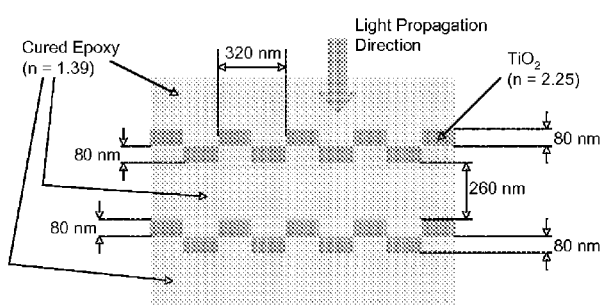
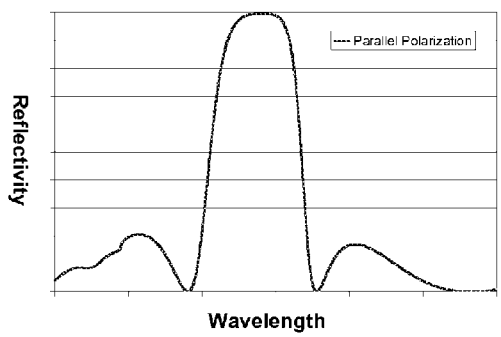
Fig. 27
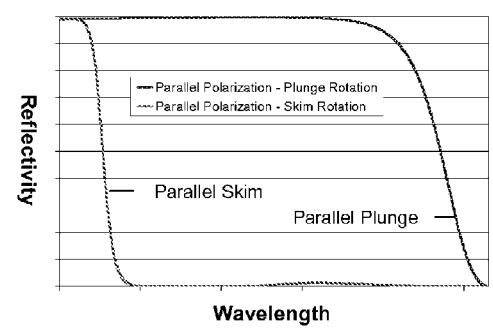
Fig. 28

Fig. 29
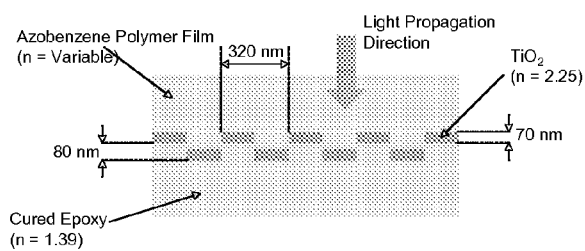
Left panel
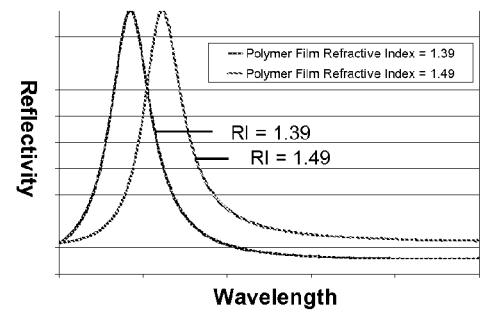
Right panel

PASSIVE AND ACTIVE PHOTONIC CRYSTAL STRUCTURES AND DEVICES

CROSS REFERENCE TO RELATED APPLICATIONS

This application claims priority under 35 U.S.C. 119(e) to U.S. provisional Patent Application 60/782,565 filed Mar. 15, 2006, which is hereby incorporated by reference in its entirety.

STATEMENT REGARDING FEDERALLY SPONSORED RESEARCH OR DEVELOPMENT

This invention was made with United States government support awarded by Battelle under contract number TCN 04174, a subcontract under the U.S. Army Research Office contract DAAD19-02-D-0001.

BACKGROUND OF THE INVENTION

Photonic crystals, also commonly referred to as photonic bandgap structures, are periodic dielectric or metallic structures exhibiting a spatially periodic variation in refractive index that forbids propagation of certain frequencies of incident electromagnetic radiation. The photonic band gap of a photonic crystal refers to the range of frequencies of electromagnetic radiation for which propagation through the structure is prevented. The photonic band gap phenomenon may be conceptualized as complete reflection of incident electromagnetic radiation having selected frequencies and propagating in certain directions due to interaction with the periodic structural domains of a photonic crystal. The spatial arrangement and refractive indices of these structural domains generate photonic bands gaps that inhibit propagation of electromagnetic radiation centered about a particular frequency.

Photonic crystals provide an electromagnetic analog to electron-wave behavior observed in crystals wherein electron-wave concepts, such as dispersion relations, Bloch wave functions, van Hove singularities and tunneling, having electromagnetic counterparts in photonic crystals. In semiconductor crystals, for example, an electronic band gap of energy states for which electrons are forbidden results from a periodic atomic crystalline structure. By analogy, in a photonic crystal, a photonic band gap of forbidden energies (or wavelengths/frequencies) of electromagnetic radiation results from a periodic structure of a dielectric material where the periodicity is of a distance suitable to interact with incident electromagnetic radiation of a selected wavelength.

Selection of the physical dimensions, refractive indices and spatial distribution of structural domains of a photonic crystal provides an effective means of designing a photonic crystal having a photonic band gap with a selected frequency distribution. One-dimensional, two-dimensional and three-dimensional photonic crystals have been fabricated providing complete or at least partial photonic bands having selected frequency distributions gaps in one or more directions. Photonic crystals have also been fabricated having selected local disruptions (e.g., missing or differently-shaped portions of the structural domains of periodic array) in their periodic structure, thereby generating defect or cavity modes with frequencies within a forbidden bandgap of the crystal. Photonic crystals having specific defects are of particular interest because they provide optical properties useful for controlling and manipulating electromagnetic radiation, such as the ability to provide optical confinement and/or wave guiding with very little, or essentially no, radiative losses.

As diffraction and optical interference processes give rise to the photonic band gap phenomenon, the periodicity of photonic crystal structures is typically on the order of the wavelength of incident electromagnetic radiation. Accordingly, photonic crystals for controlling and manipulating visible and ultraviolet electromagnetic radiation typically comprise dielectric or metallic structures with periodic structural domains having submicron physical dimensions on the order of 100 s nanometers. A number of fabrication pathways for making periodic structures having these physical dimensions have been developed over the last decade, including micromachining and nanomachining techniques (e.g., lithographic patterning and dry/wet etching, electrochemical processing etc.), colloidal self assembly, layer-by-layer assembly and interference lithography. Advances in these fabrication techniques have enabled fabrication of one-dimensional, two-dimensional and three-dimensional photonic crystals from a range of materials including dielectric crystals, metallic, polymeric and colloidal materials.

The structure, composition, fabrication and optical properties of photonic crystals are described in the following references which are hereby incorporate by reference in their entireties: (1) Joanopoulus et al., "Photonic Crystals Molding the Flow of Light", Princeton University Press, 1995; (2) A. Birner, R. B. Wehrspohn, U. M. Gösele, K. Busch, "Silicon-Based Photonic Crystals", Advanced Materials, Volume 13, Issue 6, Pages 377-388; and (3) Steven G. Johnson, and John D. Joannopoulos, "Photonic Crystals: The Road from Theory to Practice", Springer, 2002.

Given recent advances in their fabrication and their unique optical properties, photonic crystals are identified as key components for realizing a new generation of high performance, low loss optical and electro-optic devices. As an alternative to semiconductor technologies, photonic crystals have great potential to provide a promising pathway to a range of smaller, faster and more energy efficient devices that perform the same functionality as their silicon-based counterparts. Accordingly, photonic crystals have the potential to revolutionize a number of technologies ranging from optical computing, dense wavelength division multiplexing, light emitting systems and biosensing. A number of passive photonic devices have been fabricated taking advantage of the complete and partial photonic band gap(s) provided by photonic crystals, including optical filters, beam splitters, waveguides, channel drop filters and resonance cavities.

Photonic crystals also have great potential as components in active photonic devices, such as solid state lasers, optical switches, optical diodes and optical transistors. To expand their functionality, role and applicability in active photonic device configurations, substantial research is currently being directed at developing photonic crystal structures and systems providing a selectively tunable photonic band gap. Tunability in this context refers to the ability to selectively change the range of frequencies corresponding to a photonic band gap of a photonic crystal. The ability to dynamically control (i.e., selectively tune) the frequency range of a photonic band gap on a fast time scale (e.g. milliseconds or less) would potentially enable optical switches and transistors for a range of important applications including optical signal processing in telecommunications, all-optical integrated circuits, all-optical computing applications and information storage. A number of approaches for providing photonic crystals with tunable photonic band gaps have been pursued including: (i) incorporation of nematic liquid crystal materials and/or conducting organic polymers responsive to applied electric fields into the periodic dielectric structures of photon crystals; (ii) colloidal photonic crystals comprising thermo- or electroresponsive hydrogel nanoparticles; (iii) use of flexible, expandable and/or compressible photonic crystals capable of changing periodicity upon application of mechanical stress; and (iv) coupled photonic crystal systems having a mechanically tunable air separation layer. While these approaches have met with some degree of success, tunable photonic crystals currently do not exhibit the high level of performance (e.g., fast modulation rate, high optical throughput and low loss) required for many applications and typically involve expensive fabrication pathways that are not generally amenable to low cost, mass production and commercialization.

Given their great potential for active and passive components in a range of useful devices, it will be appreciated that there is currently a need for new photonic crystal based devices, systems and instrumentation. It will also be appreciated from the foregoing that a need exists for high performance tunable photonic crystals capable of fast optical modulation and compatible with commercially practicable fabrication methods.

SUMMARY OF THE INVENTION

The present invention provides active and passive photonic devices, device components and systems having photonic crystals for optical modulating, filtering and/or switching functionality. Optical filtering and/or shielding devices, device components and methods are provided that are capable of preventing transmission of electromagnetic radiation of selected frequencies, polarization states, energies and incident angles, while allowing for efficient transmission of electromagnetic radiation at other frequencies. Optical filtering and/or shielding devices, device components and methods of the present invention are capable of preventing transmission of electromagnetic radiation having selected frequencies in the ultraviolet, visible and/or infrared regions, particularly those frequencies corresponding to common laser sources and laser modes. Photonic crystals having a photonic band gap with a tunable frequency distribution are provided that are particularly useful for optical modulating the intensity of an input optical beam. The present invention provides polymer based photonic crystals and photonic crystal based devices that are capable of manufacture via a simple, inexpensive and high-throughput fabrication pathway.

In one aspect, the present invention provides a device for protecting an eye, or other optical sensor, from incident laser electromagnetic radiation using a two dimensional photonic crystal having a photonic band gap with a frequency distribution that at least partially overlaps the frequency distribution of incident electromagnetic radiation for a laser source. One device of this aspect of the present invention comprises a photonic crystal having a spatial distribution of refractive indices that varies periodically in at least two dimensions and positioned to intersect electromagnetic radiation generated by a laser source, including electromagnetic radiation having normal and non-normal incident angles with respect to a receiving surface of the photonic crystal. The photonic crystal comprises a dielectric structure comprising alternating high refractive index elements and low refractive index elements provided in a periodic spatial configuration in at least two dimensions. The spatial distribution of refractive indices of the photonic crystal and/or the refractive indices of the high and the low refractive index layers are selected such that the photonic band gap of the photonic crystal at least partially overlaps the range of frequencies of the laser electromagnetic radiation.

For applications such as protecting a person's eyes against damage caused by laser electromagnetic radiation, the spatial distribution of refractive indices of the photonic crystal and/or the refractive indices of the high and the low refractive index layers are selected such that the photonic band gap of the photonic crystal completely overlaps at least a portion of the range of frequencies of on the radiant output of one or more laser sources and thus, substantially prevents transmission (i.e. reflects and/or scatters) of substantially all incident laser electromagnetic radiation (e.g. at least about 95%, and preferably for some application at least about 99%). For the case of when the laser wavelength perfectly matches the wavelength of highest reflection from the photonic crystal, calculations show 100% reflection is theoretically possible.

In an embodiment, the dielectric structure comprises high refractive index elements and low refractive index elements provided in a spatial configuration that is periodic in at least two lateral directions, wherein the lateral directions are not parallel to the propagation axes of the electromagnetic radiation from the laser. In an embodiment, the dielectric structure comprises high refractive index elements and low refractive index elements provided in a spatial configuration that is periodic in at least two lateral directions, wherein the lateral directions are orthogonal to the propagation axes of the electromagnetic radiation from the laser. In an embodiment, the laser provides a beam of electromagnetic radiation that is incident upon a receiving surface of the photonic crystal; and the dielectric structure comprises high refractive index elements and low refractive index elements provided in a spatial configuration that is periodic in at least two lateral directions, wherein the lateral directions are parallel to the receiving surface.

In an embodiment, the dielectric structure of the photonic crystal comprises a two-dimensional or three dimensional periodic array of alternating high refractive index elements and low refractive index elements. High refractive index elements and low refractive index elements may comprise any type of material having beneficial optical properties (e.g., refractive indices, extinction coefficients, etc.), mechanical properties (e.g., Young's modulus, structural rigidity etc.) and electro-optical properties, including polymer materials, ceramics, thin dielectric films, thin semiconductor films, metals, glasses, and colloids. In some example embodiments, high refractive index structural elements have a refractive index that is at least 1.2 times larger than the low refractive index elements. In an embodiment, for example, low refractive index elements comprise features of a nanostructured substrate having a refractive index of about 1.47 and high refractive index elements comprise $TiO_2$ thin films having a refractive index of about 1.77, which is at the low end of the commonly observed range for $TiO_2$). In embodiments providing active photonic device behavior, high refractive index elements or low refractive index elements of the periodic array comprise a photodynamic material such as a photodynamic polymer comprising a dye, such as an azobenzene dye, embedded in a polymer matrix that is capable of undergoing a change in refractive index upon exposure to excitation electromagnetic radiation. Exemplary azobenzene dyes for use in dynamic photonic crystals of the present invention include N-ethyl-N-(2-hydroxyethyl), which is commonly referred to as Dispersed Red 1 or DR1.

In an embodiment of the present invention useful for providing laser protection eyewear and optical shielding elements (e.g. windows), devices of this aspect of the present invention further comprise a substrate having alternating raised and recessed relief features provided in a periodic spatial configuration. The high refractive index elements, such as thin dielectric films, are disposed on top of the raised and recessed relief features of the substrate and at least a portion of the low refractive index elements are raised features of the substrate itself. The pattern of raised and recess features of the substrate of this embodiment, therefore, functions to structurally support the high refractive index elements and to provide a desired at least two dimensional array of high refractive index elements and low refractive index elements. Optionally, devices of this aspect of the present invention further comprises a superstrate having alternating raised and recessed relief features provided in a periodic spatial configuration. In one useful embodiment, the periodic spatial configuration of the superstrate corresponds to the reverse pattern of the periodic spatial configuration of the substrate such that raised and recessed regions of the superstrate line up with recessed and raised regions of substrate, respectively. In this embodiment, the superstrate is positioned such that it is in contact with at least a portion of the high refractive index elements, and at least a portion of the low refractive index elements comprise raised relief features of the superstrate itself. Incorporation of substrates and/or superstrates into the devices of the present invention, particularly polymeric substrates and substrates, is beneficial because it provides an effective means of mechanically shielding, enclosing and/or protecting high and low refractive index elements of the photonic crystal from damage arising from exposure to ambient conditions. This aspect of the present invention is very useful for providing mechanically robust and durable devices that may be used reliably in a range of field settings. Use of patterned polymeric substrates also enables fabrication of two-dimensional photonic crystals having large areas and/or two-dimensional photonic crystals having contoured configurations, such as curved photonic crystals having a curvature similar to that of a human eye. In some example embodiments, the upper limit to area is determined by the area of the silicon wafer master that is used to fabricate the array of high refractive index elements and low refractive index elements. Silicon wafer masters having a diameter at large as 300 mm (corresponding to an area of 706 cm$^2$) are useful in the present invention.

In one embodiment of this aspect of the present invention, for example, the substrate and/or superstrate (and, hence, low refractive index elements) comprise polymeric materials, and the high refractive elements comprise thin dielectric films deposited on the raised and recessed relief features the substrate and/or superstrate. Optionally, thin dielectric films are also provided on the side walls of the raised and recessed relief features the substrate and/or superstrate. Polymeric materials useful in this aspect of the present invention have a refractive index selected from the range of about 1.39 to about 1.47, and include at least partially optically transparent thermoplastics such as polymethylmethacrylate. Thin dielectric films useful in this aspect of the present invention have a refractive index selected from the range of about 1.75 to about 2.5, having thickness selected from the range of about 60 nanometers to about 180 nanometers, and include metal oxide films, such as $TiO_2$.

Two dimensional photonic crystals of this aspect of the present invention may be an integrated functional component of a device for preventing transmission of laser light into a user's eye or onto sensor instrumentation, such as eyewear or a window positioned between the user's eyes (or a sensor) and a source of laser electromagnetic radiation. In one embodiment, for example, the photonic crystal provides an optical shield for a pair of eyeglasses, a visor, goggles, a hood, face mask or a helmet. In another embodiment, the photonic crystal provides an optical filter for windows of a plane, automobile, boat or other means of transportation. In yet another embodiment, the photonic crystal provides an optical shield for protecting a sensor used in laser guidance or infrared guidance systems from incident laser electromagnetic radiation. Device configurations of photonic crystals of the present invention may have a receiving surface having a planar or contoured shape for receiving incident laser electromagnetic radiation. Contoured photonic crystals may have any nonplanar shape including, curved, rounded, bowed convex, concaved or any combination of these shapes. In an exemplary embodiment, for example, a curved photonic crystal provides an optical filtering element of eyewear capable of protecting eyes from laser electromagnetic radiation. In an embodiment useful for providing enhanced reflection of laser electromagnetic radiation of non-normal incident angles, a photonic crystal having a curved receiving surface is provided having a curvature substantially similar to that of a human eye (i.e. radii of curvature that are within about 5% of each other, and preferably for some applications radii of curvature that are within about 1% of each other). Use of curved photonic crystals for optical filtering is useful for ensuring that the angle of incidence of the incident beam is within the range of angles corresponding to the photonic band gap.

A functional feature of the present invention particularly attractive for these device applications is that the present photonic crystals are capable of substantially preventing (i.e., percentage of transmission less than or equal to about 5%, and preferably for some applications percentage of transmission less than or equal to about 1%) transmission of electromagnetic radiation having frequencies corresponding to the radiant output of a laser (e.g, one or more laser lines/modes), while at the same time efficiently transmitting (i.e., percentage of transmission greater than or equal to about 80%, and preferably for some applications percentage of transmission greater than or equal to about 90%) the range of electromagnetic radiation in the visible region of the electromagnetic spectrum having frequencies that are different than that of the incident laser electromagnetic radiation. A user or sensor protected by the present devices, therefore, is able detect these transmitted frequencies of light, thereby enabling a user to see clearly through the photonic crystal device or allowing a sensor to detect the transmitted electromagnetic radiation.

In another embodiment, the present device for protecting an eye, or other optical sensor, from incident laser electromagnetic radiation comprises a plurality of photonic crystals positioned in optical communication with each other and positioned to intersect the electromagnetic radiation generated by a laser. In this embodiment, the photonic crystals have a spatial distribution of refractive indices that varies periodically in at least two dimensions such that they are capable of substantially preventing transmission of laser electromagnetic radiation having selected frequency distributions. Photonic crystals in this configuration have photonic band gaps which may be optically coupled or optically isolated, and may have a photonic bandgap with the same frequency distribution or may have photonic bandgaps with different frequency distributions.

The present invention also provides devices comprising a plurality of photonic crystals provided in a stacked optical configuration such that incident laser electromagnetic radiation interacts with the photonic crystals in the stack sequentially. Adjacent photonic crystals are separated by a separation layer or other optical alignment system, providing a substantially constant (i.e. with in 5%) or selectively variable optical pathlength between adjacent photonic crystals. Use of a separation layer comprising a polymeric material provides a mechanically robust and readily fabricated means of coupling adjacent photonic crystals. Use of two or more of photonic crystals in devices of the present invention provides functional benefits useful for prevent transmission of electromagnetic radiation laser sources, such as providing devices having a photonic band gap with a selectively modified frequency distribution capable of providing very efficient optical filtering and/or providing devices capable of preventing transmission of at least a portion of the electromagnetic radiation corresponding to the radiant output of one or more laser sources.

In an embodiment of this aspect of the present invention, two or more photonic crystals having substantially the same two-dimensional, periodic spatial distribution of refractive indices are positioned in a stacked configuration. Adjacent photonic crystals are separated by a separation layer and spaced close enough to each other such that optical coupling between adjacent photonic crystals provides a net photonic band gap with a modified frequency distribution, such as a frequency distribution having a "flat-top frequency profile" (i.e. a frequency distribution that approximates a square-wave function), and provides enhanced performance (e.g., reflectivity) for laser electromagnetic radiation propagating along non-normal incident angles. Use of optically coupled photonic crystals having a flat top frequency profile is beneficial for some optical filtering embodiments, as this frequency profile provides high reflection efficiencies (e.g. <95%) over a significant span of frequencies for a wide range of incident angles.

In another embodiment, two or more photonic crystals having different two-dimensional, periodic spatial distributions of refractive indices and thus, different photonic band gap frequency distributions, are positioned sequentially in a stacked configuration. In some embodiments, adjacent photonic crystals are separated by a separation layer and positioned far enough from each other such that they are substantially optically isolated from each other. The spatial distributions of refractive indices in this embodiment are selected such that each photonic crystal in the stack is capable of preventing transmission of electromagnetic radiation from a different laser source, laser line, laser band or laser mode. This multi-photonic crystal stack embodiment, therefore, is capable of simultaneously preventing transmission of a plurality of different laser lines and, thus, provide enhanced protection for an eye or a sensor.

In another embodiment, at least two photonic crystals are provided in a stacked configuration, wherein different photonic crystal are positioned such that their principal optical axis are offset relative to each other. In one embodiment, for example, a device of the present invention comprises two stacked photonic crystals oriented such that their principal optical axes are off set by about 45 degrees. In another embodiment, a device of the present invention comprises four stacked photonic crystals oriented such that their principal optical axes are sequentially off set by about 22.5 degrees. Devices of this aspect of the present invention provide enhanced performance (i.e. reflectivity) for preventing transmission of incident electromagnetic radiation over a wider range of polarization states.

The present invention also provides active photonic devices providing dynamic optical filtering of incident laser electromagnetic radiation. In one embodiment, for example, one or more dynamic photonic crystals are provided having low refractive index elements, high refractive index elements or both comprising a photodynamic polymer exhibiting a selectively variable refractive index that changes upon exposure to electromagnetic radiation generated by a laser. Dynamic photonic crystals comprising photodynamic polymers are useful in the present invention because they provide a photonic band gap having a selectively variable frequency distribution. Useful photodynamic polymer materials for this aspect of the present invention include dye materials embedded in a polymer matrix, such as azobenzene dye materials that exhibit relatively large ($\Delta n > 0.01$) and rapid (i.e. millisecond, microsecond or nanosecond time scales) changes in refractive index upon exposure to polarized electromagnetic radiation. In one embodiment, a device of the present invention comprises at least one static photonic crystal having a band gap with a substantially constant (i.e. within 5%) frequency distribution in combination with at least one dynamic photonic crystal having a band gap with a selectively variable frequency distribution. The periodic distributions of high and low dielectric elements of static and dynamic photonic crystals are selected such that the frequency distributions of their band gaps overlap when the device is not exposed to laser electromagnetic radiation. When illuminated by laser electromagnetic radiation, however, the dynamic photonic crystal(s) in the device undergoes a change in its periodic distribution of high and low dielectric elements (e.g., the refractive indices of high refractive index elements, low refractive index elements or both changes) causing the frequency distribution of the photonic band gap to shift away from the frequency distribution of the photonic band gaps of the static photonic crystals. The combination of optical filtering provided by the static photonic crystal(s) and dynamic photonic crystal(s), therefore, enhances the range of frequencies that transmission is prevented upon interaction of the device with laser electromagnetic radiation.

In another aspect the present invention provides dynamic photonic crystals having a tunable photonic band gap. In the context of this description, "tunable photonic band gap" refers to a photonic band gap having a selectively variable frequency distribution. Tunable photonic band gaps of the present invention may have a center frequency (i.e. maximum in reflection spectrum) that can be continuously tuned (or adjusted) over a given frequency range or a center frequency that can be discretely tuned (or adjusted) to selected frequencies over a given frequency range. The present invention provides dynamic photonic crystals wherein the center frequency of a tunable band gap changes upon exposure to polarized excitation electromagnetic radiation by more than 15 nanometers, and more preferably for some applications changes as much as 100 nanometers. Tunable photonic crystals of the present invention may comprise functional components in a variety of active photonic devices and systems, including optical switches, optical transistors, optical diodes, dense wavelength multiplexing systems and light emitting systems, such as lasers and LED based optical sources.

In one embodiment, a dynamic photonic crystal having a tunable photonic band gap comprises a dielectric structure having a spatial distribution of refractive indices that varies periodically in at least one dimension (e.g., one-dimensional, two-dimensional or three dimensional photonic crystal). In this embodiment, the dielectric structure comprises alternating high refractive index elements and low refractive index elements provided in a periodic spatial configuration. To provide tunability with respect to the photonic band gap, low refractive index elements, high refractive index elements or both of this aspect of the present invention comprise a photodynamic material, such as a polymer exhibiting a selectively variable refractive index that changes upon exposure to polarized electromagnetic radiation, such a linearly polarized light from a laser source. Dielectric structures useful in this aspect of the present invention include one-dimensional periodic arrays of high refractive index elements and low refractive index elements, two-dimensional periodic arrays of high refractive index elements and low refractive index elements, and three-dimensional periodic arrays of high refractive index elements and low refractive index elements. In embodiments of the present invention useful for optical filtering applications, the periodic spatial configuration of the dielectric structure has a non-varying period in one or more dimensions.

In the context of this description, the term "photodynamic polymer" refers to polymeric materials that are responsive to electromagnetic radiation, such that they undergo a change in refractive index upon exposure to linearly polarized electromagnetic radiation. The response of exemplary photodynamic materials to polarized electromagnetic radiation is preferably rapid (i.e. occurring on millisecond, microsecond or nanosecond time scales) for some applications and is, optionally, dependent on the radiant power, wavelength and polarization state of the polarized excitation radiation. Some useful photodynamic materials also exhibit an accompanying increase or decrease in birefringence upon exposure to polarized electromagnetic radiation. A class of photodynamic polymers useful for dynamic photonic crystals of the present invention comprises a dye material, such as a nonlinear dye, embedded in a polymer matrix. Exemplary photodynamic polymer materials useful in embodiments of the present invention included, but are not limited to, azobenzene dyes, such as N-ethyl-N-(2-hydroxyethyl) 4 (4 nitrophenylazo)aniline, 4-(dimethylamino)azobenzene (also known as Dimethyl Yellow), and 2-(4 Dimethylaminophenylazo) benzoic acid (also known as Methyl Red), embedded in a polymer matrix, such as a thermoplastic, elastomer, thermosets and composite polymer materials. Azobenzene dyes are particularly attractive for use in the present invention because they are capable of providing large changes in refractive index (e.g. greater than about 0.01) for relatively low illumination intensities (e.g. less than about 10 Watts $cm^{-2}$). Other exemplary nonlinear dye materials useful in the present methods devices, compositions, and devices, include, but are not limited to, (2,6-Dimethyl-4H-pyran-4-ylidene)malononitrile; (S)-(−)-1-(4-Nitrophenyl)-2-pyrrolidinemethanol; [4-[Bis(2-hydroxyethyl)amino]phenyl]-1,1,2-ethylenetricarbonitrile; 1-Docosyl-4-(4-hydroxystyryl)pyridinium bromide; 2-(Dimethylamino)vinyl-1-nitronaphthalene; 2,3,5,6-Tetrafluoro-7,7,8,8-tetracyanoquinodimethane; 2-[[5-(Dibutylamino)-2-thienyl]methylene]-1H-indene-1,3(2H)-di one; 2-[4-((4-(Bis(2-hydroxyethyl)amino]phenyl)(cyano)methylene]-2,5-cyclohexadien-1-ylidene]malonitrile; 2-[4-(Dimethylamino)styryl]pyridine; 2-[Ethyl[4-[2-(4-nitrophenyl)ethenyl]phenyl]amino]ethanol; 2-Amino-3-nitropyridine; 2-Amino-5-nitropyridine; 2-Aminofluorene; 2-Chloro-3,5-dinitropyridine; 2-Chloro-4-nitroaniline; 2-Nitroaniline; 3-[(4-Nitrophenyl)azo]-9H-carbazole-9-ethanol; 3-Methyl-4-nitropyridine N-oxide; 3-Nitroaniline; 4-(Dibenzylamino)benzaldehyde-N,N-diphenylhydrazone; 4-[4-(Dimethylamino)styryl]-1-docosylpyridinium bromide; 4-[4-(Dimethylamino)styryl]pyridine; 4-Dimethylamino-4'-nitrostilbene; 4-Nitroaniline; 5-Nitroindole; 5-Nitrouracil; 7,7,8,8-Tetracyanoquinodimethane; 9-Ethyl-3-carbazolecarboxaldehyde-N-methyl-N-phenylhydrazone; 3-[N-Ethyl-4-(4-nitrophenylazo)phenylamino]propionitrile (Disperse Orange 25); 4-(4-Nitrophenylazo)aniline (Disperse Orange 3); N-Ethyl-N-(2-hydroxyethyl)-4-(4-nitrophenylazo) aniline (Disperse Red 1); 2-[4-(2-Chloro-4-nitrophenylazo)-N-ethylphenylamino]ethanol (Disperse Red 13); Disperse Red 19; 4-[4-(Phenylazo)phenylazo]-o-cresol (Disperse Yellow 7); Ethyl 4-(dimethylamino)benzoate; Hexamethylpararosaniline chloride (Crystal Violet); N-(2,4-Dinitrophenyl)-L-alanine methyl ester; N,N-Dimethyl-N'-[(5-nitro-2-thienyl)methylene]-1,4-phenylenediamine; N-[3-Cyano-3-[4-(dicyanomethyl)phenyl]-2-propenylidene]-N-ethyl-ethaniminium; Nile Blue A (Basic Blue 12); N-Methyl-4-nitroaniline; trans-4-[4-(Dimethylamino)styryl]-1-methylpyridinium iodide; and trans-4-[4-(Dimethylamino)styryl]-1-methylpyridinium p-toluenesulfonate.

Useful photodynamic materials capable of providing large changes in refractive index (e.g. greater than 0.01) comprise about 1% to about 10% by mass of the embedded dye material, such as an embedded azobenzene dye. The mechanism by which these materials change refractive index may include induced transitions between energy states, such as a transition from a lower energy trans-state to an excited cis-state, and radiatively induced large-scale alignment along a direction perpendicular to the polarization of the excitation electromagnetic radiation.

In an embodiment, a dynamic photonic crystal of the present invention further comprises a substrate having a periodic one-dimensional or two-dimensional pattern of raised and recessed relief features, and a superstrate having a periodic one-dimensional or two-dimensional pattern of raised and recessed relief features. At least a portion of the substrate, superstrate or both comprise a photodynamic material such as a photodynamic polymeric material (e.g, such as an azobenzene dye embedded in a polymer matrix). In this embodiment, high refractive index elements of the dielectric structure comprise thin dielectric films, such as $TiO_2$, that are disposed on top of, and optionally on the sides of, the raised and recessed features of the substrate. The pattern of raised and recess features of the substrate of this embodiment, therefore, functions to support the high refractive index elements and defines the one- or two-dimensional array of high refractive index elements and low refractive index elements. The periodic spatial configuration of the superstrate, on the other hand, corresponds to the reverse pattern of the periodic spatial configuration of the substrate such that raised and recessed regions of the superstrate line up with recessed and raised regions of substrate, respectively. In this embodiment of the present invention, low refractive index elements comprise raised features of the substrate, superstrate or both of these device components. As discussed above in the context of devices for preventing transmission of laser electromagnetic radiation, incorporation of polymeric substrates and superstrates in photonic crystals of the present invention provides an effective means of protecting these elements from degradation or modification caused by exposure to ambient environments and enhancing their structural robustness.

To provide photodynamic behavior, the tunable photonic crystal is illuminated with polarized electromagnetic radiation having frequencies that are at least partially absorbed by the photodynamic polymer, such as linearly polarized electromagnetic radiation. In a useful embodiment, illumination of the tunable photonic crystal is carried out using a laser optical source at a laser line resonant with one or more absorption peaks of the optically active component of the photodynamic polymer. Exposure to the excitation polarized electromagnetic radiation causes the refractive index of the photodynamic polymer materials to change (i.e. increase or decrease), thereby causing a change in the one, two or three dimensional periodic spatial distribution of refractive indices of the photonic crystal. The change in the periodic spatial distribution of refractive indices results in an accompanying change (or shift) in the frequency distribution of the photonic band gap of the crystal. Modulation of the frequency distribution of the photonic band gap is carried out, therefore, by illuminating the dynamic photonic crystal at selected time intervals and/or using selective variation of the power, frequency or polarization state of the excitation polarized electromagnetic radiation provided to the dynamic photonic crystal. In some embodiments, the extent of the change (or shift) in the frequency distribution of the photonic band gap varies as a function of radiant power of the excitation polarized electromagnetic radiation. Exemplary radiant powers useful for this aspect of the present invention range from about 5 mW to about 1000 mW for a 3 mm beam spot diameter (i.e. a power per area selected over the range of 0.7 mW mm$^{-2}$ to about 140 mW mm$^{-2}$).

In another aspect, the present invention provides an optical switching device for optical modulating the intensity of one or more input optical beams of electromagnetic radiation, such as one or more optical data beams. Switching devices of this aspect of the present invention are provided with a dynamic photonic crystal, as described above, with a tunable photonic band gap having a selectively variable frequency distribution, and an excitation optical source. The dynamic photonic crystal is positioned to receive one or more input optical beams of electromagnetic radiation and is positioned in optical communication with the excitation optical source. The excitation optical source is capable of illuminating the dynamic photonic crystal with an excitation beam of linearly polarized electromagnetic radiation. In one embodiment, the dynamic photonic crystal has a receiving surface for receiving the incident input optical beam at substantially (within 90%) normal incidence and the excitation optical source is capable of providing a beam of polarized electromagnetic radiation at non-normal incident angles relative to the receiving surface of the photonic crystal. Preferably for some applications the dynamic photonic crystals are positioned such that the input optical beam and the excitation beam of polarized electromagnetic radiation substantially overlap in the crystal (i.e. overlap to within 1%). Useful input optical beams for the devices and methods of this aspect of the present invention include narrow band and broad band beams having a polarization state that is substantially perpendicular to the grating lines of the photonic crystal. Polarized electromagnetic radiation from laser sources (pulsed or continuous) is useful as excitation sources in this aspect of the present invention, particularly laser electromagnetic radiation having a frequency that is significantly absorbed (i.e. extinction coefficient >$10^6$ m$^{-1}$) by optically active components of the photodynamic polymer. Excitation optical sources useful in the present invention include, but are not limited to, a laser or light emitting diode optical source.

To provide optical modulation, the photonic crystal is exposed to the excitation linearly polarized electromagnetic radiation at selected time intervals. In addition, the radiant power of the excitation polarized electromagnetic radiation is optionally varied selectively with respect to time. Modulation of the intensity of the input optical beam is provided by selectively changing transmission of incident electromagnetic radiation through the photonic crystal provided by exposure of the crystal to electromagnetic radiation. The intensity of the input optical beam can be continuously modulated or may be modulated between discrete intensity values (e.g. on-off modulation).

In one embodiment, the periodic spatial configuration of alternating high refractive index elements and low refractive index elements of the dynamic photonic crystal is selected such that the exposure of the photonic crystal to the excitation beam of polarized electromagnetic radiation shifts the frequency distribution of the photonic band gap such that it does not significantly overlap with the frequency distribution of the input optical beam. In this crystal configuration exposure to the polarized excitation electromagnetic radiation initiates a transition from an "off state", wherein transmission of the input beam is substantially prevented, to an "on state", wherein at least a portion of the input optical beam of electromagnetic radiation is transmitted through the photonic crystal.

In another embodiment, the periodic spatial configuration of alternating high refractive index elements and low refractive index elements of the dynamic photonic crystal is selected such that the exposure of the photonic crystal to the excitation beam of polarized electromagnetic radiation shifts the frequency distribution of the photonic band gap such that it does significantly overlap with the frequency distribution of the input optical beam. In this crystal configuration exposure to the polarized excitation electromagnetic radiation initiates a transition from an "on state" wherein the input beam is at least partially transmitted through the photonic crystal to an "off state" wherein transmission of the input optical beam of electromagnetic radiation is substantially prevented.

Use of a dynamic photodynamic crystal having a relatively narrow photonic band gap (e.g. full width at half maximum less than about 0.2 nanometers) is particularly beneficial for certain device applications of optical switching devices of the present invention because only a small shift in the frequency distribution of the photonic bandgap is needed to enable a complete transition from an "on state" to an "off state" or a complete transition from "an off state" to an "on state". Some optical switching devices of the present invention incorporate a one-dimensional dynamic photonic crystal having a one-dimensional periodic distribution of refractive indices, which is useful for accessing tunable photonic band gaps having a narrow frequency distribution. Use of substrates and superstrates having substantially the same refractive index (i.e. within 2%) is also useful for providing photonic crystals having a narrow, tunable photonic band gap. The present invention includes embodiments, wherein the substrate and superstrate of the dynamic photonic crystal comprise the same photodynamic material, such as a nonlinear dye (e.g., azobenzene dye) embedded in a polymer matrix.

Use of photodynamic materials that respond to exposure to excitation polarized electromagnetic radiation on microsecond or nanosecond timescales is beneficial for some high performance optical switching applications. Exemplary materials providing substantial changes in refractive index (i.e. greater than about 0.001) on such rapid time scales upon exposure to polarized excitation radiant powers selected over the range from about 5 mW to about 1000 mW for a 3 mm beam spot diameter (i.e. a power per area selected over the range of 0.7 mW mm$^{-2}$ to about 140 mW mm$^{-2}$) include azobenzene dyes, such as N-ethyl-N-(2-hydroxyethyl) 4 (4 nitrophenylazo)aniline, embedded in a polymer matrix, such as a polymethylmethacrylate matrix. Rapid changes in refractive index may be provided by azobenzene dye materials that undergo a transition from a lower energy trans-state to a higher energy cis-state upon exposure to polarized excitation electromagnetic radiation radiation.

In another aspect the present invention provides a method for tuning the frequency distribution of a photonic band gap of a photonic crystal comprising the steps of: (1) providing the photonic crystal comprising a dielectric structure having a spatial distribution of refractive indices that varies periodically in at least one dimension, the dielectric structure comprising alternating high refractive index elements and low refractive index elements provided in a periodic spatial configuration; the low refractive index elements or the high refractive index elements comprising a photodynamic polymer exhibiting a selectively variable refractive index that changes upon exposure to polarized electromagnetic radiation; and (2) exposing the photonic crystal to polarized electromagnetic radiation, thereby changing the refractive index of the low refractive index elements or the high refractive index elements and tuning the frequency distribution of a photonic band gap of the photonic crystal.

In another aspect, the present invention provides a method for modulating the intensity of an input optical beam having a frequency distribution comprising the steps of: (1) directing the input optical beam onto a photonic crystal having a photonic band gap with a tunable frequency distribution comprising a dielectric structure having a spatial distribution of refractive indices that varies periodically in at least one dimension, the dielectric structure comprising alternating high refractive index elements and low refractive index elements provided in a periodic spatial configuration; the low refractive index elements or the high refractive index elements comprising a photodynamic polymer exhibiting a selectively variable refractive index that changes upon exposure to an excitation a beam of polarized electromagnetic radiation; and (2) changing the frequency distribution of the photonic band gap of the photonic crystal by exposing the photonic crystal to the excitation a beam of polarized electromagnetic radiation, thereby modulating the intensity of the input optical beam. Optionally, the periodic spatial configuration of alternating high refractive index elements and low refractive index elements of the dynamic photonic crystal is selected such that exposure of the photonic crystal to the excitation beam of polarized electromagnetic radiation changes the frequency distribution of the photonic band gap from a frequency distribution that significantly overlaps the distribution of wavelengths of the input optical beam to a frequency distribution that does not significantly overlap the distribution of wavelengths of the input optical beam, thereby allowing transmission of the input optical beam of electromagnetic radiation through the photonic crystal. Optionally, the periodic spatial configuration of alternating high refractive index elements and low refractive index elements of the dynamic photonic crystal is selected such that exposure of the photonic crystal to the excitation beam of polarized electromagnetic radiation changes the frequency distribution of the photonic band gap from a frequency distribution that does not significantly overlap the distribution of wavelengths of the input optical beam to a frequency distribution that does significantly overlap the distribution of wavelengths of the input optical beam, thereby substantially preventing transmission of the input optical beam of electromagnetic radiation through the photonic crystal.

BRIEF DESCRIPTION OF THE DRAWINGS

FIG. 1A provides a cross-sectional view and FIG. 1B provides a top view of the device.

FIG. 7 provides a schematic of a cross sectional view of another device of the present invention for protecting an eye or other sensor from one or more frequencies of electromagnetic radiation from a laser optical source. The device of FIG. 7 further comprises an additional photonic crystal 305 and provides enhanced reflectance for incident light at oblique angles.

FIG. 9 provides a step-by-step schematic of an exemplary method of making a photonic crystal based device of the present invention.

FIG. 18 provides an illustration of the elongated trans-state (a) and bent cis-state of a generic azobenzene molecule.

FIG. 23 provides a schematic drawing of a cross sectional view (panel a) and top view (panel b) of a 2-dimensional photonic crystal reflector.

FIG. 24 provides a plot of reflectivity (Y-axis) as a function of wavelength (X-axis) for the 2-dimensional photonic crystal structure shown in FIG. 23.

FIG. 25 provides a plot of reflectivity (Y-axis) as a function of incident angle (X-axis) at a wavelength of 532 nm for the photonic crystal structure shown in FIG. 23.

FIG. 26 provides a cross sectional view of a multiple layer 1-dimensional photonic crystal structure designed to provide a "flat top" reflection characteristic.

FIG. 27 provides a plot of reflectivity (Y-axis) as a function of wavelength (X-axis) for the photonic crystal structure shown in FIG. 26.

FIG. 28 provides a plot of reflectivity (Y-axis) as a function of incident angle (X-axis) at a wavelength of 532 nm for the photonic crystal structure shown in FIG. 26.

FIG. 29 (left panel) provides a cross sectional view of a single layer photonic crystal structure covered with a polymer film that incorporates refractive-index tunable azobenzene molecules. The right panel of FIG. 29 shows plots of reflectivity (Y-axis) as a function of wavelength (X-axis) for the device shown in the left panel of FIG. 29 in an unilluminated state and illuminated state.

In FIG. 40, maximum reflection peak shift is plotted versus laser power.

DETAILED DESCRIPTION

Figure 1:
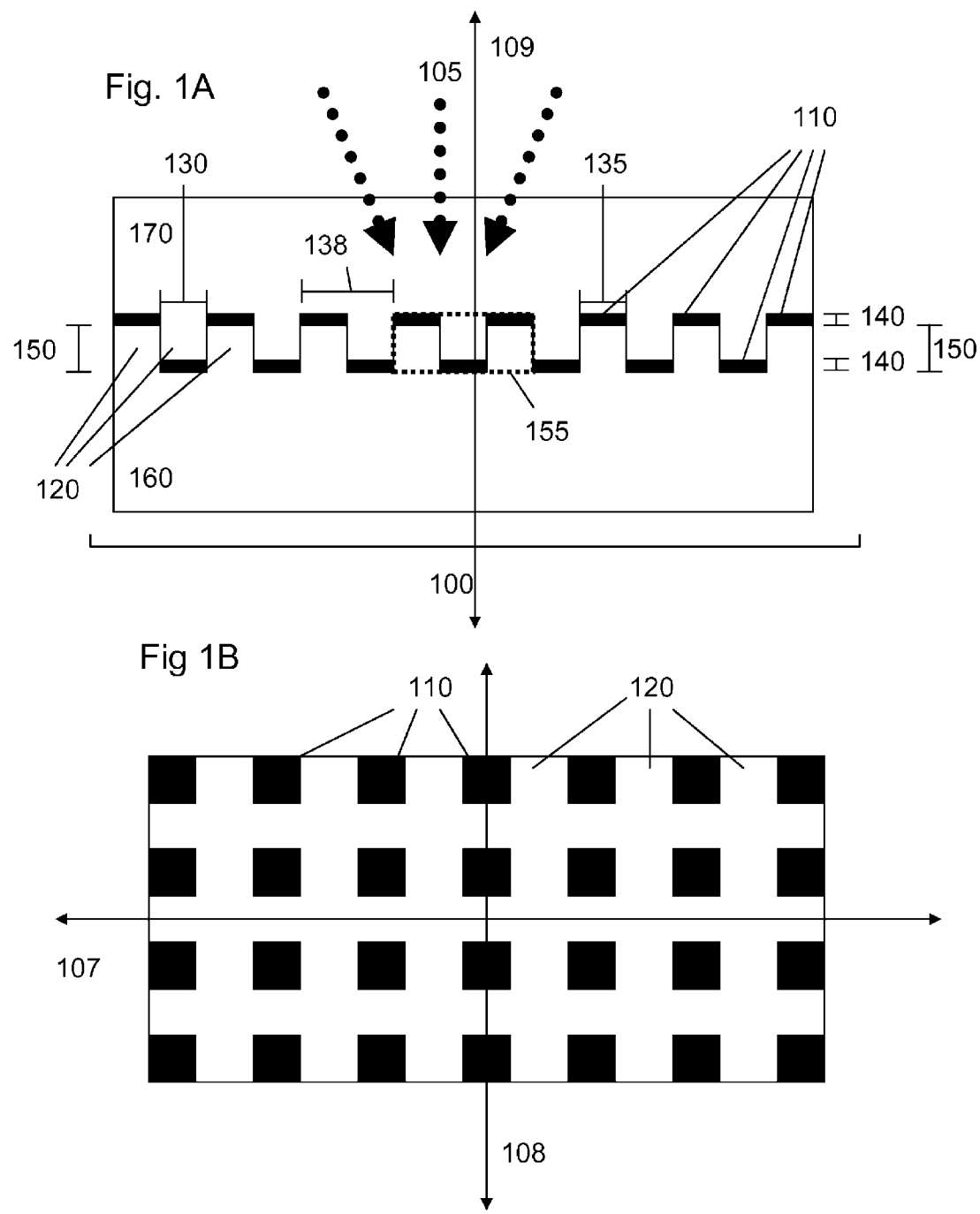
FIGS. 1A and 1B provide a schematic of a device of the present invention for protecting an eye or other sensor from one or more frequencies of electromagnetic radiation from a laser optical source.

Referring to the drawings, like numerals indicate like elements and the same number appearing in more than one drawing refers to the same element. In addition, hereinafter, the following definitions apply:

"Polymer" refers to a molecule comprising a plurality of repeating chemical groups, typically referred to as monomers. Polymers are often characterized by high molecular masses. Polymers useable in the present invention may be organic polymers or inorganic polymers and may be in amorphous, semi-amorphous, crystalline or partially crystalline states. Polymers may comprise monomers having the same chemical composition or may comprise a plurality of monomers having different chemical compositions, such as a copolymer. Cross linked polymers having linked monomer chains are particularly useful for some applications of the present invention. Polymers useable in the methods, devices and device components of the present invention include, but are not limited to, plastics, thermoplastics, elastomers, elastoplastics, thermostats, and acrylates. Exemplary polymers include, but are not limited to, polymethylmethacrylate, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, polymethylpentene, polyphenylene oxides and polyphenylene sulfides, polyphthalamide, polypropylene, polyurethanes, styrenic resins, sulphone based resins, vinyl-based resins or any combinations of these.

The term "electromagnetic radiation" and "light" are used synonymously in the present description and refer to waves of electric and magnetic fields. Electromagnetic radiation useful for the methods of the present invention includes, but is not limited to ultraviolet light, visible light, infrared light, microwaves, radio waves or any combination of these.

The terms "intensity" and "intensities" refers to the square of the amplitude of an electromagnetic wave or plurality of electromagnetic waves. The term amplitude in this context refers to the magnitude of an oscillation of an electromagnetic wave. Alternatively, the terms "intensity" and "intensities" may refer to the time average energy flux of a beam of electromagnetic radiation or plurality of beams of electromagnetic radiation, for example the number of photons per square centimeter per unit time of a beam of electromagnetic radiation or plurality of beams of electromagnetic radiation.

"Optical communication" refers to a configuration of two or more elements wherein one or more beams of electromagnetic radiation are capable of propagating from one element to the other element. Elements in optical communication may be in direct optical communication or indirect optical communication. "Direct optical communication" refers to a configuration of two or more elements wherein one or more beams of electromagnetic radiation propagate directly from a first device element to another without use of optical components for steering and/or combining the beams. "Indirect optical communication" on the other hand refers to a configuration of two or more elements wherein one or more beams of electromagnetic radiation propagate between two elements via one or more device components including, but not limited to, wave guides, fiber optic elements, reflectors, filters, prisms, lenses, gratings and any combination of these device components. When the expression optical communication is used in the present description it is intended to include configurations having 2 or more elements in: (i) direct optical communication; (ii) indirect optical communication or (iii) direct or indirect optical communication.

"Beam of electromagnetic radiation beam" refers to electromagnetic radiation propagating in the substantially the same direction (i.e. beam divergence less than 5 degrees). In the present description, use of the term beam of electromagnetic radiation is intended to be consistent with use of this term in the art of optics, opto-electronics and spectroscopy. Beams of electromagnetic radiation beam useful in the methods of the present invention included coherent beams of electromagnetic radiation beam, pulses of electromagnetic radiation and continuous wave beams of electromagnetic radiation. Beams of electromagnetic radiation beam useful in the present methods may be focusing, diverging, collimated, semicollimated or noncollimated.

"Thin film" refers to a coating or layer of atoms, molecules or ions or mixtures and/or clusters thereof. Thin films in the present invention may comprise a single-layer having a substantially constant composition, a single-layer having a composition which varies as a function of physical thickness or a plurality of thin films layers. Thin film layers of the present invention include but are not limited dielectric materials, semiconductors, conducting materials, organic materials such as polymers and any combinations of these materials. In a preferred embodiment, reference to thin dielectric films in the present invention includes but is not limited to metal oxide, metalloid oxide and salt thin films. Metal oxides, metalloid oxides and salts useable in the present invention include, but are not limited to, Ag, Au, $Ta_2O_5$, $SiO_2$, $HfO_2$, $TiO_2$, $MgF_2$, $AlO_2$, $CaF_2$, $Nb_2O_5$, glass or mixtures of these materials. Thin metalloid and metal layers of the present invention include but are not limited to Si and Al. Thin film layers of the present invention may have any size, shape, physical thickness or optical thickness suitable for a selected application.

"Optical thickness" refers to the effective path length of light that takes into consideration the refractive index of the material light is propagating through. Analytically, optical thickness and optical path length terms may be expressed in the following summation as the product of physical thickness and the refractive index of a layer or plurality of layers:

$$\text{optical thickness} = \text{optical path length} = \sum_x n_x \times L_x, \quad \text{IV}$$

where $L_x$ is the physical thickness of region x and n is the refractive index of region x. Equation IV is applicable to structures comprising single layers, partial layers and multilayer structures.

"High refractive index elements" refers to device components, materials and compositions having a larger refractive index than low refractive refractive index structural elements. "Low refractive index structural elements" refers to device components, materials and compositions having a smaller refractive index than high refractive refractive index structural elements. High and low refractive index elements of the present invention may have at least one nanosized physical dimension (e.g., height, width, length, thickness, cross section dimensions (e.g., diameter)) selected form the range of about 1 nanometer to about 1000 nanometer. The present invention includes embodiments wherein high refractive index elements and/or low refractive index elements are features of a nanostructured substrate and/or superstrate or thin films provided on such features.

The terms "frequency distribution of a photonic band gap" and "reflectance spectrum of a photonic band gap" are used synonymously in the present description and refer to the frequencies of incident electromagnetic radiation that transmission through a photonic crystal is at least partially prevented. The present invention provides dynamic photonic crystals having a tunable photonic band gap wherein the frequency distribution of the photonic band gap may be selectively adjusted by exposure of the crystal to polarized excitation electromagnetic radiation.

"Flat top frequency profile" refers to a substantially square-wave shaped frequency distribution of a photonic band gap band wherein the intensity of reflected light falls off very quickly as a function of frequency. Flat top frequency profiles of the present invention may have regions of maximum reflectance that are flat or have some curvature.

The present invention provides photonic crystal devices, device components and methods for preventing transmission of electromagnetic radiation from one or more laser sources or laser modes so as to provide an optical shield for protecting a user's eyes or an optical sensor. The present invention also provides dynamic photonic crystals and devices incorporating dynamic photonic crystals for optically modulating the intensity of one or more beams of electromagnetic radiation and other optical switching applications.

FIGS. 1A and 1B provide a schematic of a device of the present invention for protecting an eye or other sensor from one or more frequencies of electromagnetic radiation from a laser optical source. FIG. 1A provides a cross-sectional view and FIG. 1B provides a top view of the device. The device comprises a two dimensional photonic crystal 100 having a spatial distribution of refractive indices that varies periodically in at least two lateral directions (schematically shown as alignment axes 107 and 108 in FIG. 1B) and positioned to intersect electromagnetic radiation generated by a laser optical source, including laser electromagnetic radiation having normal and non-normal incident angles (for the sake of illustration laser electromagnetic radiation having normal and non-normal incident angles is schematically illustrated as dotted lines 105). The photonic crystal comprises a dielectric structure comprising alternating high refractive index elements 110 and low refractive index elements 120 provided in a periodic spatial configuration in at least two dimensions. The spatial distribution of refractive indices of the photonic crystal and/or the refractive indices of the high and the low refractive index layers (110 and 120) are selected such that the photonic band gap of the photonic crystal at least partially overlaps, and preferably for some applications completely overlaps, the range of frequencies of the incident laser electromagnetic radiation. This structure is referred to as a "2-dimensional" photonic crystal because the dielectric structure is periodic in two lateral directions (e.g., axes 107 and 108), as shown FIG. 1B. In this design, the direction of light propagation is perpendicular to the plane of the photonic crystal.

As shown in FIGS. 1A and 1B, the dielectric structure of the photonic crystal 100 comprises a two-dimensional periodic array of alternating high refractive index elements 110 and low refractive index elements 120. High refractive index elements 110 and low refractive index elements 120 have selected thicknesses 140 and 150, respectively, with respect to axes parallel to vertical direction (schematically shown as alignment axis 109). High refractive index elements 110 and low refractive index elements 120 also have selected physical dimensions along alignment axes 107 and 108, as exemplified by widths 130 and 135 of low refractive index elements and high refractive index elements, respectively, shown in FIG. 1A. In one embodiment, the "period" of the dielectric modulation (schematically shown in FIG. 1A as element as 138) is about 320 nm, the "step height" (i.e. thickness 150) is 80 nm, and the thickness of the high refractive index layers 140 is 80 nm. In the embodiment illustrated by FIGS. 1A and 1B, High refractive index elements 110 comprise thin dielectric films, such as $TiO_2$ films, and low refractive index elements 120 comprise a polymeric material, such as a polymer layer have nanosized relief and/or recessed features. In one embodiment, photonic crystals having specific defects 155 are of particular interest because they provide optical properties useful for controlling and manipulating electromagnetic radiation.

As shown in FIG. 1A, the device further comprises substrate 160 and superstrate 170 both having alternating raised and recessed relief features provided in different periodic spatial configurations. The high refractive index elements 110, such as thin dielectric films, are disposed on top of the raised and recessed relief features of the substrate 120 and at least a portion of the low refractive index elements are raised features of the substrate 160 itself. As shown in FIG. 1A, the periodic spatial configuration of the superstrate 170 corresponds to the reverse pattern of the periodic spatial configuration of the substrate such that raised and recessed regions of the superstrate line up with recessed and raised regions of substrate 160, respectively. In this embodiment, the superstrate 170 is positioned such that it is in contact with at least a portion of the high refractive index elements, and at least a portion of the low refractive index elements comprise raised relief features of the superstrate 170 itself.

To provide optical shielding (i.e. optical filtering) functionality, the two-dimensional photonic crystal device is provided between a source of laser electromagnetic radiation and the eye of a user or a sensor. The periodic spatial distribution of refractive indices of high and low refractive index elements is selected such that the photonic band gap of the crystal overlaps, preferably entirely, with the frequency distribution of the laser electromagnetic radiation. Therefore, transmission of electromagnetic radiation from the laser source is substantially prevented (i.e., light is reflected), thereby protecting the user or sensor.

Figure 2:
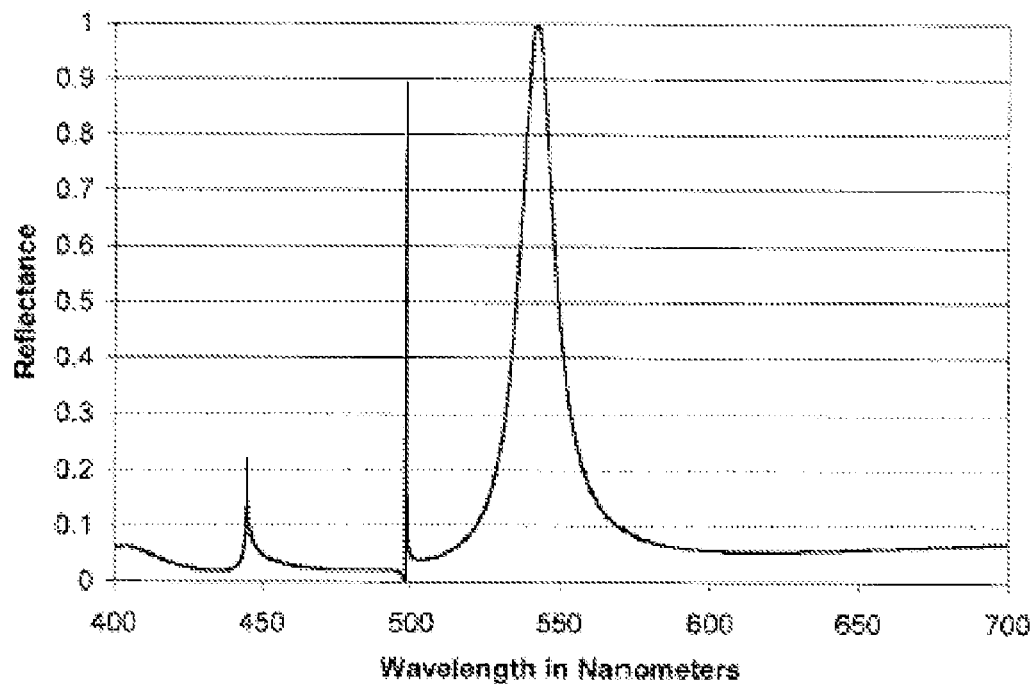
FIG. 2 shows a numerical calculation of the reflectance spectrum for an exemplary photonic crystal having a "period" of the dielectric modulation of about 320 nm, a "step height" (i.e. thickness 150) of about 80 nm, and a thickness of the high refractive index layers 140 of about 80 nm.

FIG. 2 shows a numerical calculation of the reflectance spectrum for an exemplary photonic crystal having a period of the dielectric modulation (schematically shown in FIG. 1A as element 133) of about 320 nm, a "step height" (i.e. thickness 150) of about 80 nm, and a thickness 140 of the high refractive index layers 110 of about 80 nm. The reflectance spectrum shown is calculated for electromagnetic radiation of normal incidence with respect to a receiving surface of the photonic crystal, and was calculated using RSoft Corporation's DiffractMOD. This commercially available software package uses a Rigorous Coupled Wave Analysis method for applying Maxwell's equations to periodic structures.

The simulation in FIG. 2 shows that there is a narrow band of strong reflectance centered at 542 nm. Because the reflectance is 100% at exactly 542 nm, this structure is effective at blocking a laser with an emission wavelength of 542 nm. It is important to note that there is very little reflection in the remainder of the spectrum (i.e. frequencies other than the narrow band centered around 542 nanometers). This is a desirable feature of laser protection eyewear that is to be worn in a field setting. It also should be noted that for the case of normal incidence, the filtering provided by the photonic crystal is independent of polarization state. This is due to the two dimensions of periodicity of the dielectric structure. No matter the state of polarization, the electric field vector can always be broken into an x-component and a y-component, which are imagined to be along each direction of periodicity.

Figure 3:
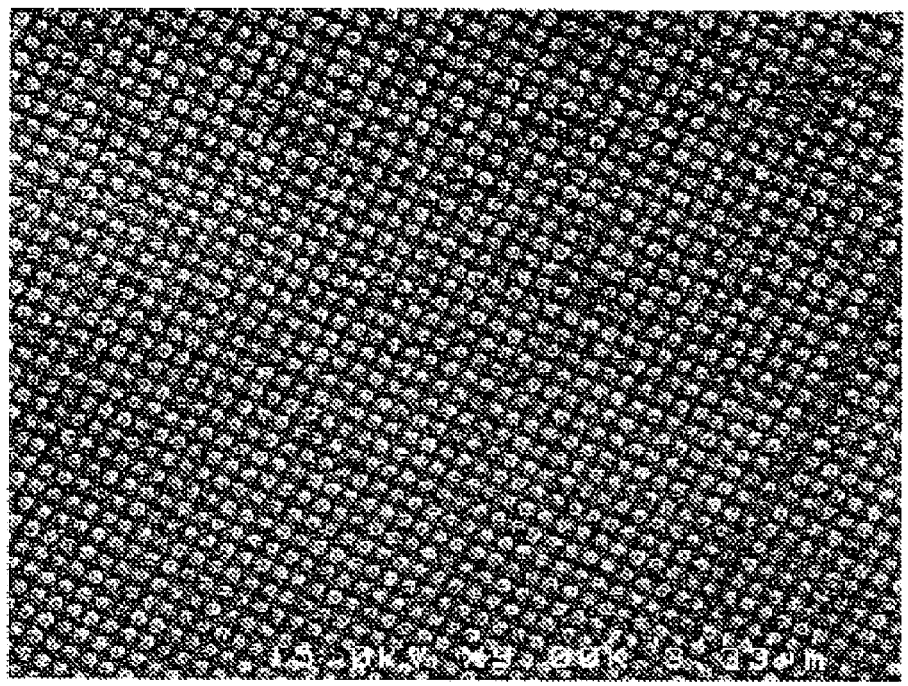
FIG. 3 provides a scanning electron microscope image of an exemplary fabricated substrate having a pattern of raised and recessed relief features for use in a two dimensional photonic crystal in devices of the present invention.

FIG. 3 provides a scanning electron microscope image of an exemplary fabricated substrate comprising a dielectric structure having a periodic pattern of raised and recessed relief features for use in a two dimensional photonic crystals and devices of the present invention. The lightly shaded areas are raised relief feature of higher elevation. In other words, the viewer is looking at an array of circular posts sticking up from the substrate. The raised features of the substrate may also have shapes other than the cylindrical posts shown in FIG. 3, such as rectangular, triangular, elliptical and/or square columns. The period of the dielectric structure shown in FIG. 3 is 310 nm.

Figure 4:
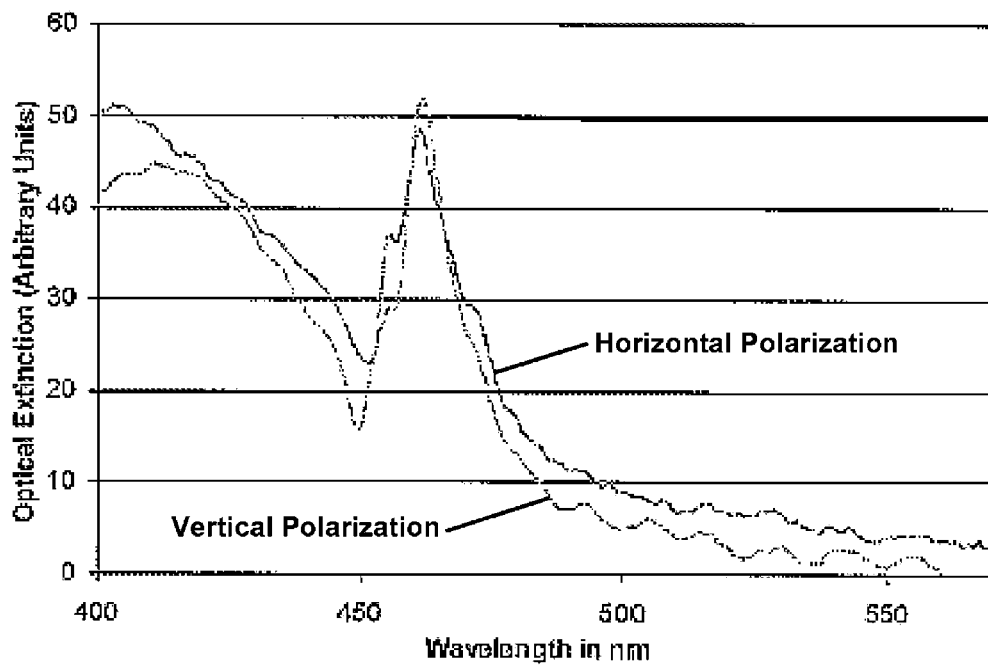
FIG. 4 provides optical transmittance measurements on the fabricated dielectric structure shown in FIG. 3. The plot in FIG. 4 shows the optical extinction (reflection and absorption) spectrum for this structure.

FIG. 4 provides optical transmittance measurements for a photonic crystal fabricated using the dielectric structure shown in FIG. 3. The plot in FIG. 4 shows the optical extinction (reflection and absorption) spectrum for this structure and demonstrates the polarization independence of this design. As shown in FIG. 4 the performance of the device is very similar for horizontal and vertical polarization states. The peaks centered near 460 nm are the reflection peaks characteristic of the photonic crystal structure, whereas the extinction towards the short-wavelength end of the spectrum is likely due to absorption in the substrate material.

Figure 5:
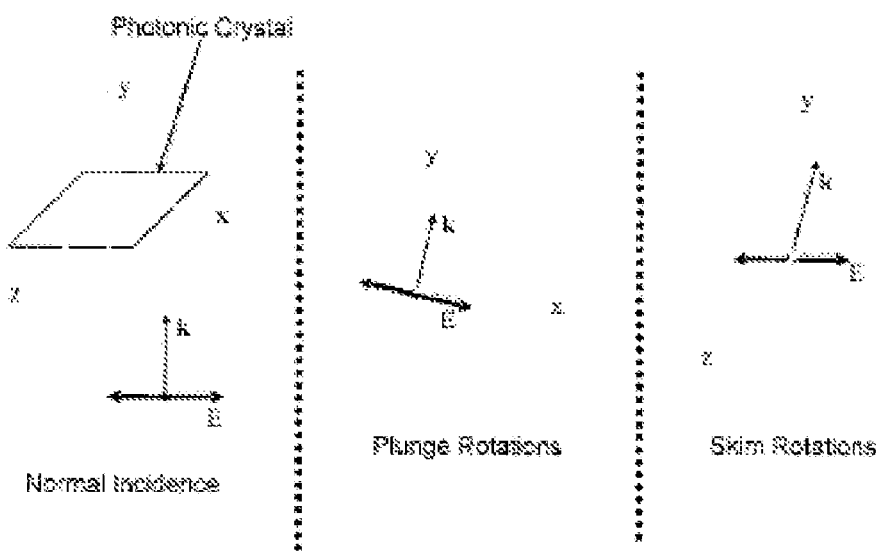
FIG. 5 provides a schematic showing how the electric field and wave vectors are oriented for p-polarization and s-polarization states at oblique angles.

Of importance to the usefulness of the device of the present invention is the reflection performance at oblique (non-normal) angles of incidence. FIG. 5 provides a schematic showing how the electric field and wave vectors are oriented for p-polarization and s-polarization states at oblique angles. It should be noted that there are two physically unique ways to rotate the angle of incidence with respect to the plane of the photonic crystal. This is illustrated in FIG. 5. For the case of p-polarized light (known informally as "plunge" polarization), the wavevector is rotated such that the electric field vector is no longer parallel to the plane of the photonic crystal. In the case of s-polarization (or "skim" polarization), the electric field vector remains parallel to the plane of the photonic crystal. The reflectivity of the photonic crystal is different for s-polarization and p-polarization states for electromagnetic radiation having non-normal incident angles.

Figure 6:
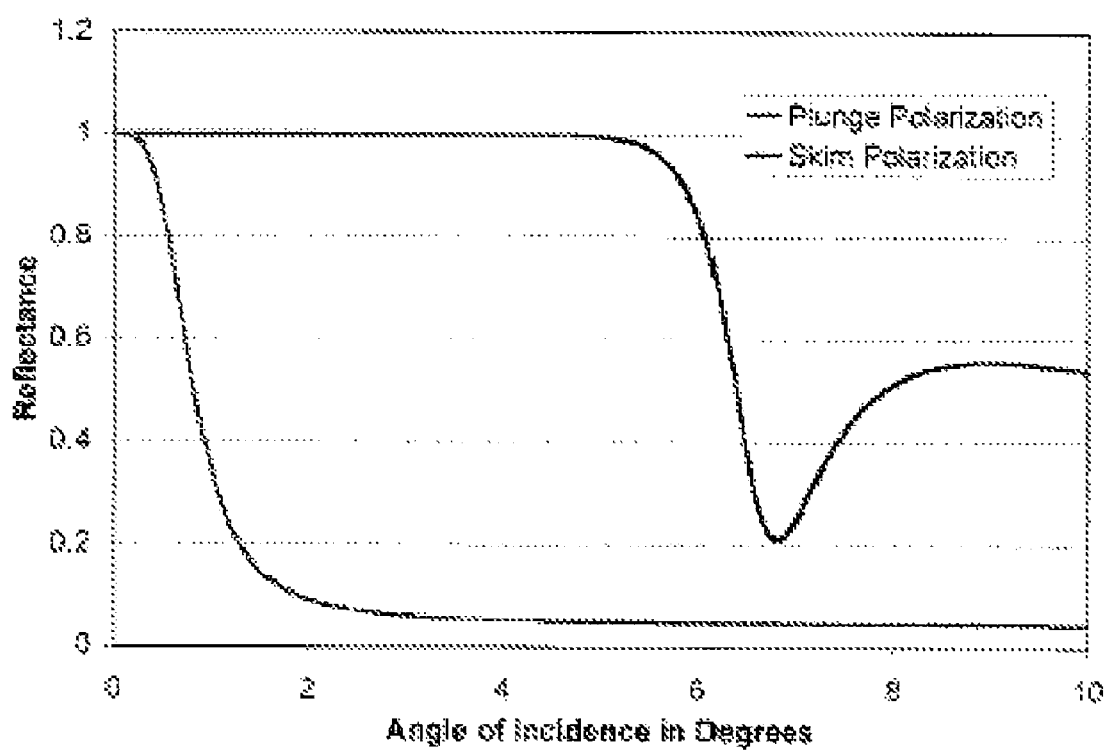
FIG. 6 shows results from RCWA (rigorous coupled wave analysis) simulations of the reflectance at various angles of incidence for the structure described in the context of FIG. 2.

FIG. 6 shows results from RCWA (rigorous coupled wave analysis) simulations of the reflectance at various angles of incidence for the structure described in the context of FIG. 1. The simulations were performed at the design (or center) wavelength of 542 nm. In this plot, zero degrees corresponds to normal incidence. FIG. 6 shows that the reflection performance of the plunge rotation angles is better than that of the skim rotation angles. For the case of plunge polarization, a reflectance of 80% is maintained out to an angle of 6 degrees. On the other hand, the reflectance drops below 80% for angles larger than 0.5 degrees for skim rotation angles FIG. 7 provide a schematic of a cross sectional view of another device configuration of the present invention for protecting an eye or other sensor from one or more frequencies of electromagnetic radiation from a laser optical source. The device of FIG. 7 further comprises an additional photonic crystal 305 and provides enhanced reflectance for incident light at oblique angles. As shown in 7A, the optical shielding device 300 further comprises a second two dimensional photonic crystal comprising a dielectric structure comprising alternating high refractive index elements 310 and low refractive index elements 320 provided in a periodic spatial configuration in at least two dimensions. The spatial distribution of refractive indices of the second photonic crystal 305 and/or the refractive indices of the high and the low refractive index layers 310 and 320 is substantially the same as the high refractive index elements 110 and low refractive index elements 120 of the first photonic crystal 105. Further, thickness (340 and 350) and lengths (330 and 335) of high and the low refractive index layers 310 and 320 are also substantially the same as those corresponding to high refractive index elements 110 and low refractive index elements 120. In some embodiment period 338 of the second photonic crystal 305 is the same as period 138 of first photonic crystal 105. The present invention includes embodiments, however, wherein spatial distributions and refractive indices of high and low refractive index elements of second photonic crystal 305 are different than that of first photonic crystal 105.

First photonic crystal 105 and second photonic crystal 305 are separated by a separation layer 400 that is capable of maintaining a selected and constant optical pathlength 360 between these device elements along alignment axis 109. In an embodiment, separation layer 400 is a polymer material having substantially the same (e.g. within about 5%) refractive index as the refractive index of substrate 160, superstrate 170 or both substrate 160 and superstrate 170. In an embodiment, separation layer 400 separates first and second photonic crystals by a distance that provides for optical coupling of diffracted electromagnetic radiation between the grating regions of first and second photonic crystals. In one embodiment, for example, separation layer 400 separates first and second photonic crystals by a distance along alignment axis 109 equal to about 260 nanometers.

Figure 8A:
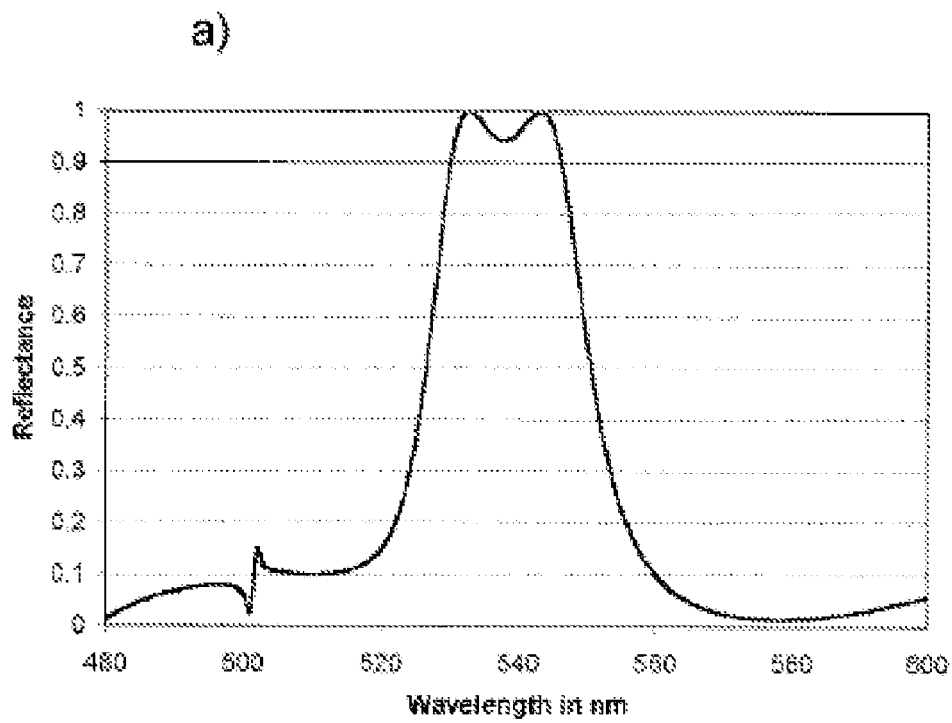
FIGS. 8A & 8B shows a simulated reflectance spectra for electromagnetic radiation of normal incidence for an exemplary coupled, dual photonic crystal design having a configuration as illustrated in FIG. 7.
Figure 8B:
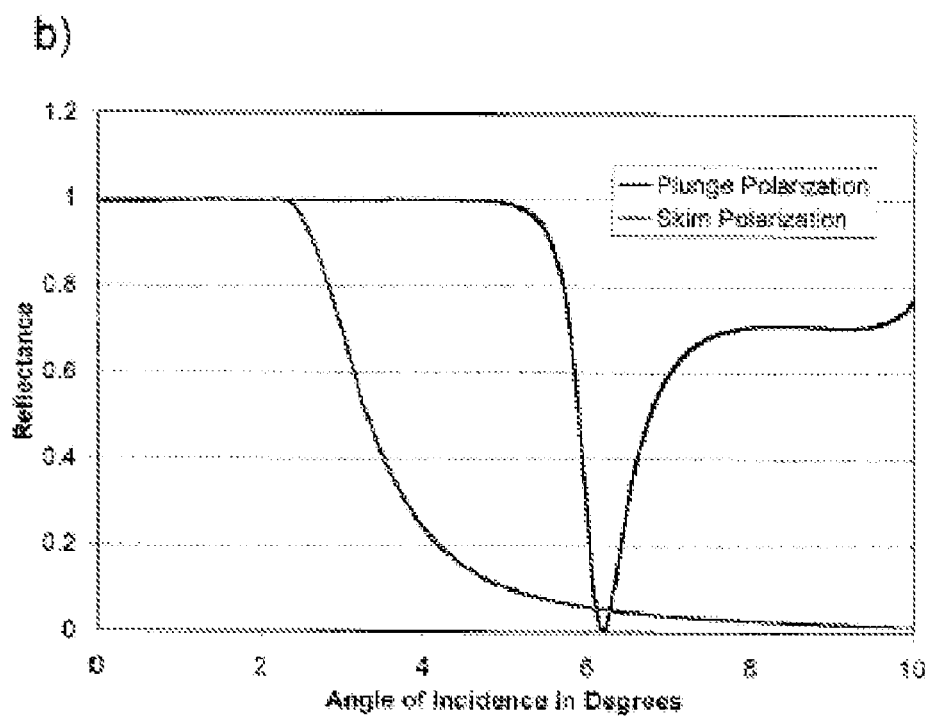

FIGS. 8A and 8B shows a simulated reflectance spectrum for electromagnetic radiation of normal incidence for an exemplary optically coupled, dual photonic crystal design having a configuration as illustrated in FIG. 7. Also shown is the calculated reflectance performance for oblique angles at the 542 nm design wavelength. As shown in FIGS. 8A and 8B, it is apparent that this coupled two-layer photonic crystal design has enhanced reflection performance for incident electromagnetic radiation having oblique angles with respect to single layer photonic crystal designs. For skim polarization at oblique angles, 80% reflectance is maintained through 2 degrees of rotation. The reflectance performance for plunge polarization has suffered a bit, maintaining 80% reflectance out to 5.7 degrees.

U.S. Pat. No. 6,951,715, and U.S. Patent Application Publication Nos. 20030017580, 20030026891 and 20030027327 describe exemplary methods for making, and using dielectric structures, photonic crystals and photonic crystal devices useful in the present invention, and are incorporated by reference herein in their entireties.

FIG. 9 provides a step-by-step schematic of an exemplary method of making a photonic crystal based device of the present invention. In an exemplary method, a first step is to use silicon processing techniques to make a master copy of the grating surface structure in a silicon wafer. In a useful embodiment, for example, a pattern corresponding to the negative of the desired photonic crystal surface structure is fabricated in the silicon wafer. Exemplary embodiments use direct-write electron beam lithography to pattern a 2 mm by 2 mm region of the silicon wafer. After the wafer has been patterned, it is used for the imprint replication process an indefinite number of times. For the actual replication, a few drops of liquid-form UV-curable polymer are applied to the surface of the silicon wafer. Next, a sheet of flexible plastic substrate is pressed onto the UV-curable polymer. To cure the polymer, the wafer-epoxy-plastic sandwich is exposed to ultraviolet light. After curing, the flexible plastic sheet is peeled off the silicon wafer. The cured polymer adheres to the plastic sheet, allowing the wafer master to be used again and again. Once the positive pattern has been transferred to the plastic substrate, a thin film of titanium dioxide is deposited onto the structured surface. To make a structure with two layers of titanium dioxide, a film of low-index dielectric such as $SiO_2$ must be deposited in between the two layers of $TiO_2$. In one embodiment, we include a superstrate of cured epoxy (not shown in FIG. 9) which sits on top of the upper layer of $TiO_2$. This inclusion is to protect the photonic crystal structure.

For some applications, it is useful to provide an optical shielding device, such as laser protection eyewear, wherein the human eye is protected from incident electromagnetic radiation over a wide range of oblique angles. In one embodiment of the present invention useful for these applications, a photonic crystal is provided in a contoured configuration such that it has receiving surface having a radius of curvature similar to that of human eye. This embodiment, provides excellent protection in this context because in this configuration the photonic crystal only need to provide high reflectance over a relatively small range of incident angles (e.g. 5 to 10 degrees from normal incidence). Moreover, the further the laser protection eyewear is positioned away from the eye, the stronger the enhancement in protection from incident electromagnetic radiation at oblique angles.

Figure 10:
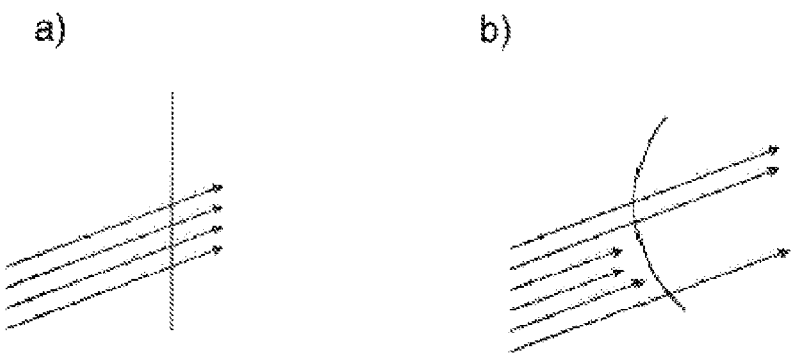
FIG. 10 is a schematic diagram comparing the interaction of incident electromagnetic radiation propagating along a non-normal propagation axis with a flat-surface photonic crystal device (panel a) and a photonic crystal device having a curvature similar to that of the human eye (panel b).

FIG. 10 is a schematic diagram comparing the interaction of incident electromagnetic radiation propagating along a non-normal propagation axis with a flat-surface photonic crystal device (panel a) and a photonic crystal device having a curvature similar to that of the human eye (panel b). As shown in panel (a) of FIG. 10, the photonic crystal eyewear has a planar receiving surface and, hence, a beam incident at an angle of 20 degrees would be completely unaffected by the photonic crystal. On the other hand, photonic crystal eyewear with a contoured receiving surface having curvature similar to a human eye, as shown in panel (b) of FIG. 10, substantially increases the likelihood that the angle that the beam makes with the receiving surface will be within the range of functionality of the photonic crystal. Furthermore, incident beams that aren't within the range of functionality might reach the eye at a less-critical position and angle and, thus, will likely not be focused by the lens of the eye onto the retina.

Optical shielding devices of the present inventing, such as laser protection eyewear, can also be designed to simultaneously block several different laser wavelengths. To achieve this functionality, at least one additional photonic crystal designed to block a different laser wavelength is incorporated in the devices. In one embodiment, multiple photonic crystals having band gaps with different frequency distributions are provided in a stacked configuration with multiple layers of photonic crystal structures positioned on top of each other. This design work is simply a matter of scaling the period, step height, and optical thickness of high and low refractive index layers in a linear fashion. For example, if it is desired that the photonic crystal block a laser with a wavelength of 1084 nm, then all one must do is double the size of all of the dimensions of the 542 nm design. Then, using the plastic and curable polymer replication process, the photonic crystal designed to block the second laser wavelength is imprinted onto the same substrate as the photonic crystal designed for blocking the first laser wavelength. Since each photonic crystal layer is very thin, one could incorporate protection for many different laser wavelengths into a single stack.

Figure 11:
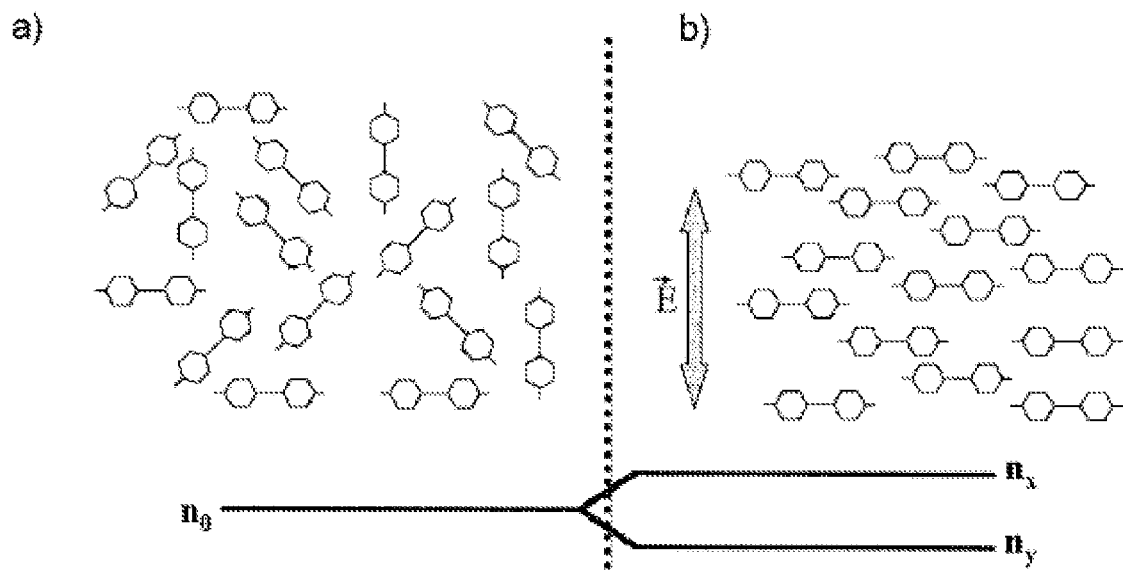
FIG. 11 provides a schematic diagram illustrating alignment of the azobenzene molecules in a direction perpendicular to the polarization of the laser beam upon illumination by a polarized incident laser. Panel (a) of FIG. 11 provides a schematic showing the state of azobenzene molecules before laser illumination and panel (b) of FIG. 11 provides a schematic showing the state of azobenzene molecules before after illumination with linearly polarized light.

The present invention provides laser protection eyewear having a dynamical photonic crystal with a tunable photonic band gap that can be selectively adjusted during or after fabrication by altering the optical properties of the structure via illumination with linearly polarized electromagnetic radiation. In a useful embodiment of this aspect of the present invention, low refractive index elements of the photonic crystal comprise a photodynamic polymer material, such as azobenzene-containing polymer that changes refractive index rapidly upon exposure to polarized electromagnetic radiation. FIG. 11 provides a schematic diagram illustrating alignment of the azobenzene molecules in a direction perpendicular to the polarization of the laser beam upon illumination by a polarized incident laser beam. Panel (a) of FIG. 11 provides a schematic showing the state of azobenzene molecules before laser illumination and panel (b) of FIG. 11 provides a schematic showing the state of azobenzene molecules after illumination with linearly polarized light. The photo-alignment causes the azobenzene-containing polymer to become birefringent. The index of refraction along the direction of molecular alignment will increase, while the index of refraction along the direction of laser polarization will decrease. This change in the index of refraction causes the frequency distribution of the photonic band gap of the photonic crystal to change and provides a useful means of selectively adjusting the frequency distribution of the photonic band gap.

Figure 12:
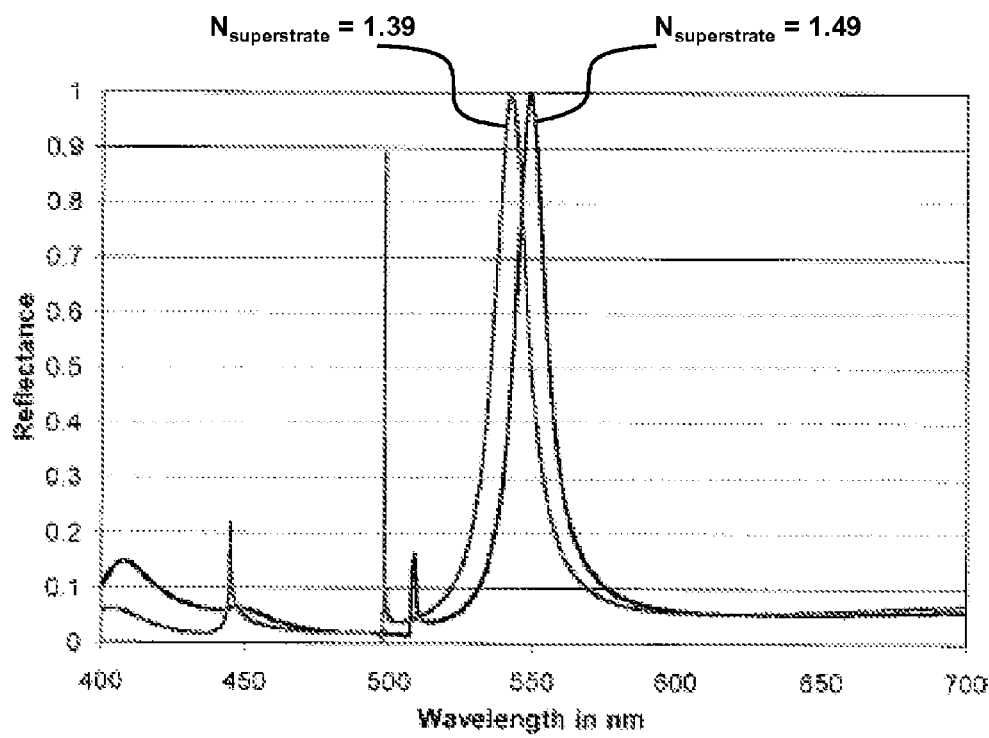
FIG. 12 provides a plot showing the simulated shift in the reflectance peak of a dynamic photonic crystal upon exposure to a beam of linearly polarized excitation beam of electromagnetic radiation.

FIG. 12 provides a plot showing the simulated shift in the reflectance peak of a dynamic photonic crystal upon exposure to a beam of linearly polarized excitation beam of electromagnetic radiation. Shown below is a simulation of a peak shift caused by a change in the index of refraction of 0.1 in the azobenzene-containing polymer layer. The plot shows that the peak wavelength of reflectance is 542 nm for when the index of the polymer film is 1.39, and 549 nm when the film index is 1.49.

Figure 13:
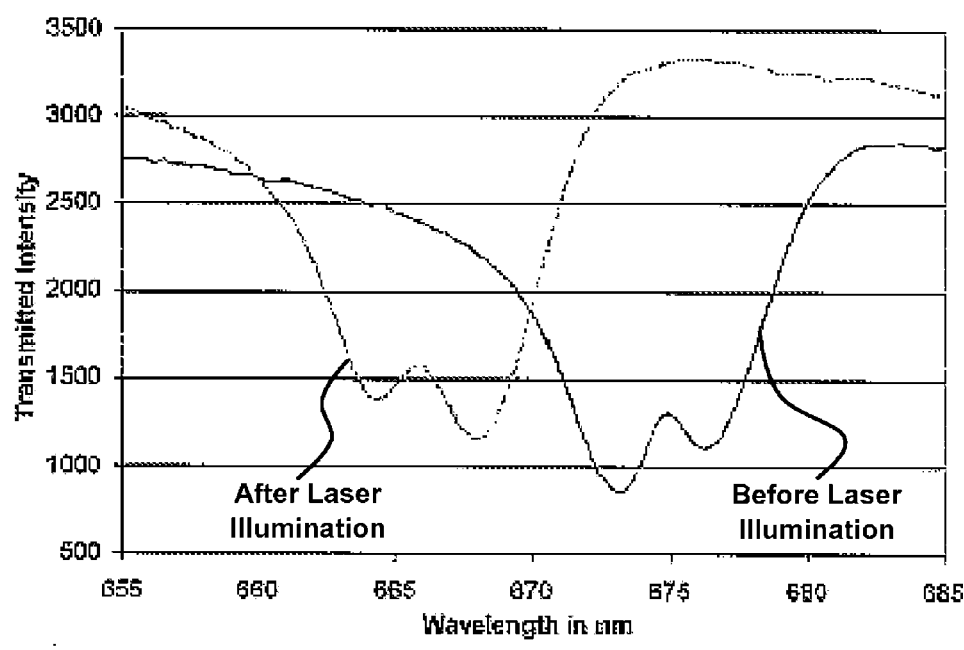
FIG. 13 provides a plot showing a measured shift in the frequency distribution of a photonic band gap of a dynamic photonic crystal of the present invention. The plot in FIG. 13 shows a 9 nm shift in the reflection peak after the dynamic photonic crystal was illuminated with polarized laser light.

FIG. 13 provides a plot showing a measured shift in the frequency distribution of a photonic band gap of a dynamic photonic crystal of the present invention. The plot in FIG. 13 shows a 9 nm shift in the reflection peak after the dynamic photonic crystal is illuminated with polarized laser light. It should be noted that the plot shows transmitted intensity, whereas some of the previously described graphs plot reflectance. For this experiment, a commercially available one-dimensional grating was used as the replication master. The photodynamic polymer of the dynamic photonic crystal was fabricated using polymethylmethacrylate (PMMA) and the azobenzene dye Disperse Red 1. By weight, the polymer film was composed of 95% PMMA and 5% DR1. Given the significant magnitude of the peak shift, we estimate that the change in the index of refraction in the polymer film was of the order of 0.1.

Although the peaks started shifting as soon as the sample is exposed to the laser, it took several seconds for the peaks to complete their full shift. For the full resonance shift to occur, the direction of laser polarization must be along one of the axes of the photonic crystal. If, however, the laser is polarized at an angle of 45 degrees to an axis, then it is predicted that the photo-induced birefringence will not cause any shift in the reflection resonance of the photonic crystal. This is because there will be zero net change in the refractive index in the polymer film along each axis of the photonic crystal.

However, this problem can be mitigated somewhat by stacking two photonic crystal layers such that their axes are offset by a 45 degree angle. In this scenario, if the polarization of the incoming laser happens to be at a 45 degree angle with respect to the axis of one photonic crystal, then the laser light polarization will be exactly aligned with the other photonic crystal, giving the maximum shifting effect. With this two layer stack, it is predicted that a minimum shifting effect of 70.7% of the maximum possible shift will always be guaranteed. Constructing a four-layer stack with the photonic crystal axes each offset by 22.5 degrees would ensure a minimum shift of 92% of the maximum possible shift.

Figure 14:
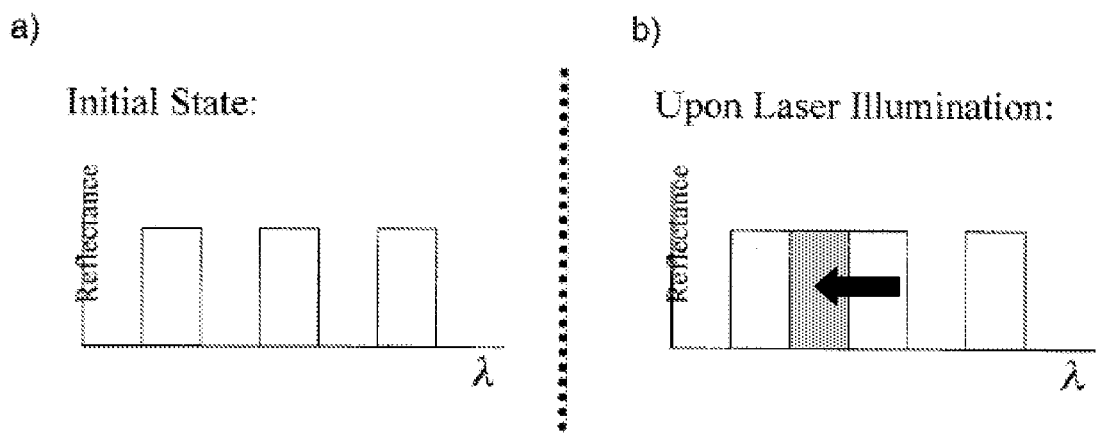
FIG. 14 provides a conceptual illustration of how static and dynamic photonic crystals can be combined in a stacked device configuration capable of providing dynamic and spectrally continuous laser protection upon illumination while still affording good outward visibility when not illuminated. Panel (a) of FIG. 14 shows the reflectance spectrum corresponding to an un-illuminated state and Panel (b) of FIG. 14 shows the reflectance spectrum upon illumination with laser electromagnetic radiation.

Another embodiment of the laser safety eyewear of the present invention includes a plurality of the structural and functional features described, and is capable of blocking off a continuous region of the optical spectrum, thus providing eye protection for any incident wavelength, while still affording the user good outward visibility while not under laser illumination. FIG. 14 provides a conceptual illustration of how static and dynamic photonic crystals can be combined in a stacked device configuration capable of providing dynamic and spectrally continuous laser protection upon illumination while still affording good outward visibility when not illuminated. Panel (a) of FIG. 14 shows the reflectance spectrum corresponding to an un-illuminated state and Panel (b) of FIG. 14 shows the reflectance spectrum upon illumination with laser electromagnetic radiation. Included in the stack of photonic crystals is a series of static photonic crystal structures (such as those described previously) providing photonic band gaps with selected flat-top frequency distributions spaced evenly throughout the optical spectrum. In addition, a series of dynamic azobenzene-containing photonic crystals having tunable flat-top photonic band gaps that overlap the frequency distributions of the static flat-top filters. Upon illumination with polarized laser light, however the photonic band gaps of the dynamic azobenzene-containing photonic crystals shift, thus blocking off a continuous region of the spectrum, as is schematically shown in panel (b) the FIG. 14. In the context of the description, "blocking off" refers to photon band gaps having frequency distributions that combine to substantially prevent transmission of laser electromagnetic radiation over a wider range of frequencies than provided by a single static flat-top photonic crystal filter.

In embodiments using some azobenzene photodynamic materials, the laser electromagnetic radiation must be linearly polarized for there to be any photo-induced birefringence. Circularly polarized light, elliptically polarized light, and unpolarized light will all cause randomization of certain the azobenzene molecules. Other considerations for the tunable aspect of the present laser protection eyewear include the response time of the azobenzene molecules. For certain applications of this aspect of the present invention use of photodynamic materials, such as azobenzene dyes, that provide fast changes in refractive index, such as changes occurring on microsecond or less time scales, is preferred for some applications.

The present invention also provides all optical switching devices having a dynamic photonic crystal capable of providing a tunable photonic band gap. Dynamic photonic crystals having tunable photonic band gaps provide functional components in all-optical switch/transistor for telecommunications and in all-optical computing systems. In optical switching applications, parameters such as polarization and angle of incidence are carefully controlled. Furthermore, one does not need a very large shift in the frequency distribution of the photonic band gap to achieve effective optical switching and such small shifts can be achieved on very fast time scales (e.g., microsecond, nanosecond or femtosecond time scales).

Figure 15:
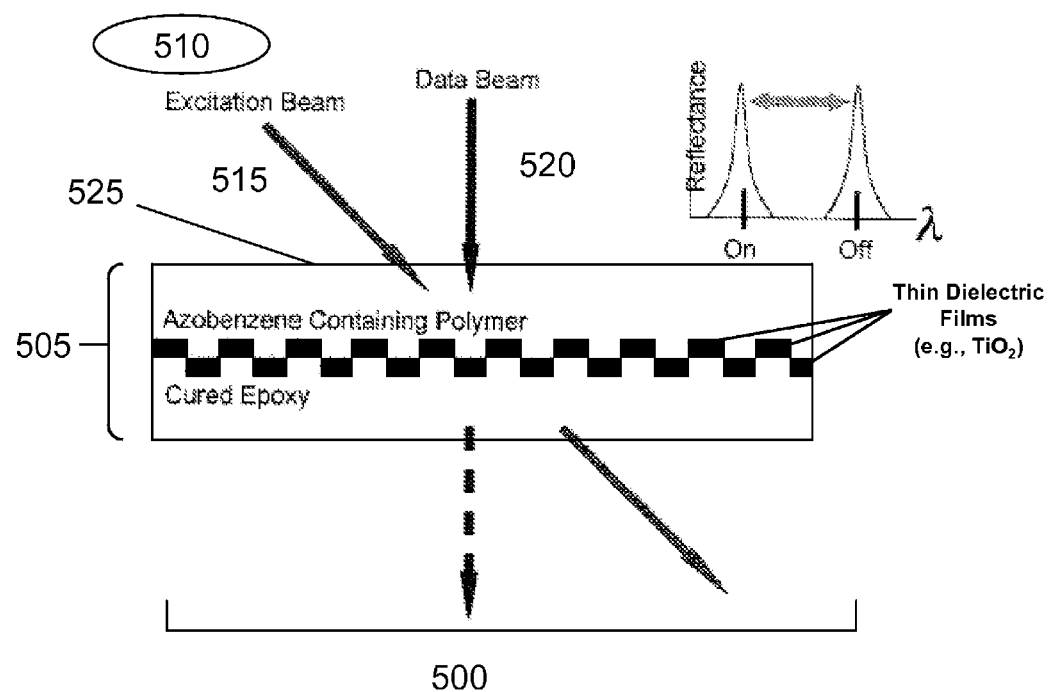
FIG. 15 provides a schematic diagram of an optical switching device of the present invention using a dynamic photonic crystal having high refraction index or low refractive index elements comprising a photodynamic azobenzene containing polymer.

FIG. 15 provides a schematic diagram of an optical switching device of the present invention using a dynamic photonic crystal having low refractive index elements comprising a photodynamic azobenzene containing polymer. Switching device 500 comprises dynamic azobenzene-containing photonic crystal 505 in optical communication with optical excitation source 510. As shown in FIG. 15, the dynamic photonic crystal comprises: (i) a cured epoxy substrate having a pattern of relief and recessed features; (ii) thin dielectric films (e.g., $TiO_2$), and (iii) a azobenzene-containing polymer superstrate having a pattern of relief and recessed features that is the negative pattern of that of the substrate. Photonic crystal 505 is positioned such that optical source 510 is capable of providing a polarized excitation beam of electromagnetic radiation 515 to receiving surface 525 of photonic crystal 505. Photonic crystal is also positioned such that input optical beam 520 is received on receiving surface 525. The shift in frequency distribution of the band gap of the dynamic photonic crystal is schematically illustrated in the reflectance spectra (upper right corner) shown for the "on state" and the "off state".

In this embodiment the polarized excitation beam of electromagnetic radiation 515 is used to control whether or not the input optical beam 520 propagates through the dynamic photonic crystal 505. In the "off" state, the excitation beam 515 is off, and the frequency distribution of the band gap of the photonic crystal at least partially, if not completely overlaps, the frequency distribution of the input optical beam 520. In the off state, therefore, the input optical beam 520 does not propagate through the photonic crystal. If the excitation beam 515 is switched on, however, the photoinduced birefringence in the azobenzene film will cause the frequency distribution of the photonic band gap of crystal 505 to shift. The shifting of frequency distribution of photonic band gap of crystal 505 allows the input optical beam 520 to propagate through photonic crystal. This condition is defined as the "on" state.

In some embodiments, the input optical beam 520 and the excitation beam 515 are not of the same wavelength. This embodiment would be configured such that the excitation beam 515 is within the spectral absorption band of the azobenzene molecules, while the input optical beam 520 is not within the azobenzene absorption spectrum. In an alternative embodiment, the excitation beam 515 and the input optical beam 520 have the same or similar frequency distributions, at least a portion of which is absorbed by the azobenzene molecules. In this embodiment, the photonic crystal reflection peak will be in a shifted state even when the switch is in the "off" state. When the excitation beam 515 is switched on, the reflection peak will shift further, due to the increased absorption caused by the additional irradiation.

There are two fundamental differences between the all-optical switch and the tunable laser protection eyewear described previously. The first difference is that for the optical switch, a principle design goal for the photonic crystal is to obtain the narrowest photonic band gap capable of providing good switching functionality. If the band gap is narrow, then it will only have to shift by a small amount to switch from a state of complete reflection to a state of complete transmission for the wavelength of the input optical beam 520. The benefits of a narrow band gap makes use of a one-dimensional photonic crystal attractive in combination with an input optical beam 520 having polarization perpendicular to the grating lines particularly attractive. One dimensional photonic crystals are capable of providing very narrow photonic band gaps. In particular, the frequency distribution of the band gap is narrowest when the refractive index of the substrate is close to the refractive index of the superstrate.

Figure 16:
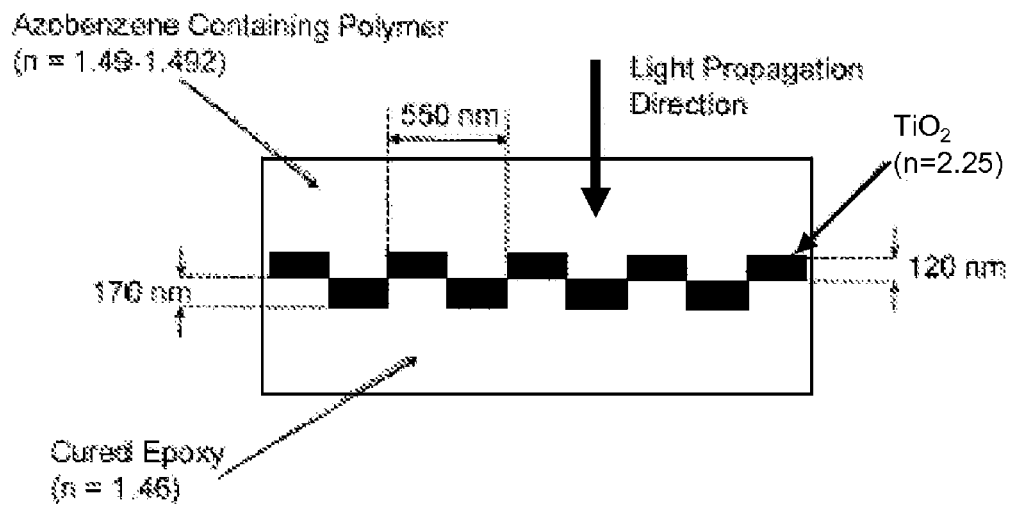
FIG. 16 shows a schematic of a cross section of a one-dimensional photonic crystal configuration useful in optical switching devices of the present invention.

FIG. 16 shows a schematic of a cross section of a one-dimensional photonic crystal configuration useful in optical switching devices of the present invention. As shown in FIG. 16, the substrate comprises cured expoxy having a refractive index of 1.46, the superstrate comprises a photodynamic azobenzene containing polymer having a refractive index that varies from about 1.49 to about 1.492 depending on the illumination conditions, and high refractive index layers comprise thin (120 nanometer thick) $TiO_2$ films having a refractive index of about 2.25. As also shown in FIG. 16, the step height is 170 nanometers and the periodicity is 550 nanometers.

Figure 17:
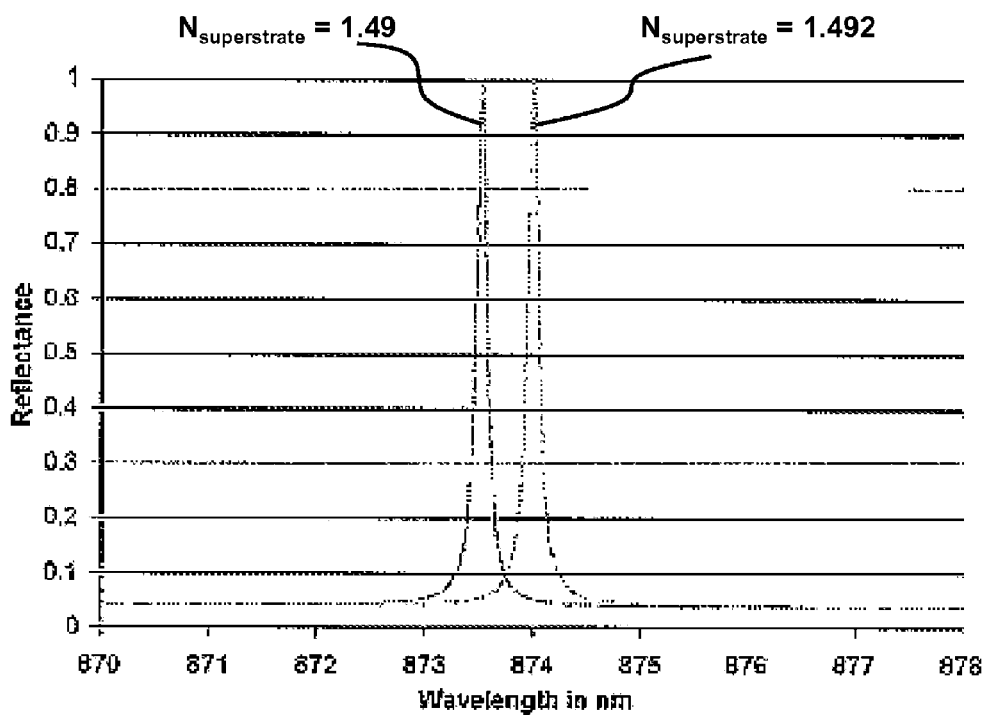
FIG. 17 shows simulated frequency distribution of the photonic band gap of the structure schematically illustrated in FIG. 16 for two different refractive indices of the superstrate, 1.49 and 1.492.

FIG. 17 shows simulated frequency distribution of the photonic band gap of the structure schematically illustrated in FIG. 16 for two different refractive indices of the superstrate, 1.49 and 1.492. The full-width at half-maximum (FWHM) of the frequency distribution of the photonic band gap for this one-dimensional photonic crystal is simulated to be 0.12 nm. It should be noted that the reflection peak only has to shift by 0.475 nm for a 873.52 nm beam to switch from a state of 100% reflection to a state of 5% reflection. This 0.475 nm shift corresponds to a change in the polymer refractive index of 0.002.

A useful aspect of dynamic photonic crystal in this aspect of the present invention is that the required magnitude of peak shifting of the photonic band gap is much less for the optical switching applications than for laser filtering applications using these materials. For example, a complete switching effect can be achieved with a refractive index change on the order of 0.001. Using the present photodynamic polymer materials, a photoinduced birefringence of 0.001 can be achieved very quickly.

In some embodiments, to achieve such a small birefringence, the device does not rely on the rotation of azobenzene molecules at all. There are two photodynamic effects in azobenzene-containing polymers. The first is the realignment of trans-state azobenzene molecules. Trans-state azobenzene molecules have an elongated structure. FIG. 18 provides an illustration of the geometries of the elongated trans-state (a) and bent cis-state of a generic azobenzene molecule. As mentioned previously, this effect is known to occur on millisecond and second timescales and results in relatively large values of photoinduced birefringence (due to the elongated geometry of the molecule). The other known birefringence-causing phenomena in azobenzene is the trans-cis excitation. This process is known to be much faster: trans-cis transitions can happen on a nano-second or femto-second timescale. Although the trans-cis excitation happens very quickly, the resulting magnitude of photoinduced birefringence is much smaller than for the case of trans-state realignment. As shown in the simulation in FIG. 17, however, a small photoinduced birefringence is sufficient to enable the all-optical switching applications of the present invention.

Statements Regarding Incorporation by Reference and Variations

All references cited throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, materials, reagents, synthetic methods, purification methods, analytical methods, assay methods, and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Example 1

Photonic Crystal Wavelength-Selective Tunable Filters for Laser Eye Shielding

1.A Summary of Technical Objectives

The rapid development of laser technology has made portable laser systems with high power and energy widely available for applications in communication, scientific research, and manufacturing. Unfortunately, these laser systems have also been employed as a means for disabling soldiers and weapon systems by inflicting damage to human eyes and photosensors. Therefore, the development of countermeasures that can limit the effectiveness of laser weapons against these targets is an important area of research. The goal of certain embodiments of the present invention is to develop of laser eye shielding technology that is capable of reflecting particular wavelengths of laser light with nearly 100% efficiency while still enabling the soldier to see out from the shield at other wavelengths. Additionally, the laser eye shield should be capable of rapidly responding to the threat laser so that the shield's reflected wavelength may be tuned. Finally, the laser eye shield must be inexpensive to manufacture, lightweight, and rugged for use by soldiers in combat situations.

In this example, photonic crystal structures that can be mass manufactured from continuous sheets of thin plastic film are provided as a laser eye shield technology. The photonic crystals can be designed to reflect any wavelength in the near UV, visible, or infrared spectrum, and can incorporate polymer materials that enable tuning of the reflected wavelength over a limited range. Photonic crystal structures can be designed and built that can actively respond to an external optical or electrical stimulus, so that tuning can occur in response to a detected laser threat. Because the photonic crystals are built from thin plastic films, it is possible to laminate structures designed for separate wavelength bands together to form composite devices that can handle multiple threat wavelengths.

The present example provides lightweight laser eye protection for soldiers, laser safety visors for airplane pilots, laser shielding for cockpit windows, and shielding for sensors used in laser guidance or infrared guidance weapon systems.

1.B Explanation of Planned Approach

Photonic crystals represent a new class of optical devices that have been enabled by recent advances in semiconductor fabrication tools with the ability to accurately deposit and etch materials with precision better than 100 nm. Along with the development of appropriate fabrication methods, accurate computer modeling tools are also becoming available which facilitate design of components with the ability to manipulate the propagation of light within a photonic crystal structure. Like the periodic arrangement of atoms within a semiconductor crystal that results in the formation of energy bands that control the conduction properties of electrons, the periodic arrangement of macroscopic dielectric media within a photonic crystal is designed to control the propagation of electromagnetic waves. Because the period of the structure is smaller than the wavelength of light, such devices are often referred to as "sub-wavelength surfaces" or as "nanostructured surfaces" because typical dimensions are 50-300 nm. Using photonic crystal design principles, one may construct devices with optical energy bands, which effectively prevent the propagation of light in specified directions and energies, while allowing concentration of electromagnetic field intensity within desired volumes and surfaces.

The applications of photonic crystal structures within the field of optoelectronics have been numerous, including integration with lasers to inhibit or enhance spontaneous emission, waveguide angle steering devices, and biosensors. Several device applications take advantage of the photonic crystal's capability for filtering an incident electromagnetic energy spectrum, including use as a narrowband reflectance filter.

The properties of photonic crystals make them ideal candidates for application as selective wavelength reflectance filters for application as a laser eye protection device:

First, the reflectance/transmittance behavior of a photonic crystal can be readily manipulated by the appropriate selection of the structure's period and by the selection of the high/low refractive index materials. Within robust design constraints, a photonic crystal can be designed as a highly efficient reflectance filter that, when illuminated with a broad band of wavelengths, can reflect back a narrow band of wavelengths with 100% reflection efficiency, while allowing all other wavelengths to pass through. With appropriate choice of the photonic crystal period, the highly reflected "resonant" wavelength can be designed to occur at nearly any wavelength from the ultraviolet to infrared. Further, the contrast between high and low refractive index materials and the structure geometry can be adjusted to obtain either very narrow reflected wavelength bands (~1 nm FWHM) or more broad wavelength bands (~10-20 nm FWHM). The reflection efficiency is inherent to the device structure, and therefore is always "on" without a need for externally supplied activation. Therefore, a static-wavelength photonic crystal reflector does not need to be concerned with switching speed or the energy of the threat laser required for activation.

Second, photonic crystal structures can be inexpensively produced on plastic substrate materials using highly efficient manufacturing techniques that can be performed on continuous sheets of film. Photonic crystal manufacturing is currently performed on a square yardage basis. Inexpensive structure manufacturing in a plastic sheet format enables vertical stacking of a plurality of photonic crystal structures designed to perform complimentary functions. For example, a 10-layer photonic crystal stack can be designed to selectively reflect a series of 10 threat laser wavelengths while allowing the soldier to see out through the visor at all remaining wavelengths. The thin-film manufacturing methods are currently performed using polyester and polycarbonate substrate materials that will result in visor/lens components that are lightweight, chemically inert, and mechanically robust.

Third, a photonic crystal reflectance filter can be designed to reflect efficiently over a wide range of incident angles. Using simple single photonic crystal structures, a reflection efficiency of >95% is maintained for incoming laser angles of up to 7 degrees. Using a system of vertically stacked photonic crystals to create a flat-top notch filter results in a predicted increase to 20 degrees.

Finally, the photonic crystal fabrication process is easily modified to include materials with the ability to quickly react to laser illumination, opening the possibility of creating structures with reflectance properties that can be tuned. For example, by applying a polymer incorporating a nonlinear dye material to the surface of the photonic crystal, it is possible to build a reflectance filter with a reflected wavelength that can be actively altered by exposure to the threat laser. Such a structure can be used to "close" an optical wavelength band that the visor had previously been left open, provided that the response time of the structure can be made rapid enough to protect the user's eye.

The present example provides methods for designing and fabricating photonic crystal structures for use as a laser eye protection shield. Single layer 1-dimensional photonic crystal structures designed to block a single wavelength is described. Single layer 2-dimensional photonic crystals are described that reflect light from a greater range of incident angles. Double layer photonic crystals are disclosed that provide a "flat top" reflection characteristic that is predicted to further extend the range of incident angle reflection over a wider range of laser wavelengths. Tunable wavelength structures incorporating nonlinear dye materials are described.

1.C Passive and Dynamic Photonic Crystal Based Devices

1.C(i) Static Wavelength Photonic Crystal Reflectance Filters

Computer simulations were conducted to study the reflection efficiency of photonic crystal reflectors as a function of incident light polarization and incident angle. A laser threat wavelength of 532 nm was selected as a design goal, although any threat wavelength within the visible, ultraviolet and/or infrared spectrum may be reflected by adjustment of the photonic crystal configuration. A Rigorous Coupled Wave Analysis (RCWA) software package (GSOLVER) was used to determine reflection characteristics for one-dimensional linear grating structures. RCWA provides a rapid approach for obtaining an exact solution to Maxwell's equations for periodic structures that can be specified with periodic features in one dimension, but is not readily capable of modeling structures with periodic variation in two dimensions. In RCWA, any incident polarization or angle of incidence can be specified. For two-dimensional photonic crystals, Finite Difference Time Domain (FDTD) methods with a commercially available software package (Lumerical) were used. FDTD is computationally intensive, but accurately predicts reflection characteristics at only normal incidence for periodic structures. Our design goal is to develop a structure that is capable of efficiently blocking a threat wavelength of any incident linear polarization and wavelength distribution over a wide range of incident angles.

Figure 19:
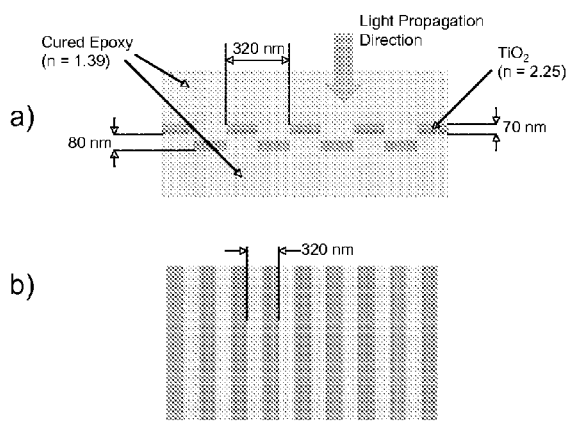
FIG. 19 is a cross section view (panel a) and top view (panel b) of a 1-dimensional photonic crystal reflector structure.
Figure 20:
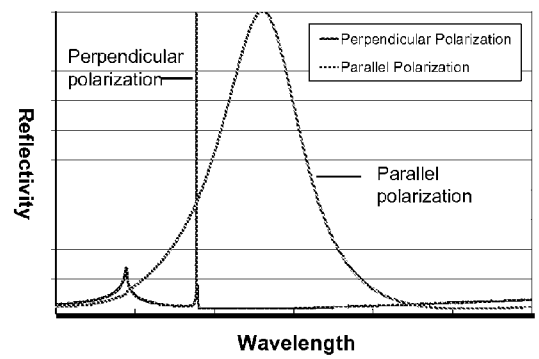
FIG. 20 is a RCWA-simulated reflectance spectrum (reflectance—Y axis; wavelength—X-axis) for the structure shown in FIG. 19, for incident light with electric field vector oriented perpendicular or parallel to the grating lines of the photonic crystal.

FIG. 19 is a cross section view (panel a) and top view (panel b) of a 1-dimensional photonic crystal reflector structure. FIG. 20 is a RCWA-simulated reflectance spectrum for the structure shown in FIG. 19, for incident light with electric field vector oriented perpendicular or parallel to the grating lines. Using the linear grating photonic crystal structure shown in FIG. 19 (19b. Top view, 19a Cross section view), RCWA was used to predict the reflection characteristic shown in FIG. 20, where a single sharp peak of 100% reflectivity is obtained at a wavelength of 530.5 nm for incident light with polarization parallel to the grating lines (TM polarization), and 489.1 nm for incident light with polarization perpendicular to the grating lines (TE polarization). FIG. 20 shows that a narrow peak is obtained for the TE case, and that a broad peak is obtained for the TM case, and that the peaks occur at different wavelengths.

Figure 21:
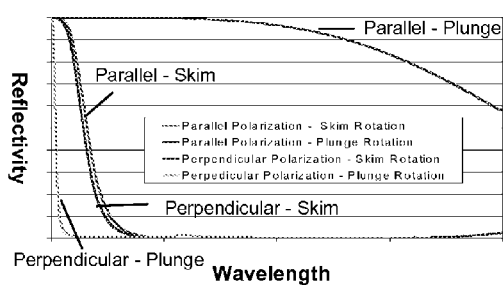
FIG. 21 is the RCWA simulation of reflection efficiency (Y-axis) as a function of angle (X-axis) at a wavelength of 527 nm for the structure shown in FIG. 19.
Figure 22:
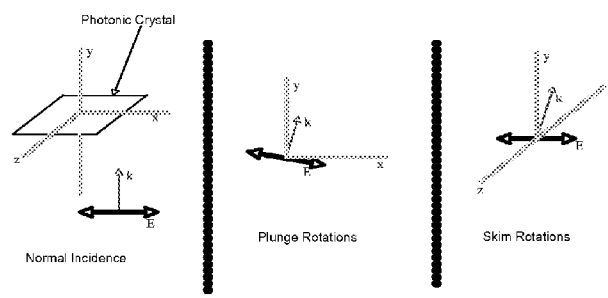
FIG. 22 is a schematic representation of the "skim" and "plunge" rotation orientations, as the two possible ways that the incident light may be oriented with respect to the photonic crystal surface.

FIG. 21 is the RCWA simulation of reflection efficiency as a function of angle at a wavelength of 527 nm for the structure shown in FIG. 19. The reflection efficiency as a function of incident angle for the TE and TM polarizations is shown in FIG. 21. Note that two different orientations of the incident angle with respect to the polarization direction are possible. FIG. 22 is a schematic representation of the "skim" and "plunge" rotation orientations, as the two possible ways that the incident light may be oriented with respect to the photonic crystal surface. As shown in FIG. 22, "skim rotation" occurs when the wave vector is rotated such that the electric field stays parallel to the plane of the photonic crystal (the x-z plane). The other case, referred to as "plunge rotation", occurs when the E-field vector has a component that is perpendicular to the photonic crystal plane. For a simple 1-dimensional photonic crystal, we observe that >95% reflection efficiency is maintained over a 10 degree angle of incidence only for the plunge rotation and parallel polarization of incident light.

FIG. 23 provides a schematic drawing of a cross sectional view (panel a) and top view (panel b) of a 2-dimensional photonic crystal reflector. Next, the 2-dimensional checkerboard photonic crystal structure shown in FIG. 23 (23a. Top view, 23b Cross section view) was analyzed by FDTD. FIG. 24 provides a plot of reflectivity as a function of wavelength for the 2-dimensional photonic crystal structure shown in FIG. 23. With the 2-dimensional structure, the TE and TM characteristics become equivalent, and a single, broad reflection peak is obtained at 526.9 nm, as shown in FIG. 24, for either polarization.

FIG. 25 provides a plot of reflectivity as a function of incident angle at a wavelength of 532 nm for the photonic crystal structure shown in FIG. 23. A wide range of reflected angle is obtained for one rotation orientation. The relationship between incident angle and reflection efficiency at the resonant wavelength was studied by RCWA, and is shown in FIG. 25 for the "plunge" and "skim" rotation angles. These results show that >95% reflection efficiency is provided over a range of 7 degree plunge rotation angle with a 2-dimensional photonic crystal structure.

These photonic crystal structures may be produced using a silicon "master" template wafer by electron-beam lithography containing the 1-d and 2-d patterns. In these techniques, the surface structure is replicated onto polyester film and overcoated with evaporated $TiO_2$.

1.C(ii) Double Layer Photonic Crystals for Flat-Top Reflectance Characteristic

A compound photonic crystal structure composed of two photonic crystal layers that are optically coupled may be used to provide a "flat-top" reflection characteristic around the threat wavelength with the ability to operate over a wider range of incident angles. FIG. 26 provides a cross sectional view of a multiple layer 1-dimensional photonic crystal structure designed to provide a "flat top" reflection characteristic. FIG. 27 provides a plot of reflectivity as a function of wavelength for the photonic crystal structure shown in FIG. 26. To demonstrate this concept, a 1-dimensional compound photonic crystal structure shown in FIG. 26 was studied by RCWA. FIG. 27 shows that a "flat top" reflection characteristic is obtained for the TM polarization over a 34.8 nm wide wavelength band (for >95% reflectance). The width of the band may be adjusted, as desired, by controlling the vertical separation and refractive index of the two periodic structures. FIG. 28 provides a plot of reflectivity as a function of incident angle at a wavelength of 532 nm for the photonic crystal structure shown in FIG. 26. The 2-layer structure exhibits >95% reflection efficiency over a 20 degree incident angle range in the plunge rotation direction, as shown in FIG. 28.

Compound photonic crystal structures, such as the one shown in FIG. 26, may be fabricated by first building single layer photonic crystals using the replication/$TiO_2$ evaporation technique described previously. The second layer is built on top of the first layer by deposition of a low refractive index material (such as $SiO_2$ or polymer) that maintains the corrugated surface structure, followed by deposition of a second $TiO_2$ film. As shown in FIG. 28, the double layer 1-dimensional photonic crystal structure provides excellent angle range for the "plunge" rotation direction, but only a limited range in the "skim" rotation direction. Excellent angular range for both rotation directions simultaneously may be obtained by a lens containing two such structures arranged with their grating lines oriented perpendicular to each other. Alternatively, a double layer 2-dimensional photonic crystal also provide acceptable angular rejection range for both rotation directions.

1.(C)(iii) Tunable Wavelength Photonic Crystal Reflectance Filters

By incorporating a material with variable refractive index or variable refractive index birefringence (i.e. different refractive index along two different electric field polarization directions) into the photonic crystal structure, the resonant reflected wavelength (i.e the photonic band gap) is adjustable. We describe 3 modes in which tunability of the photonic crystal wavelength can be utilized: 1). Single-time wavelength adjustment during the manufacturing process to customize the lens for a particular application. 2). Adjustment in the field to counter a particular known threat laser wavelength. 3). Real-time response to a threat laser when it illuminates the photonic crystal in order to close a band of wavelengths that had previously been open.

FIG. 29 (left panel) provides a cross sectional view of a single layer photonic crystal structure covered with a polymer film that incorporates refractive-index tunable azobenzene molecules. For light incident on the structure with an electric field vector oriented parallel to the grating lines, a $\Delta n=0.1$ birefringence is induced, resulting in a shift in the reflected wavelength. As a demonstration of the capability for wavelength tuning of a photonic crystal structure, a 2-dimensional structure, with cross-section shown in FIG. 29, was simulated by FDTD. The structure consists of a photonic crystal structure that is covered by a thin polymer film containing azobenzene-based nonlinear dye material. The elongated azobenzene molecules in their relaxed trans state may be preferentially aligned along any desired axis by exposure to a polarized laser beam with an electric field vector perpendicular to that axis. Aligned in this fashion, the azobenzene/polymer film will be birefringent, exhibiting different refractive indices for incident light polarized parallel or perpendicular to the molecule orientation. For azobenzene-based thin films, the difference in refractive index can be quite large (e.g., $\Delta n=0.1$). The refractive index of the birefringent film for a given incident light polarization can be altered by changing the orientation of the trans azobenzene molecules by exposure to a linearly polarized laser beam. The right panel of FIG. 29 shows plots of reflectivity as a function of wavelength for the device shown in the left panel of FIG. 29 in an unilluminated state and illuminated state. As shown in FIG. 29 (right panel), reorientation of the molecules by 90 degrees results in a predicted resonant reflected wavelength shift of up to 7.6 nm. Such tuning is simple and rapid, and can be applied to any of the photonic crystal lens designs herein.

Alternatively, a more rapid, but smaller refractive index change can be induced by exposure of the azobenzene/polymer film to the threat laser by the transition of the illuminated molecule from their relaxed trans state to their excited cis state. An at least 9 nm resonant wavelength shift that is not polarization dependent can be achieved using these azobenzene materials. Using photonic crystal device structures designed to maximize the response to a shift in bulk refractive index, a wavelength shift of 20 nm is as achievable.

The trans-cis transition can be used to design a tunable wavelength photonic crystal structure that is capable of reacting to the threat laser in order to close a wavelength band containing the threat wavelength.

Example 2

Optically Tunable Photonic Crystal Reflectance Filter

It is an objective of the present invention to provide dynamic photonic crystals having a tunable photonic band gap with a selectively adjustable frequency distribution. In this example, we demonstrate a photonic crystal structure whose properties are tunable with laser illumination through the incorporation of a nonlinear dye. Laser illumination causes a change in the bulk refractive index of the dye-doped portion of the structure, leading to controlled tuning of the photonic crystal reflectance spectrum. Changes in the refractive index of dye-doped regions are proportional to the intensity of the incident laser beam, and are as high as $\Delta n = 0.09$. The reflectance tuning effect is completely reversible upon termination of laser illumination.

2.A. Introduction

The nonlinear optical properties of azobenzene dyes have been extensively studied in recent years. These materials are very attractive due to the fact that large changes in the refractive index can be achieved for relatively low illumination intensities, compared to more traditional nonlinear optical materials. Azobenzene-containing polymers have been used extensively in research pertaining to all-optical switching and optical data storage.

It is very well established that there are two primary mechanisms of refractive index change in azobenzene-containing polymers. The first mechanism is photon-induced excitation of the azobenzene molecule from the lower-energy trans state to the excited cis state. Since the cis isomer is bent and much more compact than the elongated trans isomer, increasing the fraction of cis state molecules will result in a net decrease in the optical density of the dye-polymer system. The second mechanism of refractive index change in these polymers is a photoinduced birefringence caused by large-scale alignment of elongated trans state azobenzene molecules along the direction perpendicular to the polarization of excitation light. Trans state molecules that are oriented perpendicular to the electric field vector of the incident light beam are thought to not participate in photon absorption, and thus will not be excited into the cis state, causing them to remain oriented perpendicular to the light polarization. However, trans state molecules that are excited into the cis state will eventually relax back to the trans state, with the orientation of each trans state molecule being effectively random upon relaxation. Thus, over a period of continuous illumination, many cis state molecules will randomly relax to a trans state that is perpendicular to the electric field, and thus be removed from the pool of excitable molecules. Eventually, a significant fraction of the azobenzene molecules will be oriented perpendicular to the electric field, leading to an increase in optical density along the direction of molecular alignment and a decrease in optical density along the direction of the electric field. Values of photoinduced birefringence as high as $\Delta n = 0.13$ have been reported for amorphous azobenzene-containing polymers. For liquid crystalline polymers, values as high as $\Delta n = 0.28$ have been reported. Since the photoinduced birefringence effect relies on many excitation-relaxation cycles, it is the slower of the two mechanisms of refractive index change in azobenzene-containing polymers. In addition, photoinduced birefringence is not observed in systems that do not preserve orientation, such as a dye-solvent solution.

Photonic crystals have also been vigorously studied in recent years. Photonic crystal structures consist of alternating regions of high and low refractive index materials, and are characterized by a photonic band gap. The periodic dielectric structure leads to the formation of a photonic band gap in much the same way that the periodic atomic potential of a semiconductor leads to the formation of electronic band gaps. Photonic crystals can be fabricated with one, two, or three dimensions of periodicity. Through careful selection of materials and structure dimensions, the optical properties of photonic crystals can be engineered for specific applications. Numerous practical applications of photonic crystals are already in widespread use, including in optical fibers, tunable coupled-cavity edge-emitting semiconductor lasers, vertical cavity surface emitting lasers, optical biosensors, and slab line-defect waveguides. The most basic one-dimensional photonic crystal, the thin film quarter-wave stack, or distributed Bragg reflector, had been in practical use for many years before photonic crystal formalism was developed. Another one-dimensional photonic crystal, a dielectric grating surface structure, is the structure of interest in the present work.

Figure 30:
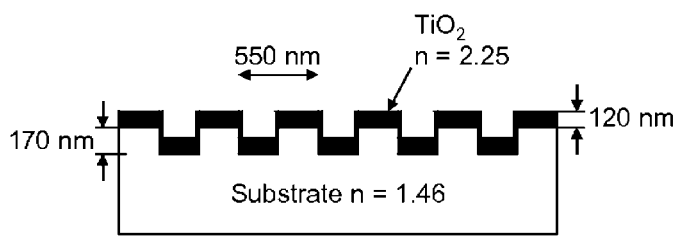
FIG. 30 shows a cross sectional view of a one-dimensional photonic crystal reflectance filter.

In this example, we report on the fabrication and characterization of a photonic crystal whose reflectance spectrum is tunable through the incorporation of an azobenzene dye. FIG. 30 shows a cross sectional view of a one-dimensional photonic crystal reflectance filter. The device, shown in FIG. 30, consists of a one-dimensional periodic surface structure fabricated on a low refractive index plastic substrate that is overcoated with a layer of high refractive index $TiO_2$. Directly above the layer of $TiO_2$, in the "superstrate" region, we have applied a dye-doped polymer and a dye-solvent solution. When the fabricated structure is illuminated with broadband light at normal incidence with the light polarization perpendicular to the grating lines, a narrow band of wavelengths is strongly reflected. We have demonstrated that upon laser illumination, the wavelength of the reflection resonance can shift to lower wavelengths by >15 nm, and that the resonance returns to its original wavelength when laser illumination is turned off. For the resonance tuning effect to be achieved, the wavelength of the laser must be within the absorption spectrum of the dye. We have characterized the switching speed and dependence of the magnitude of the shift on laser intensity. Because the switching behavior is largely independent of the polarization of the incident laser beam, the dominant mechanism for refractive index change is likely the trans-cis excitation of dye molecules in the dye-doped superstrate region. Numerical simulations show that the magnitude of the bulk refractive index change in the dye-doped region is as large as $\Delta n = 0.09$.

2.B. Device Design and Fabrication

FIG. 30 provides a schematic diagram of a one-dimensional periodic surface structure fabricated on a low refractive index plastic substrate that is overcoated with a thin film of high refractive index $TiO_2$. Directly above the $TiO_2$ film, in the "superstrate" region, we have applied an azobenzene dye embedded in a solid polymethylmethacrylate (PMMA) polymer and also in a solution of isopropyl alcohol (IPA). Dimensions of period, step height, and $TiO_2$ thickness are approximately 550 nm, 170 nm, and 120 nm, respectively. In addition, the sidewalls of the grating steps are covered by approximately 10 nm of $TiO_2$. The refractive indices (at a wavelength of 850 nm) of the substrate and $TiO_2$ are 1.46 and 2.25, respectively, and the refractive index of the superstrate is tunable through laser illumination. These structures can be fabricated inexpensively on continuous rolls of plastic film. For this work, the plastic substrate has been adhered to a standard glass microscope slide for ease of handling.

Figure 31:
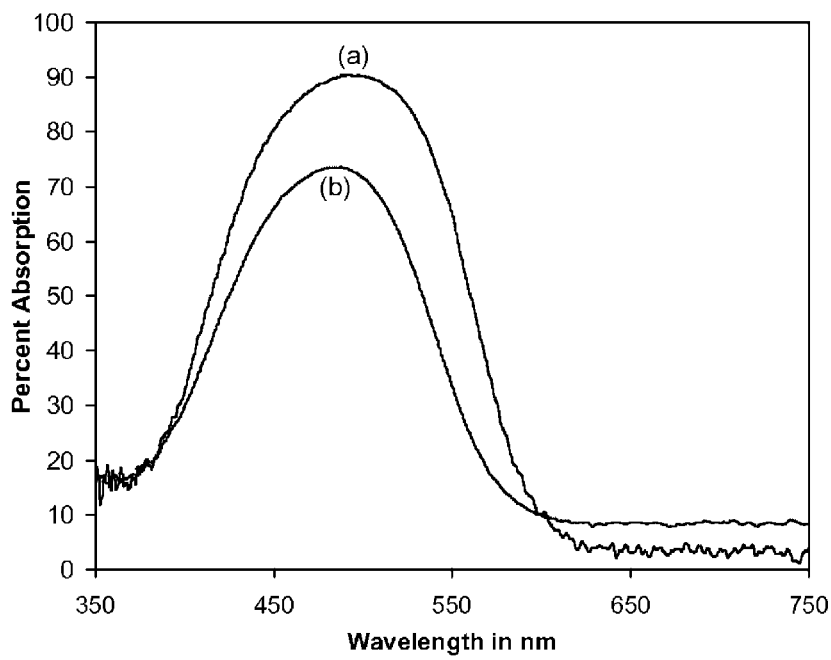
FIG. 31(a) shows the absorption spectrum for 1.5 um thick polymer film containing 5% Disperse Red 1 and 95% PMMA by weight, spun onto a blank glass microscope slide. The wavelength of maximum absorption was measured to be at 492 nm.
FIG. 31(b) shows the absorption spectrum for a saturated solution of Disperse Red 1 in IPA occupying the thin layer between a microscope slide and a cover slip.

We utilized two different superstrate materials in the present study: dye-doped PMMA and dye-doped IPA. For the dye, we have chosen to work with the azobenzene molecule N-Ethyl-N-(2-hydroxyethyl)-4-(4-nitrophenylazo)aniline (known informally as Disperse Red 1, or DR1), since it has been thoroughly studied by many authors and is readily available (SigmaAldrich). The fabrication procedure for the samples incorporating a DR1-doped PMMA superstrate is as follows: 0.05 grams of DR1 was dissolved in 3 mL chloroform, and heated to approximately 60° C., stirring occasionally. In addition, 0.95 grams of PMMA powder (SigmaAldrich, MW~120,000) was dissolved in 8 mL chloroform, and heated to 60° C., stirring occasionally. After both DR1 and PMMA had completely dissolved in their chloroform solutions, they were mixed together and stirred for 15 minutes. This solution was allowed to cool to room temperature, and was then spin coated onto a photonic crystal using a 2000 RPM spin for 30 seconds. After the spin, most of the solvent had been driven off, leaving a solid film of thickness 1.5 microns, as measured on an AlphaStep surface profiler. FIG. 31 (a) shows the absorption spectrum for 1.5 um thick polymer film containing 5% Disperse Red 1 and 95% PMMA by weight, spun onto a blank glass microscope slide. The wavelength of maximum absorption was measured to be at 492 nm. FIG. 31(b) shows the absorption spectrum for a saturated solution of Disperse Red 1 in IPA occupying the thin layer between a microscope slide and a cover slip. In this case, the wavelength of maximum absorption is 487 nm.

To construct the samples incorporating a superstrate of dye-doped IPA, 0.05 grams of DR1 was dissolved in 10 mL IPA, resulting in a saturated solution. Next, a microscope cover slip was placed directly on top of the photonic crystal surface. A few drops of DR1-IPA solution were placed around the edges of the cover slip, which allowed the solution to spread across the photonic crystal surface through capillary action. Finally, the solution was sealed underneath the cover slip by placing a bead of Duco cement around the edges of the cover slip. We estimate the depth of the DR1/IPA solution underneath the cover slip to be 5-10 microns.

2.C. Numerical Simulations and Device Characterization

Numerical simulations of the photonic crystal structure were performed using Rigorous Coupled Wave Analysis (RCWA). The RCWA method, first reported by M. G. Moharam and T. K. Gaylord in 1981, provides an exact solution of Maxwell's equations for periodic diffracting structures. In this work, we utilized a commercially available implementation of the RCWA technique (DiffractMOD, RSoft Corporation).

Figure 32:
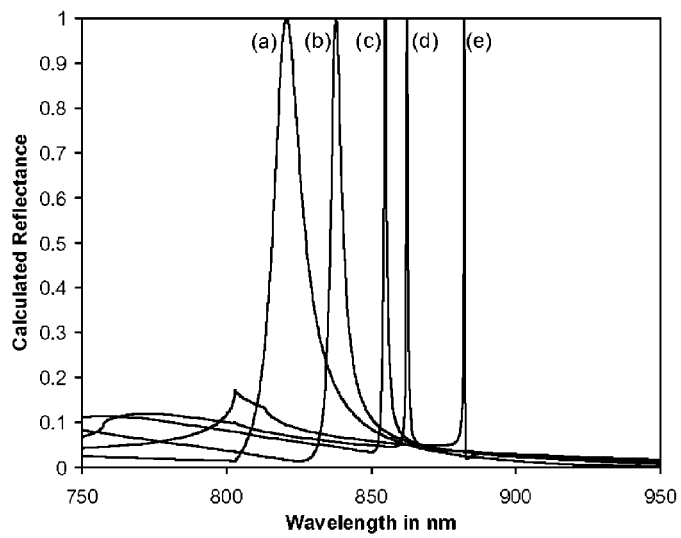
FIG. 32 shows calculated normal-incidence reflectance spectra for 5 different values of the superstrate refractive index: (a) 1.00, (b) 1.20, (c) 1.333, (d) 1.377, and (e) 1.479.
Figure 33:
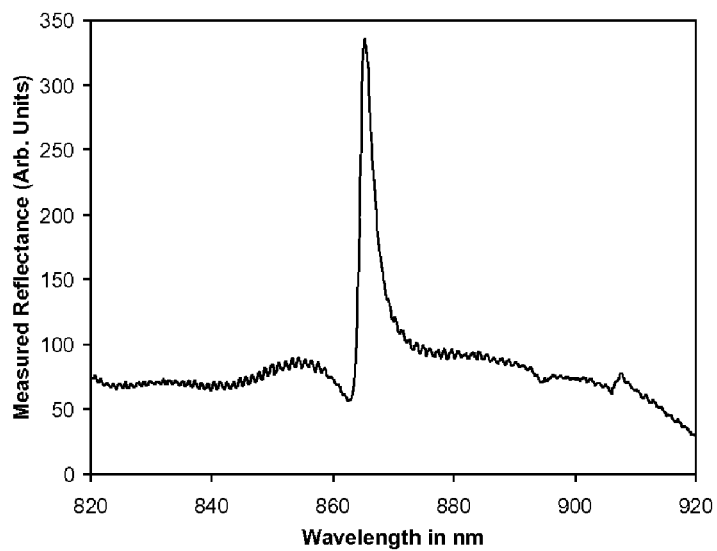
FIG. 33 shows a normal-incidence reflection spectrum for a photonic crystal structure with an IPA superstrate.
Figure 34:
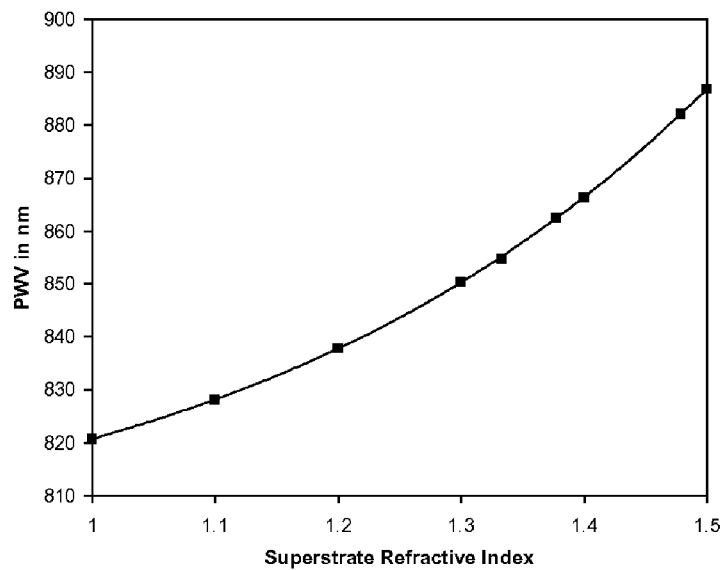
FIG. 34 provides plotted points indicating the calculated spectral location of reflection peaks for several different superstrate material refractive indices.

For simulation, it is assumed that an electromagnetic plane wave propagating in the −z direction is normally incident to the photonic crystal structure. The polarization of the wave is such that the electric field vector is perpendicular to the grating lines. To calculate a useful reflectance spectrum, the simulation is run for incident wavelengths between 750 nm and 950 nm, with a computation interval of 0.1 nm. A full reflection spectrum has been calculated for 9 values of the superstrate refractive index. These 9 values correspond to different materials that could be utilized for the superstrate. We have calculated reflectance spectra for superstrate refractive indices of 1.00, 1.333, 1.377, and 1.479, corresponding to the refractive indices of air, water, IPA, and dimethyl sulfoxide (DMSO). For instructional purposes, we have also calculated reflectance spectra for superstrate refractive indices of 1.10, 1.20, 1.30, 1.40, and 1.50, which do not necessarily correspond to actual materials. FIG. 32 shows calculated normal-incidence reflectance spectra for 5 different values of the superstrate refractive index: (a) 1.00, (b) 1.20, (c) 1.333, (d) 1.377, and (e) 1.479. As can be seen from FIG. 32, the predicted spectral location of the reflection peak strongly depends on the superstrate refractive index. Reflectance spectra have been measured for photonic crystal structures with superstrates of air, water, IPA, and DMSO. FIG. 33 shows a normal-incidence reflection spectrum for a photonic crystal structure with an IPA superstrate. With an IPA superstrate, the reflection peak has a FWHM of 4 nm and is located at 865.3 nm. In the figures and table, we will refer to the spectral location of the reflection peak as the "peak wavelength value", or PWV. Table 1 shows a comparison between the calculated and measured reflection peak locations for 4 different superstrate materials. Agreement between the theoretical model and measured values is excellent, with the largest deviation being 0.3%, which occurs for the samples with an IPA superstrate. The purpose of these calculations and measurements is to develop a model of the sensitivity to refractive index changes for the photonic crystal structure. FIG. 34 provides plotted points indicating the calculated spectral location of reflection peaks for several different superstrate material refractive indices. The continuous curve is a best-fit third order polynomial, with R2=1. In FIG. 34, a third-order polynomial is fit to the 9 calculated data points of PWV vs. superstrate refractive index. The relation between PWV and superstrate index for this structure is very accurately approximated by the following relationship, where PWV is in units of nm, and n is the superstrate refractive index.

$$PWV=122.07n^3-295.11n^2+290.12n+703.61$$

TABLE 1

Measured and Calculated Peak Locations

| Superstrate Refractive Index | Measured PWV (nm) | Calculated PWV (nm) |
|---|---|---|
| 1.000 | 820.6 | 820.7 |
| 1.333 | 856.1 | 854.8 |
| 1.377 | 865.3 | 862.4 |
| 1.479 | 881.9 | 882.1 |

2.D. Apparatus Description

Figure 35:
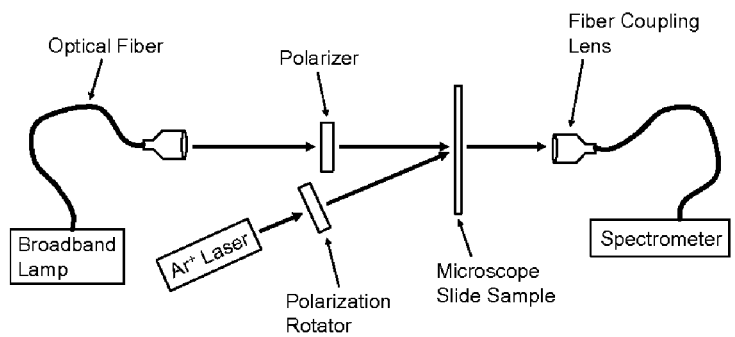
FIG. 35 provides a schematic diagram showing the apparatus used to induce and measure changes in the photonic crystal reflection spectrum.

FIG. 35 provides a schematic diagram showing the apparatus used to induce and measure changes in the photonic crystal reflection spectrum. As shown in FIG. 35, we utilized a pump-probe style apparatus. A nearly-collimated broadband probe beam is normally incident to the photonic crystal sample. Broadband light for the probe beam originates from a fiber-coupled tungsten-halogen lamp (LS-1, Ocean Optics), and a 200 μm diameter optical fiber connects the light source to a fiber collimating lens (74-UV, Ocean Optics). A polarizing filter is situated in between the collimating lens and the sample, so that probe beam light is polarized perpendicularly to the grating lines of the sample. After transmission through the sample, probe beam light is collected through a collimating lens and sent through a 200 um diameter optical fiber to a fiber-coupled spectrometer (USB2000, Ocean Optics). A complete photonic crystal transmission spectrum is obtained every 20 ms during active measurement. The pump beam strikes the sample at a 22.5 degree angle, and originates from an argon-ion laser (Innova 90, Coherent). In this work, we utilized the 488.0 nm, 496.5 nm, and 501.7 nm lines from the argon-ion laser, which are all strongly absorbed by DR1 molecules. The 501.7 nm line was used for illumination powers of 5 mW-124 mW, the 496.5 nm line was used for illumination powers of 150 mW-450 mW, and the 488.0 nm line was used for illumination powers of 500 mW-1000 mW. The laser beam is not focused, and has a 3 mm diameter spot size on the sample. This allows the probe beam and pump beam to completely overlap spatially, and also allows a significant area of the photonic crystal surface to be utilized.

2.F. Results

Figure 36:
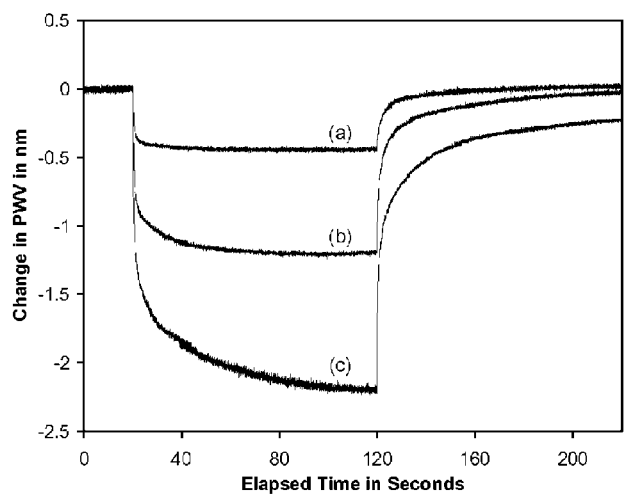
FIG. 36 provides plots of the measured change in spectral location of the reflection peak of the DR1/PMMA-superstrate sample as a function of time for incident laser powers of (a) 10 mW, (b) 62 mW, and (c) 124 mW.
Figure 37:
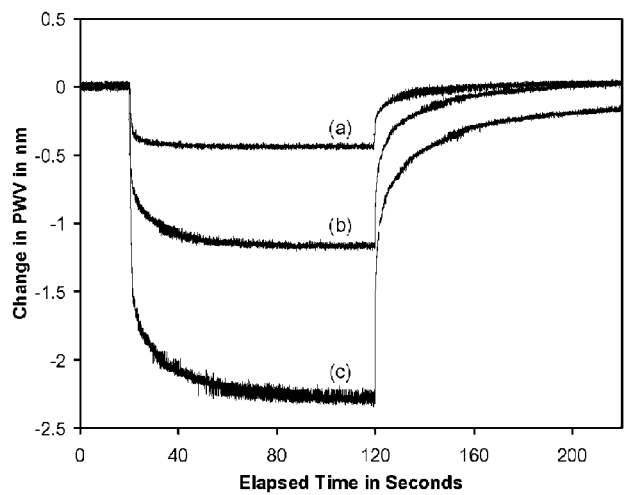
FIG. 37 provides plots of measured change in spectral location of the reflection peak of the DR1/PMMA-superstrate sample as a function of time for incident laser powers of (a) 10 mW, (b) 62 mW, and (c) 124 mW.

FIG. 36 provides plots of the measured change in spectral location of the reflection peak of the DR1/PMMA-superstrate sample as a function of time for incident laser powers of (a) 10 mW, (b) 62 mW, and (c) 124 mW. Vertically polarized laser illumination was initiated at an elapsed time of 20 seconds and was terminated at 120 seconds. FIG. 37 provides plots of measured change in spectral location of the reflection peak of the DR1/PMMA-superstrate sample as a function of time for incident laser powers of (a) 10 mW, (b) 62 mW, and (c) 124 mW. Horizontally polarized laser illumination was initiated at an elapsed time of 20 seconds and was terminated at 120 seconds.

Figure 38:
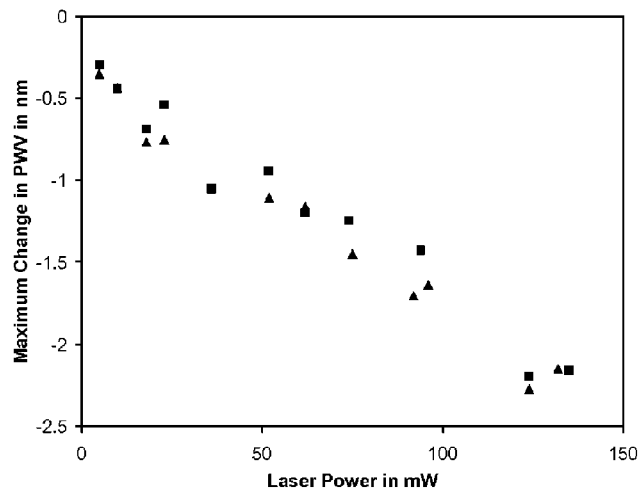
FIG. 38 provides a plot of maximum change in the spectral location of the reflection peak for the DR1-PMMA sample at several values of laser illumination power. Squares indicate vertical laser polarization, and triangles correspond to horizontal laser polarization.

FIGS. 36 and 37 show the change in the reflection peak wavelength as a function of time at 3 laser intensities for the photonic crystal coated with the 5% DR1/95% PMMA polymer film. The data presented in FIG. 36 was obtained through the use of vertically polarized laser light (laser polarization parallel to photonic crystal grating lines), whereas FIG. 37 is for the case of horizontally polarized laser light. Laser illumination was initiated at t=20 seconds and was terminated at t=120 seconds. Maximum reflection peak tuning of −2.2 nm is achieved at the maximum laser power of 124 mW (which corresponds to an intensity of 1.75 W/cm$^2$). This magnitude of tuning corresponds to a change in the superstrate refractive index of $\Delta n \approx -0.01$, as determined from the photonic crystal sensitivity relationship discussed in Section 3. FIG. 38 provides a plot of maximum change in the spectral location of the reflection peak for the DR1-PMMA sample at several values of laser illumination power. Squares indicate vertical laser polarization, and triangles correspond to horizontal laser polarization. In FIG. 38, the maximum change in reflection peak location is plotted as a function of the laser power. In the figure, square data points indicate vertical laser polarization, and triangles indicate horizontal laser polarization. FIG. 38 shows that the maximum reflection peak shift varies nearly linearly with the laser power over this range of powers. It should be noted that laser powers larger than 124 mW were not used on this sample, since the effects of photobleaching of the dye begin to become significant for powers larger than this. Photobleaching is the result of photon-induced damage to the dye molecules, and is characterized by a permanent decrease in the refractive index of the dye-polymer system.

Figure 39:
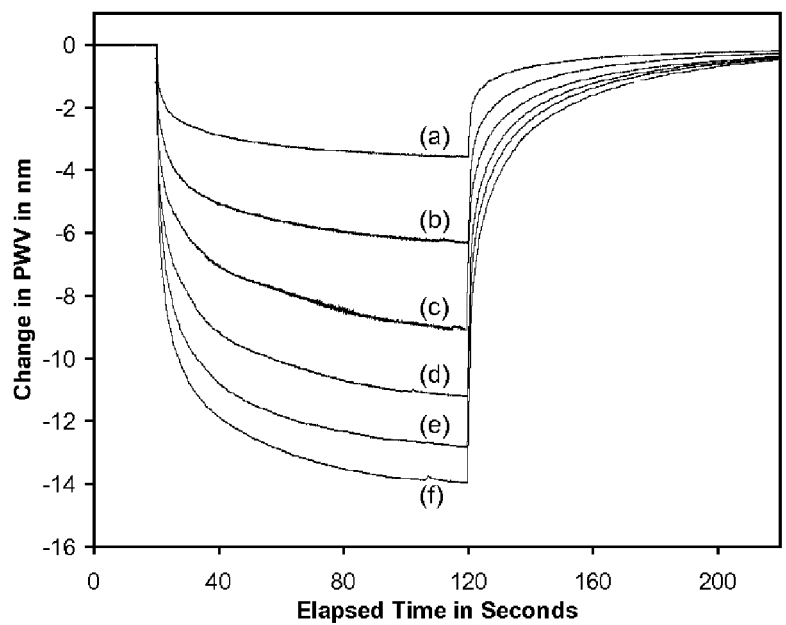
FIG. 39 provides a plot of measured change in spectral location of the reflection peak as a function of time for DR1-IPA sample at incident laser powers of (a) 100 mW, (b) 200 mW, (c) 300 mW, (d) 400 mW, (e) 500 mW, and (f) 600 mW.
Figure 40:
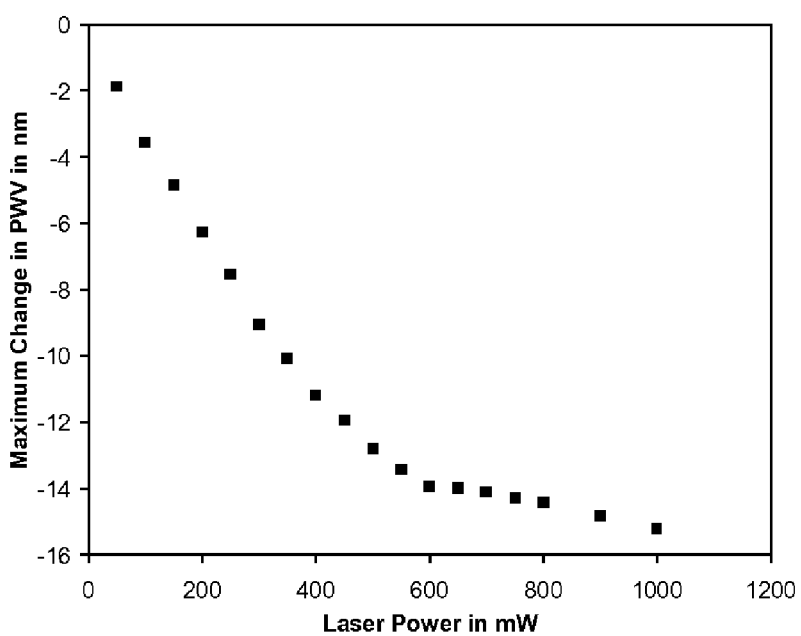
FIG. 40 provides plots of the maximum change in the spectral location of the reflection peak of the DR1-IPA sample at several intensities of horizontally polarized laser illumination.

In contrast, photonic crystal samples that utilized the saturated solution of DR1 in IPA as the nonlinear material showed complete resistance to photobleaching. Thus, we were able to perform the characterization for laser powers as high as 1000 mW (intensities as large as 14 W/cm$^2$) with no observable damage to the nonlinear material. FIG. 39 provides a plot of measured change in spectral location of the reflection peak as a function of time for DR1-IPA sample at incident laser powers of (a) 100 mW, (b) 200 mW, (c) 300 mW, (d) 400 mW, (e) 500 mW, and (f) 600 mW. Horizontally polarized laser illumination was initiated at an elapsed time of 20 seconds and was terminated at 120 seconds. FIG. 39 shows the change in peak reflection wavelength as a function of time for several intensities of horizontally polarized laser illumination. Once again, laser illumination begins at time t=20 seconds and is terminated at time t=120 seconds. Maximum reflection peak tuning of −15.2 nm is achieved at the maximum laser power of 1000 mW. This magnitude of tuning corresponds to a change in the superstrate refractive index of $\Delta n \approx -0.09$. FIG. 40 provides plots of the maximum change in the spectral location of the reflection peak of the DR1-IPA sample at several intensities of horizontally polarized laser illumination. In FIG. 40, maximum reflection peak shift is plotted versus laser power. For laser powers in between 50 mW and 500 mW, the relationship between maximum peak tuning and laser power is quite linear. However, for laser powers of 600 mW and higher, there appears to be some saturation of the index-change effect.

2.G. Discussion

For the samples utilizing a DR1/PMMA superstrate, it is clear that the tuning behavior for the case of vertical laser polarization (FIG. 36) is very similar to the case of horizontal laser polarization (FIG. 37). This suggests that the dominant mechanism of refractive index change is the trans-cis excitation, rather than photoinduced birefringence. At the onset of laser illumination, many trans-isomer dye molecules in the polymer film are excited to the cis-isomer state, causing a decrease in the refractive index in the polymer film, and thus leading to a shift towards smaller wavelengths in the spectral location of the photonic crystal reflection peak. Then, upon termination of laser illumination, the excited state cis-isomers undergo thermal relaxation back to the trans-isomer state, causing the refractive index of the polymer film to return to its initial value, and thus the reflection peak wavelength returns to its initial value. In contrast, if photoinduced birefringence were the dominant mechanism of refractive index change, then we would expect significant differences in tuning behavior between the two laser polarizations. Indeed, for other dye-polymer systems, we have observed the reflection peak wavelength to increase when laser polarization is parallel to the grating lines, with a decrease for the case of laser polarization perpendicular to the grating lines. However, it should be noted that upon careful inspection, minor differences between FIG. 36(c) and FIG. 37(c) are evident, particularly in the transition rate. In FIG. 36(c), for the case of vertical laser polarization, the downward transition is more gradual than the downward transition in FIG. 37(c). It is possible that this difference can be explained by the presence of a small amount of photoinduced birefringence. Horizontally polarized laser light should cause some of the dye molecules to become oriented parallel to the grating lines, which would reinforce the tendency for the reflection peak location to shift downward in wavelength. Conversely, vertically polarized laser light should cause some of the dye molecules to become oriented perpendicularly to the grating lines, which would provide a tendency toward an upward shift in the reflection peak wavelength. In this case, however, photoinduced birefringence is a minor effect, and thus for the case of vertical laser polarization, photoinduced birefringence merely acts to slightly counteract the tendency towards a downward shift in reflection peak wavelength. For the case of horizontal laser polarization, photoinduced birefringence acts to slightly reinforce the tendency towards a downward shift in the spectral location of the reflection peak.

Upon comparing FIGS. 36 and 37 to FIG. 39, it is clear that the tuning behavior for the DR1/PMMA samples is very similar to that of the DR1/IPA samples. In particular, the dominant mechanism of refractive index change in the DR1/IPA samples is the trans-cis excitation of dye molecules. This is certainly to be expected, as the liquid solvent does not allow for long-term alignment of trans-state dye molecules. In low-viscosity solutions such as IPA, small molecules are known to diffuse rotationally within a few picoseconds. Thus, there is not any appreciable photoinduced birefringence, and one can be quite certain that the refractive index change is caused by the trans-cis excitation. Indeed, we observed that the reflection peak tuning behavior for horizontally polarized laser illumination was identical to the tuning behavior for the case of vertically polarized laser illumination. Thus, in the interest of conciseness, we only present data for the case of horizontal laser polarization.

As mentioned previously, FIG. 40 shows that there is some saturation of the index-change effect for laser powers of 600 mW and greater for the samples utilizing a DR1/IPA superstrate. For laser powers larger than 600 mW, further increases in illumination power do not yield significant additional shifting of the reflection peak. We interpret this to mean that most of the available dye molecules are in the excited cis state at an illumination power of 600 mW. Although there appears to be an obvious saturation point at 600 mW, careful inspection of FIG. 40 shows that there is still a small amount of additional shifting as the laser power is further increased. For illumination powers greater than the 600 mW saturation point, it is possible that the small amounts of observed additional shifting are caused by heating of the sample.

2.H. Conclusion

We have demonstrated a one-dimensional photonic crystal whose reflectance spectrum is tunable with laser illumination through the incorporation of a nonlinear azobenzene dye into the photonic crystal structure. Laser illumination causes a change in the refractive index of the dye-doped region of the structure, leading to controlled tuning of the photonic crystal reflectance spectrum. The spectral location of the primary reflection feature was shifted by >15 nm, and the shift is completely reversible upon termination of laser illumination. Numerical simulations show that this level of tuning corresponds to a refractive index change of $\Delta n=0.09$ in the dye-doped region. The tunable photonic crystals of this example provide key functional components in optical switching and multiplexing, and laser modulation systems of the present invention.

We claim:

1. An optical device for protecting an eye or sensor from incident electromagnetic radiation generated by a laser; said device comprising;

a first photonic crystal having a spatial distribution of refractive indices that varies periodically in at least two dimensions and positioned to intersect said electromagnetic radiation generated by a laser, said first photonic crystal comprising a dielectric structure comprising alternating high refractive index elements and low refractive index elements provided in a periodic spatial configuration in at least two dimensions, and said photonic crystal having a photonic band gap, wherein said incident electromagnetic radiation generated by said laser has a first range of frequencies, wherein the spatial distribution of refractive indices of said first photonic crystal and the refractive indices of said high and low refractive index elements are selected such that the photonic band gap of said first photonic crystal at least partially overlaps said first range of frequencies of said incident electromagnetic radiation generated by said laser; and wherein said first photonic crystal is a component of said optical device positioned to prevent transmission of substantially all of said incident electromagnetic radiation generated by said laser through said device to said eye or said sensor.

2. The device of claim 1 wherein said dielectric structure comprises high refractive index elements and low refractive index elements provided in a spatial configuration that is periodic in at least two lateral directions, wherein said lateral directions are not parallel to the propagation axes of said electromagnetic radiation from said laser.

3. The device of claim 1 wherein said dielectric structure comprises high refractive index elements and low refractive index elements provided in a spatial configuration that is periodic in at least two lateral directions, wherein said lateral directions are orthogonal to the propagation axes of said electromagnetic radiation from said laser.

4. The device of claim 1 wherein said laser provides a beam of electromagnetic radiation that is incident upon a receiving surface of said first photonic crystal; wherein said dielectric structure comprises high refractive index elements and low refractive index elements provided in a spatial configuration that is periodic in at least two lateral directions, wherein said lateral directions are parallel to said receiving surface.

5. The device of claim 1 wherein said dielectric structure comprises a two-dimensional periodic array of said alternating high refractive index elements and low refractive index elements.

6. The device of claim 1 wherein said low refractive index elements comprise a polymeric material.

7. The device of claim 1 wherein said high refractive index elements comprise thin dielectric films.

8. The device of claim 1 further comprising a substrate having alternating raised and recessed relief features provided in a periodic configuration, wherein said high refractive index elements are disposed on top of said raised and recessed relief features of said substrate, and wherein at least a portion of said low refractive index elements are said raised f aturo features of said substrate.

9. The device of claim 8 wherein said substrate comprises a polymeric material.

10. The device of claim 1 further comprising a superstrate having alternating raised and recessed relief features provided in a periodic configuration, wherein said superstrate is in contact with at least a portion of said high refractive index elements, and wherein at least a portion of said low refractive index elements are said raised relief features of said superstrate.

11. The device of claim 10 wherein said superstrate comprises a polymer material.

12. The device of claim 1 further comprising a second photonic crystal positioned in optical communication with said first photonic crystal and positioned to intersect said electromagnetic radiation generated by a laser; said second photonic crystal having a spatial distribution of refractive indices that varies periodically in at least two dimensions and comprising a dielectric structure comprising alternating high refractive index elements and low refractive index elements provided in a periodic spatial configuration in two dimensions, and said second photonic crystal having a photonic band gap.

13. The device of claim 12 wherein said band gap of said second photonic crystal has a different photonic band gap frequency distribution than that of said band gap of said first photonic crystal.

14. The device of claim 12 wherein the second photonic crystal is separated from said first photonic crystal by a separation layer, said separation layer having a substantially uniform thickness, thereby maintaining a selected optical pathlength between said first photonic crystal and said second photonic crystal for incident electromagnetic radiation having a given angle of incidence.

15. The device of claim 14 wherein said optical pathlength between said first photonic crystal and said second photonic crystal is sufficiently small to provide optical coupling of electromagnetic radiation diffracted by said first photonic crystal and said second photonic crystal.

16. The device of claim 14 wherein said first photonic crystal and said second photonic crystal have substantially the same spatial distributions of refractive indices that vary periodically in at least two dimensions.

17. The device of claim 14 wherein said first photonic crystal and said second photonic crystal have different spatial distributions of refractive indices that vary periodically in at least two dimensions.

18. The device of claim 14 wherein said separation layer comprises a polymeric material.

19. The device of claim 14 wherein said first photonic crystal has a first optical axis and said second photonic crystal has a second optical axis that is offset relative to said first optical axis of said first photonic crystal.

20. The device of claim 19 wherein said second optical axis is offset relative to said first optical axis of said first photonic crystal by about 45 degrees.

21. The device of claim 14 wherein said low refractive index elements, high refractive index elements or both of said second photonic crystal comprise a photodynamic polymer having a selectively variable refractive index that changes upon exposure to said electromagnetic radiation generated by a laser.

22. The device of claim 21 wherein said photodynamic polymer comprises a dye material embedded in a polymer matrix.

23. The device of claim 21 wherein said dye material comprises an azobenzene molecule.

24. The device of claim 23 wherein said azobenzene molecule is selected from the group consisting of:
N-ethyl-N-(2-hydroxyethyl)-4-(4 nitrophenylazo)aniline;
4-(dimethylamino)azobenzene; and
2-(4-Dimethylaminophenylazo)benzoic acid.

25. The device of claim 22 wherein said dye material is selected from the group consisting of: (2,6-Dimethyl-4H-pyran-4-ylidene)malononitrile; (S)-(−)-1-(4-Nitrophenyl)-2-pyrrolidinemethanol; [4-[Bis(2-hydroxyethyl)amino]phenyl]-1,1,2-ethylenetricarbonitrile; 1-Docosyl-4-(4-hydroxystyryl)pyridinium bromide; 2-(Dimethylamino) vinyl-1-nitronaphthalene; 2,3,5,6-Tetrafluoro-7,7,8,8-tetracyanoquinodimethane; 2-[[5-(Dibutylamino)-2-thienyl] methylene]-1H-indene-1,3(2H)-dione; 2-[4-((4-(Bis(2-hydroxyethyl)amino]phenyl)(cyano)methylene]-2,5-cyclohexadien-1-ylidene]malonitrile; 2-[4-(Dimethylamino) styryl]pyridine; 2-[Ethyl[4-[2-(4-nitrophenyl)ethenyl] phenyl]amino]ethanol; 2-Amino-3-nitropyridine; 2-Amino-5-nitropyridine; 2-Aminofluorene; 2-Chloro-3,5-dinitropyridine; 2-Chloro-4-nitroaniline; 2-Nitroaniline; 3-[(4-Nitrophenyl)azo]-9H-carbazole-9-ethanol; 3-Methyl-4-nitropyridine N-oxide; 3-Nitroaniline; 4-(Dibenzylamino) benzaldehyde-N,N-diphenylhydrazone; 4-[4-(Dimethylamino)styryl]-1-docosylpyridinium bromide; 4-[4-(Dimethylamino)styryl]pyridine; 4-Dimethylamino-4'-nitrostilbene; 4-Nitroaniline; 5-Nitroindole; 5-Nitrouracil; 7,7,8,8-Tetracyanoquinodimethane; 9-Ethyl-3-carbazolecarboxaldehyde-N-methyl-N-phenylhydrazone; 3-[N-Ethyl-4-(4-nitrophenylazo)phenylamino]propionitrile (Disperse Orange 25); 4-(4-Nitrophenylazo)aniline (Disperse Orange 3); N-Ethyl-N-(2-hydroxyethyl)-4-(4-nitrophenylazo) aniline (Disperse Red 1); 2-[4-(2-Chloro-4-nitrophenylazo)-N-ethylphenylamino]ethanol (Disperse Red 13); Disperse Red 19; 4-[4-(Phenylazo)phenylazo]-o-cresol (Disperse Yellow 7); Ethyl 4-(dimethylamino)benzoate; Hexamethylpararosaniline chloride (Crystal Violet); N-(2,4-Dinitrophenyl)-L-alanine methyl ester; N,N-Dimethyl-N'-[(5-nitro-2-thienyl)methylene]-1,4-phenylenediamine; N-[3-Cyano-3-[4-(dicyanomethyl)phenyl]-2-propenylidene]-N-ethylethaniminium; Nile Blue A (Basic Blue 12); N-Methyl-4-nitroaniline; trans-4-[4-(Dimethylamino)styryl]-1-methylpyridinium iodide; and trans-4-[4-(Dimethylamino) styryl]-1-methylpyridinium p-toluenesulfonate.

26. The device of claim 1 wherein said first photonic crystal has a receiving surface for receiving said electromagnetic radiation generated by a laser, wherein the receiving surface has a curvature substantially similar to the curvature of said eye.

27. The device of claim 1 comprising a visor, helmet, goggles, eyeglasses, a shield, or a window.

28. The device of claim 1 wherein said electromagnetic radiation generated by a said laser has wavelengths in the ultraviolet region, visible region or infrared region of the electromagnetic spectrum.

29. A photonic crystal having a tunable photonic band gap comprising:
a dielectric structure having a spatial distribution of refractive indices that varies periodically in at least one dimension, said dielectric structure comprising alternating high refractive index elements and low refractive index elements provided in a periodic spatial configuration; said low refractive index elements or high refractive index elements comprising a photodynamic polymer exhibiting a selectively variable refractive index that changes upon exposure to polarized electromagnetic radiation, wherein said tunable photonic band gap of said photonic crystal is provided by said photodynamic polymer of said dielectric structure that exhibits the selectively variable refractive index that changes upon exposure to an excitation beam of polarized electromagnetic radiation.

30. The photonic crystal of claim 29 wherein said dielectric structure comprises a one-dimensional periodic array of said high refractive index elements and said low refractive index elements, and wherein said dielectric structure has a spatial distribution of refractive indices that varies periodically in one dimension.

31. The photonic crystal of claim 29 wherein said dielectric structure comprises a two-dimensional periodic array of said high refractive index elements and said low refractive index elements, and wherein said dielectric structure has a spatial distribution of refractive indices that varies periodically in two dimensions.

32. The photonic crystal of claim 29 wherein said dielectric structure comprises a three-dimensional periodic array of said high refractive index elements and said low refractive index elements, and wherein said dielectric structure has a spatial distribution of refractive indices that varies periodically in three dimensions.

33. The photonic crystal of claim 29 wherein said periodic spatial configuration has a non-varying period in two or more dimensions.

34. The photonic crystal of claim 29 wherein said low refractive index elements have said selectively variable refractive index and wherein said high refractive index elements have a fixed refractive index.

35. The photonic crystal of claim 34 wherein said high refractive index structural elements have a refractive index that is at least 1.2 times larger than said low refractive index elements.

36. The photonic crystal of claim 29 wherein said high refractive index elements have said selectively variable refractive index and wherein said low refractive index elements have a fixed refractive index.

37. The photonic crystal of claim 29 wherein said photodynamic polymer has a selectively variable refractive index birefringence, and wherein said photodynamic polymer exhibits an increase in birefringence upon exposure to said polarized electromagnetic radiation.

38. The photonic crystal of claim 29 wherein said photodynamic polymer comprises a dye material embedded in a polymer matrix.

39. The photonic crystal of claim 38 wherein said dye material comprises an azobenzene dye.

40. The photonic crystal of claim 39 wherein said azobenzene dye is selected from the group consisting of:
N-ethyl-N-(2-hydroxyethyl)-4-(4 nitrophenylazo)aniline;
4-(dimethylamino)azobenzene; and
2-(4-Dimethylaminophenylazo)benzoic acid.

41. The photonic crystal of claim 39 wherein said azobenzene dye comprises from about 1% to about 10% by mass of said photodynamic polymer.

42. The photonic crystal of claim 38 wherein said polymer matrix is selected from the group consisting of: polymethylmethacrylate (PMMA); polyvinylcarbazole (PVK); and polyacrylic acid (PAA).

43. The photonic crystal of claim 38 wherein said dye material is selected from the group consisting of: (2,6-Dimethyl-4H-pyran-4-ylidene)malononitrile; (S)-(−)-1-(4-Nitrophenyl)-2-pyrrolidinemethanol; [4-[Bis(2-hydroxyethyl)amino]phenyl]-1,1,2-ethylenetricarbonitrile; 1-Docosyl-4-(4-hydroxystyryl)pyridinium bromide; 2-(Dimethylamino)vinyl-1-nitronaphthalene; 2,3,5,6-Tetrafluoro-7,7,8,8-tetracyanoquinodimethane; 2-[[5-(Dibutylamino)-2-thienyl]methylene]-1H-indene-1,3(2H)-dione; 2-[4-((4-(Bis(2-hydroxyethyl)amino]phenyl)(cyano)methylene]-2,5-cyclohexadien-1-ylidene]malonitrile; 2-[4-(Dimethylamino)styryl]pyridine; 2-[Ethyl[4-[2-(4-nitrophenyl)ethenyl]phenyl]amino]ethanol; 2-Amino-3-nitropyridine; 2-Amino-5-nitropyridine; 2-Aminofluorene; 2-Chloro-3,5-dinitropyridine; 2-Chloro-4-nitroaniline; 2-Nitroaniline; 3-[(4-Nitrophenyl)azo]-9H-carbazole-9-ethanol; 3-Methyl-4-nitropyridine N-oxide; 3-Nitroaniline; 4-(Dibenzylamino)benzaldehyde-N,N-diphenylhydrazone; 4-[4-(Dimethylamino)styryl]-1-docosylpyridinium bromide; 4-[4-(Dimethylamino)styryl]pyridine; 4-Dimethylamino-4'-nitrostilbene; 4-Nitroaniline; 5-Nitroindole; 5-Nitrouracil; 7,7,8,8-Tetracyanoquinodimethane; 9-Ethyl-3-carbazolecarboxaldehyde-N-methyl-N-phenylhydrazone; 3-[N-Ethyl-4-(4-nitrophenylazo)phenylamino]propionitrile (Disperse Orange 25); 4-(4-Nitrophenylazo)aniline (Disperse Orange 3); N-Ethyl-N-(2-hydroxyethyl)-4-(4-nitrophenylazo)aniline (Disperse Red 1); 2-[4-(2-Chloro-4-nitrophenylazo)-N-ethylphenylamino]ethanol (Disperse Red 13); Disperse Red 19; 4-[4-(Phenylazo)phenylazo]-o-cresol (Disperse Yellow 7); Ethyl 4-(dimethylamino)benzoate; Hexamethylpararosaniline chloride (Crystal Violet); N-(2,4-Dinitrophenyl)-L-alanine methyl ester; N,N-Dimethyl-N'-[(5-nitro-2-thienyl)methylene]-1,4-phenylenediamine; N-[3-Cyano-3-[4-(dicyanomethyl)phenyl]-2-propenylidene]-N-ethyl-ethaniminium; Nile Blue A (Basic Blue 12); N-Methyl-4-nitroaniline; trans-4-[4-(Dimethylamino)styryl]-1-methylpyridinium iodide; and trans-4-[4-(Dimethylamino)styryl]-1-methylpyridinium p-toluenesulfonate.

44. The device of claim 29 wherein said low refractive index elements comprise said photodynamic polymeric material.

45. The device of claim 29 wherein said high refractive index elements comprise thin dielectric films.

46. The device of claim 29 further comprising a substrate having alternating raised and recessed relief features provided in a periodic configuration, wherein said high refractive index elements are disposed on top of said raised and recessed relief features of said substrate and wherein a portion of said low refractive index elements are said raised feature of said substrate.

47. The device of claim 29 further comprising a superstrate having alternating raised and recessed relief features provided in a periodic configuration, wherein said superstrate is in contact with at least a portion of said high refractive index elements, and wherein at least a portion of said low refractive index elements are said raised relief features of said superstrate.

48. The photonic crystal of claim 29 wherein said dielectric structure further comprises at least one defect in said dielectric structure comprising alternating high refractive index elements and low refractive index elements.

49. A method for tuning the frequency distribution of a photonic band gap of a photonic crystal; said method comprising the steps of:
providing said photonic crystal comprising a dielectric structure having a spatial distribution of refractive indices that varies periodically in at least one dimension, said dielectric structure comprising alternating high refractive index elements and low refractive index elements provided in a periodic spatial configuration; said low refractive index elements or said high refractive index elements comprising a photodynamic polymer exhibiting a selectively variable refractive index that changes upon exposure to polarized electromagnetic radiation; and
exposing said photonic crystal to polarized electromagnetic radiation, thereby changing the refractive index of said low refractive index elements or said high refractive index elements and, thereby tuning the frequency distribution of a photonic band gap of said photonic crystal.

50. The method of claim 49 wherein said photodynamic polymer comprises a dye material embedded in a polymer matrix.

51. The method of claim 50 wherein said dye material comprises an azobenzene dye.

52. The method of claim 49 wherein said polarized electromagnetic radiation has frequencies that are absorbed by said photodynamic polymer.

53. The method of claim 49 wherein said polarized electromagnetic radiation has a power per area selected over the range of about 0.5 mW $mm^{-2}$ to about 150 mW $mm^{-2}$.

54. The method of claim 49 wherein said photodynamic polymer undergoes a change in refractive index equal to a value selected over the range of 0.001 to 0.1 upon exposure to said polarized electromagnetic radiation.

55. An optical switching device for optically modulating an input optical beam of electromagnetic radiation having a frequency distribution comprising:
a photonic crystal having a photonic band gap with a tunable frequency distribution for receiving said input optical beam of electromagnetic radiation comprising a dielectric structure having a spatial distribution of refractive indices that varies periodically in at least one dimension, said dielectric structure comprising alternating high refractive index elements and low refractive index elements provided in a periodic spatial configuration; said low refractive index elements or high refractive index elements comprising a photodynamic polymer; wherein said tunable photonic band gap of said photonic crystal is provided by said photodynamic polymer of said dielectric structure that exhibits a selectively variable refractive index that changes upon exposure to an excitation beam of polarized electromagnetic radiation; and an excitation optical source in optical communication with said photonic crystal, said excitation optical source for providing said excitation beam of polarized electromagnetic radiation to said photonic crystal.

56. The device of claim 55 wherein said periodic spatial configuration of alternating high refractive index elements and low refractive index elements of the photonic crystal is selected such that said exposure of said photonic crystal to said excitation beam of polarized electromagnetic radiation shifts the frequency distribution of the photonic band gap such that it does not significantly overlap with said frequency distribution of said input optical beam, thereby allowing transmission of said input optical beam of electromagnetic radiation through said photonic crystal.

57. The device of claim 55 wherein said periodic spatial configuration of alternating high refractive index elements and low refractive index elements of the photonic crystal is selected such that said exposure of said photonic crystal to said excitation beam of polarized electromagnetic radiation shifts the frequency distribution of the photonic band gap such that it does significantly overlap with said frequency distribution of said input optical beam, thereby substantially preventing transmission of said input optical beam of electromagnetic radiation through said photonic crystal.

58. The device of claim 55 wherein said photonic crystal has a receiving surface for receiving said input optical beam of electromagnetic radiation, wherein said input optical beam of electromagnetic radiation propagates along an optical axis that is normally incident to said receiving surface and wherein said excitation beam of polarized electromagnetic radiation propagates along an optical axis that is not normally incident to said receiving surface.

59. The device of claim 55 wherein said dielectric structure comprises a one-dimensional periodic array of structural elements longitudinally oriented along alignment axes oriented parallel to a grating axis, wherein said input optical beam of electromagnetic radiation has a polarization perpendicular to said alignment axes of said structural elements.

60. The device of claim 55 wherein said excitation beam of polarized electromagnetic radiation has frequencies that are absorbed by said photodynamic polymer.

61. The device of claim 55 wherein said excitation beam of polarized electromagnetic radiation has a power per area selected over the range of about 0.5 mW $mm^{-2}$ to about 150 mW $mm^{-2}$.

62. The device of claim 55 wherein said photodynamic polymer undergoes a change in refractive index equal to a value selected over the range of 0.001 to 0.1 upon exposure to said excitation beam of polarized electromagnetic radiation.

63. The device of claim 55 wherein said frequency distribution of the photonic band gap shifts by about 1 nanometer to about 20 nanometers upon exposure to said excitation beam of polarized electromagnetic radiation.

64. The device of claim 55 wherein said photodynamic polymer comprises a dye material embedded in a polymer matrix.

65. The device of claim 64 wherein said dye material comprises an azobenzene dye.

66. The device of claim 65 wherein said azobenzene dye is selected from the group consisting of:

N-ethyl-N-(2-hydroxyethyl)-4-(4 nitrophenylazo)aniline;

4-(dimethylamino)azobenzene; and 2-(4-Dimethylaminophenylazo)benzoic acid.

67. The device of claim 65 wherein said azobenzene dye comprises from about 1% to about 10% by mass of said photodynamic polymer.

68. The device of claim 64 wherein said polymer matrix is selected from the group consisting of: polymethylmethacrylate (PMMA); polyvinylcarbazole (PVK); and polyacrylic acid (PAA).

69. The device of claim 64 wherein said dye material is selected from the group consisting of: (2,6-Dimethyl-4H-pyran-4-ylidene)malononitrile; (S)-(–)-1-(4-Nitrophenyl)-2-pyrrolidinemethanol; [4-[Bis(2-hydroxyethyl)amino]phenyl]-1,1,2-ethylenetricarbonitrile; 1-Docosyl-4-(4-hydroxystyryl)pyridinium bromide; 2-(Dimethylamino)vinyl-1-nitronaphthalene; 2,3,5,6-Tetrafluoro-7,7,8,8-tetracyanoquinodimethane; 2-[[5-(Dibutylamino)-2-thienyl]methylene]-1H-indene-1,3(2H)-dione; 2-[4-((4-(Bis(2-hydroxyethyl)amino]phenyl](cyano)methylene]-2,5-cyclohexadien-1-ylidene]malonitrile; 2-[4-(Dimethylamino)styryl]pyridine; 2-[Ethyl[4-[2-(4-nitrophenyl)ethenyl]phenyl]amino]ethanol; 2-Amino-3-nitropyridine; 2-Amino-5-nitropyridine; 2-Aminofluorene; 2-Chloro-3,5-dinitropyridine; 2-Chloro-4-nitroaniline; 2-Nitroaniline; 3-[(4-Nitrophenyl)azo]-9H-carbazole-9-ethanol; 3-Methyl-4-nitropyridine N-oxide; 3-Nitroaniline; 4-(Dibenzylamino)benzaldehyde-N,N-diphenylhydrazone; 4-[4-(Dimethylamino)styryl]-1-docosylpyridinium bromide; 4-[4-(Dimethylamino)styryl]pyridine; 4-Dimethylamino-4'-nitrostilbene; 4-Nitroaniline; 5-Nitroindole; 5-Nitrouracil; 7,7,8,8-Tetracyanoquinodimethane; 9-Ethyl-3-carbazolecarboxaldehyde-N-methyl-N-phenylhydrazone; 3-[N-Ethyl-4-(4-nitrophenylazo)phenylamino]propionitrile (Disperse Orange 25); 4-(4-Nitrophenylazo)aniline (Disperse Orange 3); N-Ethyl-N-(2-hydroxyethyl)-4-(4-nitrophenylazo)aniline (Disperse Red 1); 2-[4-(2-Chloro-4-nitrophenylazo)-N-ethylphenylamino]ethanol (Disperse Red 13); Disperse Red 19; 4-[4-(Phenylazo)phenylazo]-o-cresol (Disperse Yellow 7); Ethyl 4-(dimethylamino)benzoate; Hexamethylpararosaniline chloride (Crystal Violet); N-(2,4-Dinitrophenyl)-L-alanine methyl ester; N,N-Dimethyl-N'-[(5-nitro-2-thienyl)methylene]-1,4-phenylenediamine; N-[3-Cyano-3-[4-(dicyanomethyl)phenyl]-2-propenylidene]-N-ethyl-ethaniminium; Nile Blue A (Basic Blue 12); N-Methyl-4-nitroaniline; trans-4-[4-(Dimethylamino)styryl]-1-methylpyridinium iodide; and trans-4-[4-(Dimethylamino)styryl]-1-methylpyridinium p-toluenesulfonate.

70. The device of claim 55 wherein said excitation optical source is a laser or light emitting diode optical source.

71. The device of claim 55 further comprising an input beam optical source for providing said input optical beam to said photonic crystal.

72. The device of claim 55 wherein said dielectric structure comprises a one-dimensional periodic array of structural elements and has a spatial distribution of refractive indices that varies periodically in one dimension.

73. The device of claim 55 wherein said dielectric structure comprises a two-dimensional periodic array of structural elements and has a spatial distribution of refractive indices that varies periodically in two dimensions.

74. The device of claim 55 wherein said dielectric structure comprises a three-dimensional periodic array of structural elements and has a spatial distribution of refractive indices that varies periodically in three dimensions.

75. The device of claim 55 wherein said low refractive index elements comprise said photodynamic polymeric material and wherein said high refractive index elements comprise thin dielectric films.

76. The device of claim 55 further comprising a substrate having alternating raised and recessed relief features provided in a periodic configuration, wherein said high refractive index elements are disposed on top of said raised and recessed relief features of said substrate and wherein a portion of said low refractive index elements are said raised feature of said substrate.

77. The device of claim 55 further comprising a superstrate having alternating raised and recessed relief features provided in a periodic configuration, wherein said superstrate is in contact with at least a portion of said high refractive index elements, and wherein at least a portion of said low refractive index elements are said raised relief features of said superstrate.

78. A method for modulating the intensity of an input optical beam having a frequency distribution; said method comprising the steps of:
    directing said input optical beam onto a photonic crystal having a photonic band gap with a tunable frequency distribution comprising a dielectric structure having a spatial distribution of refractive indices that varies periodically in at least one dimension, said dielectric structure comprising alternating high refractive index elements and low refractive index elements provided in a periodic spatial configuration; said low refractive index elements or said high refractive index elements comprising a photodynamic polymer exhibiting a selectively variable refractive index that changes upon exposure to an excitation beam of polarized electromagnetic radiation; and
    changing the frequency distribution of the photonic band gap of said photonic crystal by exposing said photonic crystal to said excitation beam of polarized electromagnetic radiation, thereby modulating the intensity of said input optical beam.

79. The method of claim 78 wherein the periodic spatial configuration of alternating high refractive index elements and low refractive index elements of the photonic crystal is selected such that exposure of the photonic crystal to said excitation beam of polarized electromagnetic radiation changes the frequency distribution of the photonic band gap from a frequency distribution that significantly overlaps said distribution of wavelengths of said input optical beam to a frequency distribution that does not significantly overlap said distribution of wavelengths of said input optical beam, thereby allowing transmission of said input optical beam of electromagnetic radiation through said photonic crystal.

80. The method of claim 78 wherein the periodic spatial configuration of alternating high refractive index elements and low refractive index elements of the photonic crystal is selected such that exposure of the photonic crystal to said excitation beam of polarized electromagnetic radiation changes the frequency distribution of the photonic band gap from a frequency distribution that does not significantly overlap said distribution of wavelengths of said input optical beam to a frequency distribution that does significantly overlap said distribution of wavelengths of said input optical beam, thereby substantially preventing transmission of said input optical beam of electromagnetic radiation through said photonic crystal.

81. The method of claim 78 wherein said dielectric structure comprises a one-dimensional periodic array of structural elements and has a spatial distribution of refractive indices that varies periodically in one dimension.

82. The method of claim 78 wherein said dielectric structure comprises a two-dimensional periodic array of structural elements and has a spatial distribution of refractive indices that varies periodically in two dimensions.

83. The method of claim 78 wherein said dielectric structure comprises a three-dimensional periodic array of structural elements and has a spatial distribution of refractive indices that varies periodically in three dimensions.

84. An optical device for protecting an eye or sensor from electromagnetic radiation generated by a laser; said device comprising;
    a first photonic crystal having a spatial distribution of refractive indices that varies periodically in at least two dimensions and positioned to intersect said electromagnetic radiation generated by said laser, said first photonic crystal comprising a dielectric structure comprising alternating high refractive index elements and low refractive index elements provided in a periodic spatial configuration in at least two dimensions, said photonic crystal having a photonic band gap; and
    a second photonic crystal positioned in optical communication with said first photonic crystal and positioned to intersect said electromagnetic radiation generated by said laser; said second photonic crystal having a spatial distribution of refractive indices that varies periodically in at least two dimensions and comprising a dielectric structure comprising alternating high refractive index elements and low refractive index elements provided in a periodic spatial configuration in two dimensions, said second photonic crystal having a photonic band gap,
    wherein said first photonic crystal and said second photonic crystal are components of the optical device for protecting said eye or said sensor from the electromagnetic radiation generated by said laser.

85. The device of claim 84 wherein said band gap of said second photonic crystal has a different photonic band gap frequency distribution than that of said band gap of said first photonic crystal.

86. The device of claim 84 wherein the second photonic crystal is separated from said first photonic crystal by a separation layer, said separation layer having a substantially uniform thickness, thereby maintaining a selected optical pathlength between said first photonic crystal and said second photonic crystal for incident electromagnetic radiation having a given angle of incidence.

87. The device of claim 86 wherein said optical pathlength between said first photonic crystal and said second photonic crystal is sufficiently small to provide optical coupling of electromagnetic radiation diffracted by said first photonic crystal and said second photonic crystal.

88. The device of claim 86 wherein said separation layer comprises a polymeric material.

89. The device of claim 86 wherein said first photonic crystal has a first optical axis and said second photonic crystal has a second optical axis that is offset relative to said first optical axis of said first photonic crystal.

90. The device of claim 89 wherein said second optical axis is offset relative to said first optical axis of said first photonic crystal by about 45 degrees.

91. The device of claim 84 wherein said first photonic crystal and said second photonic crystal have substantially the same spatial distributions of refractive indices that vary periodically in at least two dimensions.

92. The device of claim 84 wherein said first photonic crystal and said second photonic crystal have different spatial distributions of refractive indices that vary periodically in at least two dimensions.

93. The device of claim 84 wherein said low refractive index elements, high refractive index elements or both of said second photonic crystal comprise a photodynamic polymer having a selectively variable refractive index that changes upon exposure to said electromagnetic radiation generated by said laser.

94. The device of claim 93 wherein said photodynamic polymer comprises a dye material embedded in a polymer matrix.

95. The device of claim 94 wherein said dye material comprises an azobenzene molecule.

96. The device of claim 95 wherein said azobenzene molecule is selected from the group consisting of:
N-ethyl-N-(2-hydroxyethyl)-4-(4-nitrophenylazo)aniline;
4-(dimethylamino)azobenzene; and
2-(4-Dimethylaminophenylazo)benzoic acid.

97. The device of claim 94 wherein said dye material is selected from the group consisting of: (2,6-Dimethyl-4H-pyran-4-ylidene)malononitrile; (S)-(−)-1-(4-Nitrophenyl)-2-pyrrolidinemethanol; [4-[Bis(2-hydroxyethyl)amino]phenyl]-1,1,2-ethylenetricarbonitrile; 1-Docosyl-4-(4-hydroxystyryl)pyridinium bromide; 2-(Dimethylamino)vinyl-1-nitronaphthalene; 2,3,5,6-Tetrafluoro-7,7,8,8-tetracyanoquinodimethane; 2-[[5-(Dibutylamino)-2-thienyl]methylene]-1H-indene-1,3(2H)-dione; 2-[4-((4-(Bis(2-hydroxyethyl)amino]phenyl)(cyano)methylene]-2,5-cyclohexadien-1-ylidene]malonitrile; 2-[4-(Dimethylamino)styryl]pyridine; 2-[Ethyl[4-[2-(4-nitrophenyl)ethenyl]phenyl]amino]ethanol; 2-Amino-3-nitropyridine; 2-Amino-5-nitropyridine; 2-Aminofluorene; 2-Chloro-3,5-dinitropyridine; 2-Chloro-4-nitroaniline; 2-Nitroaniline; 3-[(4-Nitrophenyl)azo]-9H-carbazole-9-ethanol; 3-Methyl-4-nitropyridine N-oxide; 3-Nitroaniline; 4-(Dibenzylamino)benzaldehyde-N,N-diphenylhydrazone; 4-[4-(Dimethylamino)styryl]-1-docosylpyridinium bromide; 4-[4-(Dimethylamino)styryl]pyridine; 4-Dimethylamino-4'-nitrostilbene; 4-Nitroaniline; 5-Nitroindole; 5-Nitrouracil; 7,7,8,8-Tetracyanoquinodimethane; 9-Ethyl-3-carbazolecarboxaldehyde-N-methyl-N-phenylhydrazone; 3-[N-Ethyl-4-(4-nitrophenylazo)phenylamino]propionitrile (Disperse Orange 25); 4-(4-Nitrophenylazo)aniline (Disperse Orange 3); N-Ethyl-N-(2-hydroxyethyl)-4-(4-nitrophenylazo)aniline (Disperse Red 1); 2-[4-(2-Chloro-4-nitrophenylazo)-N-ethylphenylamino]ethanol (Disperse Red 13); Disperse Red 19; 4-[(Phenylazo)phenylazo]-o-cresol (Disperse Yellow 7); Ethyl 4-(dimethylamino)benzoate; Hexamethylpararosaniline chloride (Crystal Violet); N-(2,4-Dinitrophenyl)-L-alanine methyl ester; N,N-Dimethyl-N'-[(5-nitro-2-thienyl)methylene]-1,4-phenylenediamine; N-[3-Cyano-3-[4-(dicyanomethyl)phenyl]-2-propenylidene]-N-ethylethaniminium; Nile Blue A (Basic Blue 12); N-Methyl-4-nitroaniline; trans-4-[4-(Dimethylamino)styryl]-1-methylpyridinium iodide; and trans-4-[4-(Dimethylamino)styryl]-1-methylpyridinium p-toluenesulfonate.

98. The device of claim 84 wherein said first photonic crystal has a receiving surface for receiving said electromagnetic radiation generated by a laser, wherein the receiving surface has a curvature substantially similar to the curvature of said eye.

99. The device of claim 84 comprising a visor, helmet, goggles, eyeglasses, a shield, or a window.

100. The device of claim 84 wherein said electromagnetic radiation generated by said laser has wavelengths in the ultraviolet region, visible region or infrared region of the electromagnetic spectrum.

* * * * *

UNITED STATES PATENT AND TRADEMARK OFFICE
CERTIFICATE OF CORRECTION

| | | |
|---|---|---|
| PATENT NO. | : 7,854,505 B2 | |
| APPLICATION NO. | : 11/686452 | |
| DATED | : December 21, 2010 | |
| INVENTOR(S) | : Cunningham et al. | |

It is certified that error appears in the above-identified patent and that said Letters Patent is hereby corrected as shown below:

In claim 8, column 40, lines 27-28, please replace "raised f aturo features" with --raised features--.

Signed and Sealed this
Twenty-fourth Day of May, 2011

David J. Kappos
*Director of the United States Patent and Trademark Office*